United States Patent [19]

Wingert et al.

[11] Patent Number: 5,112,860
[45] Date of Patent: May 12, 1992

[54] THIOCARBOXYLIC ESTERS AND FUNGICIDES CONTAINING THEM

[75] Inventors: Horst Wingert; Hubert Sauter, both of Mannheim; Siegbert Brand, Birkenheide; Bernd Wenderoth, Lampertheim; Gisela Lorenz, Neustadt; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 608,351

[22] Filed: Nov. 2, 1990

[30] Foreign Application Priority Data

Nov. 16, 1989 [DE] Fed. Rep. of Germany ....... 3938054
Sep. 13, 1990 [DE] Fed. Rep. of Germany ....... 4029092

[51] Int. Cl.⁵ ............................................. A01N 37/40
[52] U.S. Cl. .................... 514/513; 514/256; 514/311; 514/345; 514/359; 514/363; 514/365; 514/398; 514/381; 514/445; 514/461; 544/242; 544/298; 546/152; 546/329; 546/334; 546/335; 548/182; 548/250; 548/251; 548/263.2; 548/335; 548/337; 549/62; 549/429; 558/230; 558/250; 558/256; 558/257
[58] Field of Search ............... 558/230, 250, 256, 257; 546/200, 290; 514/513, 520

[56] References Cited

FOREIGN PATENT DOCUMENTS 0254426 6/1987 European Pat. Off. .
0253213 1/1988 European Pat. Off. .
0299694 1/1989 European Pat. Off. .
51-43714 4/1976 Japan .

OTHER PUBLICATIONS

Ogura et al, Tetrahedron Letters, No. 4, 375–378, 1978.

Primary Examiner—Richard L. Raymond
Assistant Examiner—Shakendra Kumar
Attorney, Agent, or Firm—Oblon, Spivak, McClelland, Maier & Neustadt

[57] ABSTRACT

Thiocarboxylic esters of the formula I

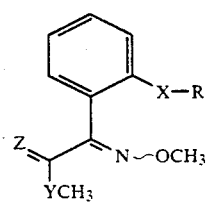

where the substituents have the following meanings:
  X is oxygen, sulfur, oxymethylene, methyleneoxy, thiomethylene, methylenethio, ethylene, ethenylene or ethynylene,
  Y, Z are each sulfur or oxygen, but Y and Z are not simultaneously oxygen,
  R is alkyl, mononuclear, dinuclear or trinuclear aryl or hetaryl, where aryl and hetaryl may be substituted,
and fungicidal agents containing these compounds.

6 Claims, No Drawings

THIOCARBOXYLIC ESTERS AND FUNGICIDES CONTAINING THEM

The present invention relates to novel thiocarboxylic esters of the general formula I

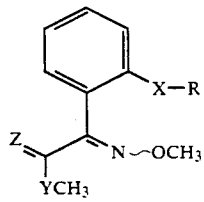

where X is oxygen, sulfur, oxymethylene, methyleneoxy, thiomethylene, methylenethio, ethylene, ethenylene or ethynylene, Y and Z are each sulfur or oxygen, but Y and Z are not simultaneously oxygen, and R is $C_1-C_6$-alkyl, mononuclear, dinuclear or trinuclear aryl or hetaryl, where aryl and hetaryl may carry the following radicals $R^1$: halogen, cyano, nitro, $C_1-C_6$-alkyl, $C_3-C_6$-cycloalkyl, $C_1-C_6$-alkoxy, trifluoromethyl, mononuclear or dinuclear aryloxy or mononuclear, dinuclear or trinuclear aryl, and aryloxy and aryl in turn may be substituted by the stated radicals $R^1$.

The present invention furthermore relates to a process for the preparation of these compounds, fungicides containing these compounds and a method for controlling fungi with the aid of these compounds or these fungicides.

Fungicides having a phenylglyoxylic acid oxime structure are disclosed in EP-A1-253 213, EP-A2-254 426 and EP-A2-299 694. Many of the compounds described in the stated publications have an unsatisfactory fungicidal action.

It is an object of the present invention to provide fungicides having a better action.

We have found that this object is achieved by the thiocarboxylic esters I defined at the outset.

Preferred thiocarboxylic esters I are those in which the substituents have the following meanings: X is methyleneoxy, methylenethio, oxymethylene, thiomethylene, ethylene, ethenylene or ethynylene and R is methyl, ethyl, n-propyl, isopropyl, n-butyl, iso-butyl, sec-butyl, tert-butyl, $C_6-C_{14}$-aryl (such as phenyl, 1-naphthyl, 2-naphthyl or phenanthryl), five-membered or six-membered heteroaromatic rings which contain one, two, three or four of the hetero atoms N, O or S (such as pyridyl, pyrimidyl, pyrazinyl, pyridazinyl, imidazolyl, 1,2,3- or 1,2,4-triazolyl, 1,2,4,5-tetrazinyl, furyl, pyrazolyl, thienyl, thiazolyl or thiadiazolyl) and may carry one or two fused-on aromatic rings (such as benzofuryl, benzothienyl, benzothiazolyl, quinolyl or quinoxazolyl), where aryl and hetaryl may be substituted and may carry, for example, the following radicals $R^1$: fluorine, chlorine, bromine, cyano, nitro, trifluoromethyl, $C_1-C_4$-alkyl, such as methyl, ethyl, n-propyl, isopropyl, n-butyl, isobutyl, sec-butyl or tert-butyl, cyclopropyl, cyclopentyl, cyclohexyl, $C_1-C_4$-alkoxy, such as methoxy, ethoxy, n-propoxy, isopropoxy, n-butoxy, isobutoxy, sec-butoxy or tert-butoxy, phenoxy, 1-naphthyloxy, 2-naphthyloxy, phenyl, 1-naphthyl or 2-naphthyl, where aryloxy and aryl in turn may be substituted by radicals which have the same preferred meanings as $R^1$.

The thiocarboxylic esters I are obtained, for example, by converting a carboxylic ester of the general formula II in a conventional manner (Organikum, 16th edition, page 415, 622) by hydrolysis into the carboxylic acid III and then reacting the latter, likewise in a conventional manner (Houben-Weyl, Vol. E5, page 855 et seq., 1985), with methanethiol or with an alkali metal methanethiolate to give a thiocarboxylic ester I:

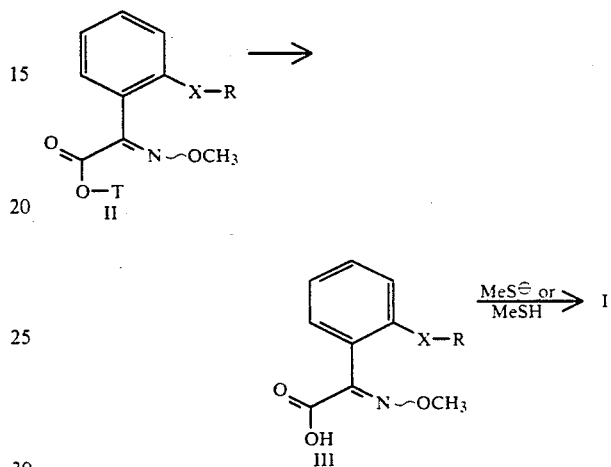

X and R have the same meanings as in formula I and T is a radical of an alcohol, preferably $C_1-C_4$-alkyl.

Because of the C=N double bond, the starting compounds II can occur as E/Z isomer mixtures or as pure E- or Z-isomers, so that the corresponding subsequent products, including the thiocarboxylic esters I, are obtained either as E/Z isomer mixtures or as E- or as Z-isomers. The wavy line in the formulae indicates this fact. The invention relates both to the individual isomeric compounds and to mixtures thereof. The carboxylic esters II are obtained by known methods which are described in detail in the patents EP-A1-253 213, EP-A2-254 426 and EP-A2-299 694.

The carboxylic esters II are, as a rule, hydrolyzed at from 60° to 120° C., preferably from 90° to 110° C., by reacting an aqueous alkali metal hydroxide solution, preferably a KOH solution, with the carboxylic ester, advantageously without an additional solvent. The reaction mixture is, as a rule, then acidified with concentrated hydrochloric acid to pH 0.5–1.5, preferably pH 0.8–1.2, at room temperature, the carboxylic acid III being precipitated.

The conversion of the carboxylic acids III to the thiocarboxylic esters I can be carried out, for example, via carbonyl chlorides as an intermediate (cf. Houben-Weyl Vol. 8 (1952), 464 et seq.), but the simpler method via an imidazolide or triazolide is preferred. Carbonyldiimidazole is preferably used, but it is also possible to employ, for example, carbonyldi-1,2,4-triazole (cf. Houben-Weyl, Vol. E5 (1985), 855 et seq.). The reaction is carried out in an inert anhydrous solvent, such as acetonitrile or dimethyl sulfoxide, in particular in dimethylformamide, at from −20° to 10° C., preferably from −15° to 0° C., at a pH of from 6 to 8, preferably from 6.5 to 7.5.

After this reaction, methanethiol or an alkali metal methanethiolate, in particular sodium methanethiolate or potassium methanethiolate, is added to the reaction mixture at from −20° to 40° C., in particular from −15° to 30° C., as a rule without isolation of the activated acid, the imidazolide or triazolide reacting with the thiol or thiolate to give the thiocarboxylic ester I.

The novel thiocarboxylic esters are also obtained by reacting the corresponding carboxylic esters IV, where Y is O, or the thiocarboxylic esters IV, where Y is S, at 100°–200° C. with a sulfurization agent, e.g. $P_4S_{10}$ or Lawesson's reagent, preferably with the latter (2,4-bis-(4-methoxyphenyl)-1,3-dithia-2,4-diphosphetan 2,4-disulfide)*, for example in a diluent, e.g. xylene or toluene (cf. S. O. Lawesson, Bull. Soc. Chim. Belg. 87 (1978), 293).

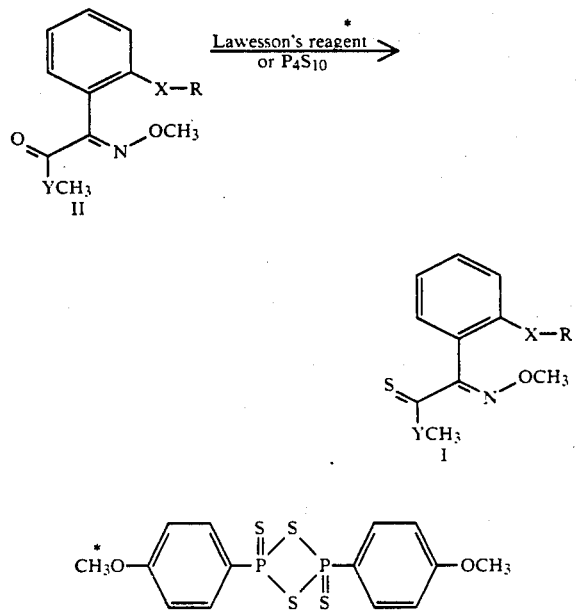

The Examples which follow illustrate the preparation of the thiocarboxylic esters I.

EXAMPLE 1

Preparation of 2-(2-chlorophenoxymethyl)-phenylthioglyoxylic acid methyl ester O-methyloxime 5 g of 2-(2-chlorophenoxymethyl)-phenylglyoxylic acid methyl ester O-methyloxime in 50 ml of 1N aqueous KOH solution were refluxed for 2 hours. The mixture was cooled, after which the pH was brought to 1 with concentrated hydrochloric acid. The precipitate which separated out was filtered off under suction and dried. 4 g of 2-(2-chlorophenoxymethyl)-phenylglyoxylic acid O-methyloxime were obtained as a colorless solid, which was then dissolved in 50 ml of anhydrous dimethylformamide. 2.1 g of carbonyldiimidazole were added at −10° C. and stirring was carried out at this temperature for 2 hours. 0.89 g of sodium methanethiolate was then added and stirring was continued for a further 90 minutes at −10° C. and then for a further 90 minutes at room temperature. 100 ml of methylene chloride and 200 ml of saturated, aqueous sodium chloride solution were added, after which the organic phase was separated off and dried over magnesium sulfate and the solvent was removed under reduced pressure. 3.8 g of crude product were obtained. This was purified by flash chromatography over silica gel using hexane/ethyl acetate. 2.3 g of product being obtained as a yellow solid of melting point 58° to 60° C.

EXAMPLE 2

Preparation of 2-[2-methylphenoxymethyl]-phenylthioglyoxylic acid methyl ester O-methyloxime 16.6 g (41 mmol) of Lawesson's reagent were added to 10.2 g (33 mmol) of 2-[2-methylphenoxymethyl]-phenylglyoxylic acid methyl ester O-methyloxime in 50 ml of xylene. Refluxing was carried out for 24 hours and the solvent was removed under reduced pressure. Chromatography over silica gel using ethyl acetate/hexane gave 6.3 g (59%) of the compound as a black oil.

$^1$H-NMR (CDCl$_3$): δ=2.27 (s, 3H), 4.03 (s, 3H), 4.19 (s, 3H), 4.95 (s, 2H), 6.78–7.61 ppm (m, 8H).

EXAMPLE 3

Preparation of 2-(2-methylphenoxymethyl)-phenyldithioglyoxylic acid methyl ester O-methyloxime 3.6 g (9 mmol) of Lawesson's reagent were added to a solution of 5 g (15 mmol) of 2-[2-methylphenoxymethyl]-phenylthioglyoxylic acid methyl ester O-methyloxime in 20 ml of toluene. Refluxing was carried out for 24 hours and the mixture was evaporated down. The residue was chromatographed over silica gel using ethyl acetate/hexane. 2.8 g (54%) of the compound were obtained as a black oil.

$^1$H-NMR (CDCl$_3$): δ=2.25 (s, 3H), 2.60 (s, 3H), 4.02 (s, 3H), 4.91 (s, 2H), 6.78–7.61 ppm (m, 8H).

The compounds shown in the Tables below can be prepared in a similar manner.

TABLE 1

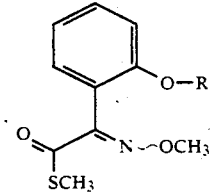

| No. | R | mp (°C.)/ IR (cm$^{-1}$) |
|---|---|---|
| 1 | methyl | |
| 2 | ethyl | |
| 3 | n-propyl | |
| 4 | iso-propyl | |
| 5 | n-butyl | |
| 6 | s-butyl | |
| 7 | iso-butyl | |
| 8 | tert.-butyl | |
| 9 | pentyl | |
| 10 | hexyl | |
| 11 | phenyl | |
| 12 | 2-F-phenyl | |
| 13 | 3-F-phenyl | |
| 14 | 4-F-phenyl | |
| 15 | 2-Cl-phenyl | |
| 16 | 3-Cl-phenyl | |
| 17 | 4-Cl-phenyl | |
| 18 | 2-Br-phenyl | |
| 19 | 3-Br-phenyl | |
| 20 | 4-Br-phenyl | |
| 21 | 2-I-phenyl | |
| 22 | 3-I-phenyl | |
| 23 | 4-I-phenyl | |
| 24 | 2-CN-phenyl | |

TABLE 1-continued

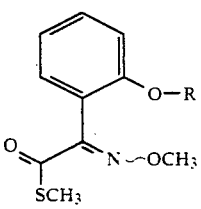

| No. | R | mp (°C.)/ IR (cm$^{-1}$) |
|---|---|---|
| 25 | 3-CN-phenyl | |
| 26 | 4-CN-phenyl | |
| 27 | 2,3-F$_2$-phenyl | |
| 28 | 2,4-F$_2$-phenyl | |
| 29 | 2,3-Cl$_2$-phenyl | |
| 30 | 2,4-Cl$_2$-phenyl | |
| 31 | 2,5-Cl$_2$-phenyl | |
| 32 | 2,6-Cl$_2$-phenyl | |
| 33 | 3,4-Cl$_2$-phenyl | |
| 34 | 3,5-Cl$_2$-phenyl | |
| 35 | 2,4-Br$_2$-phenyl | |
| 36 | 2,5-Br$_2$-phenyl | |
| 37 | 2,6-Br$_2$-phenyl | |
| 38 | 2,4-I$_2$-phenyl | |
| 39 | 2-Cl, 3-F-phenyl | |
| 40 | 2-Cl, 4-F-phenyl | |
| 41 | 2-Cl, 5-F-phenyl | |
| 42 | 2-Cl, 6-F-phenyl | |
| 43 | 2-Cl, 3-Br-phenyl | |
| 44 | 2-Cl, 4-Br-phenyl | |
| 45 | 2-Cl, 5-Br-phenyl | |
| 46 | 2-Cl, 6-Br-phenyl | |
| 47 | 2-Br, 3-Cl-phenyl | |
| 48 | 2-Br, 4-Cl-phenyl | |
| 49 | 2-Br, 3-F-phenyl | |
| 50 | 2-Br, 4-F-phenyl | |
| 51 | 2-Br, 5-F-phenyl | |
| 52 | 2-Br, 6-F-phenyl | |
| 53 | 2-F, 3-Cl-phenyl | |
| 54 | 2-F, 4-Cl-phenyl | |
| 55 | 2-F, 5-Cl-phenyl | |
| 56 | 3-Cl, 4-F-phenyl | |
| 57 | 3-Cl, 5-F-phenyl | |
| 58 | 3-Cl, 4-Br-phenyl | |
| 59 | 3-Cl, 5-Br-phenyl | |
| 60 | 3-F, 4-Cl-phenyl | |
| 61 | 3-F, 4-Br-phenyl | |
| 62 | 3-Br, 4-Cl-phenyl | |
| 63 | 3-Br, 4-F-phenyl | |
| 64 | 2,4,6-F$_3$-phenyl | |
| 65 | 2,3,4,-Cl$_3$-phenyl | |
| 66 | 2,3,5-Cl$_3$-phenyl | |
| 67 | 2,3,6-Cl$_3$-phenyl | |
| 68 | 2,4,5-Cl$_3$-phenyl | |
| 69 | 2,4,6-Cl$_3$-phenyl | |
| 70 | 3,4,5-Cl$_3$-phenyl | |
| 71 | 2,4,6-Br$_3$-phenyl | |
| 72 | 2,6-Cl$_2$-4-Br-phenyl | |
| 73 | 2,3,4,6-Cl$_4$-phenyl | |
| 74 | 2,3,5,6-Cl$_4$-phenyl | |
| 75 | F$_5$-phenyl | |
| 76 | Cl$_5$-phenyl | |
| 77 | Br$_5$-phenyl | |
| 78 | 2-CH$_3$-phenyl | |
| 79 | 3-CH$_3$-phenyl | |
| 80 | 4-CH$_3$-phenyl | |
| 81 | 2-C$_2$H$_5$-phenyl | |
| 82 | 3-C$_2$H$_5$-phenyl | |
| 83 | 4-C$_2$H$_5$-phenyl | |
| 84 | 2-n-C$_3$H$_7$-phenyl | |
| 85 | 3-n-C$_3$H$_7$-phenyl | |
| 86 | 4-n-C$_3$H$_7$-phenyl | |
| 87 | 2-i-C$_3$H$_7$-phenyl | |
| 88 | 3-i-C$_3$H$_7$-phenyl | |
| 89 | 4-i-C$_3$H$_7$-phenyl | |
| 90 | 2-s-C$_4$H$_9$-phenyl | |
| 91 | 3-s-C$_4$H$_9$-phenyl | |

TABLE 1-continued

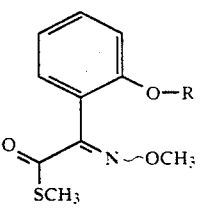

| No. | R | mp (°C.)/ IR (cm$^{-1}$) |
|---|---|---|
| 92 | 4-s-C$_4$H$_9$-phenyl | |
| 93 | 2-t-C$_4$H$_9$-phenyl | |
| 94 | 3-t-C$_4$H$_9$-phenyl | |
| 95 | 4-t-C$_4$H$_9$-phenyl | |
| 96 | 2,3-(CH$_3$)$_2$-phenyl | |
| 97 | 2,4-(CH$_3$)$_2$-phenyl | |
| 98 | 2,5-(CH$_3$)$_2$-phenyl | |
| 99 | 2,6-(CH$_3$)$_2$-phenyl | |
| 100 | 3,4-(CH$_3$)$_2$-phenyl | |
| 101 | 3,5-(CH$_3$)$_2$-phenyl | |
| 102 | 2,3,4-(CH$_3$)$_3$-phenyl | |
| 103 | 2,3,5-(CH$_3$)$_3$-phenyl | |
| 104 | 2,3,6-(CH$_3$)$_3$-phenyl | |
| 105 | 2,4,5-(CH$_3$)$_3$-phenyl | |
| 106 | 2,4,6-(CH$_3$)$_3$-phenyl | |
| 107 | 3,4,5-(CH$_3$)$_3$-phenyl | |
| 108 | 2,3,4,6-(CH$_3$)$_4$-phenyl | |
| 109 | 2,3,5,6-(CH$_3$)$_4$-phenyl | |
| 110 | (CH$_3$)$_5$-phenyl | |
| 111 | 2,4-(C$_2$H$_5$)$_2$-phenyl | |
| 112 | 2,6-(C$_2$H$_5$)$_2$-phenyl | |
| 113 | 3,5-(C$_2$H$_5$)$_2$-phenyl | |
| 114 | 2,4,6-(C$_2$H$_5$)$_3$-phenyl | |
| 115 | 2,4-(i-C$_3$H$_7$)$_2$-phenyl | |
| 116 | 2,6-(i-C$_3$H$_7$)$_2$-phenyl | |
| 117 | 3,5-(i-C$_3$H$_7$)$_2$-phenyl | |
| 118 | 2,4,6-(i-C$_3$H$_7$)$_3$-phenyl | |
| 119 | 2,3-(t-C$_4$H$_9$)$_2$-phenyl | |
| 120 | 2,4-(t-C$_4$H$_9$)$_2$-phenyl | |
| 121 | 2,5-(t-C$_4$H$_9$)$_2$-phenyl | |
| 122 | 2,6-(t-C$_4$H$_9$)$_2$-phenyl | |
| 123 | 3,5-(t-C$_4$H$_9$)$_2$-phenyl | |
| 124 | 2,4,6-(t-C$_4$H$_9$)$_3$-phenyl | |
| 125 | 2-t-C$_4$H$_9$, 4-CH$_3$-phenyl | |
| 126 | 2-t-C$_4$H$_9$, 5-CH$_3$-phenyl | |
| 127 | 2,6-(t-C$_4$H$_9$)$_2$, 4-CH$_3$-phenyl | |
| 128 | 2-CH$_3$, 4-t-C$_4$H$_9$-phenyl | |
| 129 | 2-CH$_3$, 6-t-C$_4$H$_9$-phenyl | |
| 130 | 2-CH$_3$, 4-i-C$_3$H$_7$-phenyl | |
| 131 | 2-CH$_3$, 5-i-C$_3$H$_7$-phenyl | |
| 132 | 3-CH$_3$, 4-i-C$_3$H$_7$-phenyl | |
| 133 | 2-i-C$_3$H$_7$, 5-CH$_3$-phenyl | |
| 134 | 2,4-(t-C$_4$H$_9$)$_2$-6-i-C$_3$H$_7$-phenyl | |
| 135 | 2-cyclo-C$_6$H$_{11}$-phenyl | |
| 136 | 3-cyclo-C$_6$H$_{11}$-phenyl | |
| 137 | 4-cyclo-C$_6$H$_{11}$-phenyl | |
| 138 | 2,4-(cyclo-C$_6$H$_{11}$)$_2$-6-CH$_3$-phenyl | |
| 139 | 2-CH$_3$, 4-cyclo-C$_6$H$_{11}$-phenyl | |
| 140 | 2-CH$_2$C$_6$H$_5$-phenyl | |
| 141 | 3-CH$_2$C$_6$H$_5$-phenyl | |
| 142 | 4-CH$_2$C$_6$H$_5$-phenyl | |
| 143 | 2-CH$_2$C$_6$H$_5$, 4-CH$_3$-phenyl | |
| 144 | 2-CH$_3$, 4-CH$_2$C$_6$H$_5$-phenyl | |
| 145 | 2-C$_6$H$_5$-phenyl | |
| 146 | 3-C$_6$H$_5$-phenyl | |
| 147 | 4-C$_6$H$_5$-phenyl | |
| 148 | 4-(2-i-C$_3$H$_7$—C$_6$H$_4$)-phenyl | |
| 149 | 4-C$_6$H$_5$, 2,6-(CH$_3$)$_2$-phenyl | |
| 150 | 2-Cl, 4-C$_6$H$_5$-phenyl | |
| 151 | 2-Br, 4-C$_6$H$_5$-phenyl | |
| 152 | 2-C$_6$H$_5$, 4-Cl-phenyl | |
| 153 | 2-C$_6$H$_5$, 4-Br-phenyl | |
| 154 | 2-CH$_2$C$_6$H$_5$, 4-Cl-phenyl | |
| 155 | 2-CH$_2$C$_6$H$_5$, 4-Br-phenyl | |
| 156 | 2-Cl, 4-CH$_2$C$_6$H$_5$-phenyl | |
| 157 | 2-Br, 4-CH$_2$C$_6$H$_5$-phenyl | |
| 158 | 2-cyclo-C$_6$H$_{11}$, 4-Cl-phenyl | |

TABLE 1-continued

[Structure: 2-(O-R)-phenyl group attached to C(=N-OCH3)-C(=O)-SCH3]

| No. | R | mp (°C.)/ IR (cm$^{-1}$) |
|---|---|---|
| 159 | 2-cyclo-C$_6$H$_{11}$, 4-Br-phenyl | |
| 160 | 2-Cl, 4-cyclo-C$_6$H$_{11}$-phenyl | |
| 161 | 2-Br, 4-cyclo-C$_6$H$_{11}$-phenyl | |
| 162 | 2-OCH$_3$-phenyl | |
| 163 | 3-OCH$_3$-phenyl | |
| 164 | 4-OCH$_3$-phenyl | |
| 165 | 2,4-(OCH$_3$)$_2$-phenyl | |
| 166 | 2-CF$_3$-phenyl | |
| 167 | 3-CF$_3$-phenyl | |
| 168 | 4-CF$_3$-phenyl | |
| 169 | 2-NO$_2$-phenyl | |
| 170 | 3-NO$_2$-phenyl | |
| 171 | 4-NO$_2$-phenyl | |
| 172 | 2-CN-phenyl | |
| 173 | 3-CN-phenyl | |
| 174 | 4-CN-phenyl | |
| 175 | 2-CH$_3$, 3-Cl-phenyl | |
| 176 | 2-CH$_3$, 4-Cl-phenyl | |
| 177 | 2-CH$_3$, 5-Cl-phenyl | |
| 178 | 2-CH$_3$, 6-Cl-phenyl | |
| 179 | 2-CH$_3$, 3-F-phenyl | |
| 180 | 2-CH$_3$, 4-F-phenyl | |
| 181 | 2-CH$_3$, 5-F-phenyl | |
| 182 | 2-CH$_3$, 6-F-phenyl | |
| 183 | 2-CH$_3$, 3-Br-phenyl | |
| 184 | 2-CH$_3$, 4-Br-phenyl | |
| 185 | 2-CH$_3$, 5-Br-phenyl | |
| 186 | 2-CH$_3$, 6-Br-phenyl | |
| 187 | 2-Cl, 3-CH$_3$-phenyl | |
| 188 | 2-Cl, 4-CH$_3$-phenyl | |
| 189 | 2-Cl, 5-CH$_3$-phenyl | |
| 190 | 2-Cl, 3-i-C$_3$H$_7$ | |
| 191 | 2-F, 3-CH$_3$-phenyl | |
| 192 | 2-F, 4-CH$_3$-phenyl | |
| 193 | 2-F, 5-CH$_3$-phenyl | |
| 194 | 2-Br, 3-CH$_3$-phenyl | |
| 195 | 2-Br, 4-CH$_3$-phenyl | |
| 196 | 3-CH$_3$, 4-Cl-phenyl | |
| 197 | 3-CH$_3$, 5-Cl-phenyl | |
| 198 | 2-Br, 5-CH$_3$-phenyl | |
| 199 | 3-CH$_3$, 4-F-phenyl | |
| 200 | 3-CH$_3$, 5-F-phenyl | |
| 201 | 3-CH$_3$, 4-Br-phenyl | |
| 202 | 3-CH$_3$, 5-Br-phenyl | |
| 203 | 3-F, 4-CH$_3$-phenyl | |
| 204 | 3-Cl, 4-CH$_3$-phenyl | |
| 205 | 3-Br, 4-CH$_3$-phenyl | |
| 206 | 2-Cl, 4,5-(CH$_3$)$_2$-phenyl | |
| 207 | 2-Br, 4,5-(CH$_3$)$_2$-phenyl | |
| 208 | 2-Cl, 3,5-(CH$_3$)$_2$-phenyl | |
| 209 | 2-Br, 3,5-(CH$_3$)$_2$-phenyl | |
| 210 | 2,6-Cl$_2$, 4-CH$_3$-phenyl | |
| 211 | 2,6-F$_2$, 4-CH$_3$-phenyl | |
| 212 | 2,6-Br$_2$, 4-CH$_3$-phenyl | |
| 213 | 2,4-Cl$_2$, 6-CH$_3$-phenyl | |
| 214 | 2,4-F$_2$, 6-CH$_3$-phenyl | |
| 215 | 2,4-Br$_2$, 6-CH$_3$-phenyl | |
| 216 | 2,6-(CH$_3$)$_2$, 4-F-phenyl | |
| 217 | 2,6-(CH$_3$)$_2$, 4-Cl-phenyl | |
| 218 | 2,6-(CH$_3$)$_2$, 4-Br-phenyl | |
| 219 | 3,5-(CH$_3$)$_2$, 4-F-phenyl | |
| 220 | 3,5-(CH$_3$)$_2$, 4-Cl-phenyl | |
| 221 | 3,5-(CH$_3$)$_2$, 4-Br-phenyl | |
| 222 | 2,3,6-(CH$_3$)$_3$, 4-F-phenyl | |
| 223 | 2,3,6-(CH$_3$)$_3$, 4-Cl-phenyl | |
| 224 | 2,3,6-(CH$_3$)$_3$, 4-Br-phenyl | |
| 225 | 2,4-(CH$_3$)$_2$, 6-F-phenyl | |
| 226 | 2,4-(CH$_3$)$_2$, 6-Cl-phenyl | |
| 227 | 2,4-(CH$_3$)$_2$, 6-Br-phenyl | |
| 228 | 2-i-C$_3$H$_7$, 4-Cl, 5-CH$_3$-phenyl | |
| 229 | 2-Cl, 4-NO$_2$-phenyl | |
| 230 | 2-NO$_2$, 4-Cl-phenyl | |
| 231 | 2-OCH$_3$, 5-NO$_2$-phenyl | |
| 232 | 2,4-Cl$_2$, 5-NO$_2$-phenyl | |
| 233 | 2,4-Cl$_2$, 6-NO$_2$-phenyl | |
| 234 | 2,6-Cl$_2$, 4-NO$_2$-phenyl | |
| 235 | 2,6-Br$_2$, 4-NO$_2$-phenyl | |
| 236 | 2,6-I$_2$, 4-NO$_2$-phenyl | |
| 237 | 2-C$_6$H$_5$O-phenyl | |
| 238 | 3-C$_6$H$_5$O-phenyl | |
| 239 | 4-C$_6$H$_5$O-phenyl | |
| 240 | 3-t-C$_4$H$_9$O-phenyl | |
| 241 | 4-t-C$_4$H$_9$O-phenyl | |
| 242 | 1-naphthyl | |
| 243 | 2-naphthyl | |
| 244 | 2-pyridyl | |
| 245 | 6-methyl-2-pyridyl | |
| 246 | 6-ethyl-2-pyridyl | |
| 247 | 6-n-propyl-2-pyridyl | |
| 248 | 6-iso-propyl-2-pyridyl | |
| 249 | 6-n-butyl-2-pyridyl | |
| 250 | 6-tert.-butyl-2-pyridyl | |
| 251 | 6-n-pentyl-2-pyridyl | |
| 252 | 6-n-hexyl-2-pyridyl | |
| 253 | 6-phenyl-2-pyridyl | |
| 254 | 6-benzyl-2-pyridyl | |
| 255 | 6-trifluoromethyl-2-pyridyl | |
| 256 | 6-methoxy-2-pyridyl | |
| 257 | 6-chloro-2-pyridyl | |
| 258 | 3,6-dimethyl-2-pyridyl | |
| 259 | 3,6-diethyl-2-pyridyl | |
| 260 | 4,6-dimethyl-2-pyridyl | |
| 261 | 5,6-dimethyl-2-pyridyl | |
| 262 | 4-phenyl-6-methyl-2-pyridyl | |
| 263 | 4,6-diphenyl-2-pyridyl | |
| 264 | 3,4-dichloro-6-methyl-2-pyridyl | |
| 265 | 3,4,5-trichloro-6-phenyl-2-pyridyl | |
| 266 | 4-trifluoromethyl-6-methyl-2-pyridyl | |
| 267 | 3-cyano-6-methyl-2-pyridyl | |
| 268 | 3-cyano-6-ethyl-2-pyridyl | |
| 269 | 3-cyano-6-n-propyl-2-pyridyl | |
| 270 | 3-cyano-6-iso-propyl-2-pyridyl | |
| 271 | 3-cyano-6-cyclo-propyl-2-pyridyl | |
| 272 | 3-cyano-6-n-butyl-2-pyridyl | |
| 273 | 3-cyano-6-tert.-butyl-2-pyridyl | |
| 274 | 3-cyano-6-cyclo-hexyl-2-pyridyl | |
| 275 | 3-cyano-6-phenyl-2-pyridyl | |
| 276 | 3-cyano-4,6-dimethyl-2-pyridyl | |
| 277 | 3,5,6-trichloro-2-pyridyl | |
| 278 | 5-trifluoromethyl-2-pyridyl | |
| 279 | 3-chloro-5-trifluoromethyl-2-pyridyl | |
| 280 | 2-quinolyl | |
| 281 | 3-methyl-2-quinolyl | |
| 282 | 4-methyl-2-quinolyl | |
| 283 | 4-ethyl-2-quinolyl | |
| 284 | 4-phenyl-2-quinolyl | |
| 285 | 6-methyl-2-quinolyl | |
| 286 | 6-chloro-2-quinolyl | |
| 287 | 8-methyl-2-quinolyl | |
| 288 | 8-chloro-2-quinolyl | |
| 289 | 3,4-dimethyl-2-quinolyl | |
| 290 | 4-methyl-8-methoxy-2-quinolyl | |
| 291 | 4-phenyl-8-ethoxy-2-quinolyl | |
| 292 | 4-methyl-8-chloro-2-quinolyl | |

TABLE 1-continued

Structure: 2-(O-R)-phenyl group with C(=O)SCH₃ and =N-OCH₃ substituents

| No. | R | mp (°C.)/ IR (cm⁻¹) |
|---|---|---|
| 293 | 4-methyl-8-fluoro-2-quinolyl | |
| 294 | 4-quinolyl | |
| 295 | 2-methyl-4-quinolyl | |
| 296 | 2-trifluoromethyl-4-quinolyl | |
| 297 | 2-iso-propyl-4-quinolyl | |
| 298 | 2-n-pentyl-4-quinolyl | |
| 299 | 2-phenyl-4-quinolyl | |
| 300 | 2,6-dimethyl-4-quinolyl | |
| 301 | 2-methyl-6-chloro-4-quinolyl | |
| 302 | 2-methyl-6-fluoro-4-quinolyl | |
| 303 | 8-quinolyl | |
| 304 | 2-methyl-8-quinolyl | |
| 305 | 5,7-dichloro-8-quinolyl | |
| 306 | 4,6-dimethyl-2-pyrimidinyl | |
| 307 | 4-trifluoromethyl-2-pyrimidinyl | |
| 308 | 4,5,6-trimethyl-2-pyrimidinyl | |
| 309 | 4-benzyl-6-methyl-2-pyrimidinyl | |
| 310 | 4-methyl-6-phenyl-2-pyrimidinyl | |
| 311 | 4,6-dimethyl-5-chloro-2-pyrimidinyl | |
| 312 | 2,6-dimethyl-4-pyrimidinyl | |
| 313 | 2,6-bis-(trifluoromethyl)-4-pyrimidinyl | |
| 314 | 2-iso-propyl-6-methyl-4-pyrimidinyl | |
| 315 | 2-cyclo-propyl-6-methyl-4-pyrimidinyl | |
| 316 | 2-methyl-6-methoxymethyl-4-pyrimidinyl | |
| 317 | 2-iso-propyl-6-methoxymethyl-4-pyrimidinyl | |
| 318 | 2-phenyl-4-pyrimidinyl | |
| 319 | 3,5-dimethyl-4-pyrimidinyl | |
| 320 | 2-methyl-6-trifluoromethyl-4-pyrimidinyl | |
| 321 | 2-n-propyl-6-trifluoromethyl-4-pyrimidinyl | |
| 322 | 2-iso-propyl-6-trifluoromethyl-4-pyrimidinyl | |
| 323 | 2-methyl-5-chloro-6-trifluoromethyl-4-pyrimidinyl | |
| 324 | 2-n-propyl-5-chloro-6-trifluoromethyl-4-pyrimidinyl | |
| 325 | 2-iso-propyl-5-chloro-6-trifluoromethyl-4-pyrimidinyl | |
| 326 | 2-tert.-butyl-5-chloro-6-trifluoromethyl-4-pyrimidinyl | |

TABLE 2

Structure: 2-(S-R)-phenyl group with C(=O)SCH₃ and =N-OCH₃ substituents

| No. | R | mp(°C.)/ IR(cm⁻¹) |
|---|---|---|
| 1 | methyl | |
| 2 | ethyl | |
| 3 | n-propyl | |
| 4 | iso-propyl | |
| 5 | n-butyl | |
| 6 | s-butyl | |
| 7 | iso-butyl | |
| 8 | tert.-butyl | |
| 9 | pentyl | |
| 10 | hexyl | |
| 11 | phenyl | |
| 12 | 2-F-phenyl | |
| 13 | 3-F-phenyl | |
| 14 | 4-F-phenyl | |
| 15 | 2-Cl-phenyl | |
| 16 | 3-Cl-phenyl | |
| 17 | 4-Cl-phenyl | |
| 18 | 2-Br-phenyl | |
| 19 | 3-Br-phenyl | |
| 20 | 4-Br-phenyl | |
| 21 | 2-I-phenyl | |
| 22 | 3-I-phenyl | |
| 23 | 4-I-phenyl | |
| 24 | 2-CN-phenyl | |
| 25 | 3-CN-phenyl | |
| 26 | 4-CN-phenyl | |
| 27 | 2,3-$F_2$-phenyl | |
| 28 | 2,4-$F_2$-phenyl | |
| 29 | 2,3-$Cl_2$-phenyl | |
| 30 | 2,4-$Cl_2$-phenyl | |
| 31 | 2,5-$Cl_2$-phenyl | |
| 32 | 2,6-$Cl_2$-phenyl | |
| 33 | 3,4-$Cl_2$-phenyl | |
| 34 | 3,5-$Cl_2$-phenyl | |
| 35 | 2,4-$Br_2$-phenyl | |
| 36 | 2,5-$Br_2$-phenyl | |
| 37 | 2,6-$Br_2$-phenyl | |
| 38 | 2,4-$I_2$-phenyl | |
| 39 | 2-Cl, 3-F-phenyl | |
| 40 | 2-Cl, 4-F-phenyl | |
| 41 | 2-Cl, 5-F-phenyl | |
| 42 | 2-Cl, 6-F-phenyl | |
| 43 | 2-Cl, 3-Br-phenyl | |
| 44 | 2-Cl, 4-Br-phenyl | |
| 45 | 2-Cl, 5-Br-phenyl | |
| 46 | 2-Cl, 6-Br-phenyl | |
| 47 | 2-Br, 3-Cl-phenyl | |
| 48 | 2-Br, 4-Cl-phenyl | |
| 49 | 2-Br, 3-F-phenyl | |
| 50 | 2-Br, 4-F-phenyl | |
| 51 | 2-Br, 5-F-phenyl | |
| 52 | 2-Br, 6-F-phenyl | |
| 53 | 2-F, 3-Cl-phenyl | |
| 54 | 2-F, 4-Cl-phenyl | |
| 55 | 2-F, 5-Cl-phenyl | |
| 56 | 3-Cl, 4-F-phenyl | |
| 57 | 3-Cl, 5-F-phenyl | |
| 58 | 3-Cl, 4-Br-phenyl | |
| 59 | 3-Cl, 5-Br-phenyl | |
| 60 | 3-F, 4-Cl-phenyl | |
| 61 | 3-F, 4-Br-phenyl | |
| 62 | 3-Br, 4-Cl-phenyl | |
| 63 | 3-Br, 4-F-phenyl | |
| 64 | 2,4,6-$F_3$-phenyl | |
| 65 | 2,3,4,-$Cl_3$-phenyl | |
| 66 | 2,3,5-$Cl_3$-phenyl | |
| 67 | 2,3,6-$Cl_3$-phenyl | |
| 68 | 2,4,5-$Cl_3$-phenyl | |
| 69 | 2,4,6-$Cl_3$-phenyl | |
| 70 | 3,4,5-$Cl_3$-phenyl | |
| 71 | 2,4,6-$Br_3$-phenyl | |
| 72 | 2,6-$Cl_2$-4-Br-phenyl | |
| 73 | 2,3,4,6-$Cl_4$-phenyl | |
| 74 | 2,3,5,6-$Cl_4$-phenyl | |
| 75 | $F_5$-phenyl | |
| 76 | $Cl_5$-phenyl | |
| 77 | $Br_5$-phenyl | |
| 78 | 2-$CH_3$-phenyl | |
| 79 | 3-$CH_3$-phenyl | |
| 80 | 4-$CH_3$-phenyl | |
| 81 | 2-$C_2H_5$-phenyl | |
| 82 | 3-$C_2H_5$-phenyl | |
| 83 | 4-$C_2H_5$-phenyl | |
| 84 | 2-n-$C_3H_7$-phenyl | |

TABLE 2-continued

[Structure: phenyl ring with S-R substituent, and C(=O)SCH₃ and C=N-OCH₃ groups]

| No. | R | mp(°C.)/IR(cm⁻¹) |
|---|---|---|
| 85 | 3-n-C₃H₇-phenyl | |
| 86 | 4-n-C₃H₇-phenyl | |
| 87 | 2-i-C₃H₇-phenyl | |
| 88 | 3-i-C₃H₇-phenyl | |
| 89 | 4-i-C₃H₇-phenyl | |
| 90 | 2-s-C₄H₉-phenyl | |
| 91 | 3-s-C₄H₉-phenyl | |
| 92 | 4-s-C₄H₉-phenyl | |
| 93 | 2-t-C₄H₉-phenyl | |
| 94 | 3-t-C₄H₉-phenyl | |
| 95 | 4-t-C₄H₉-phenyl | |
| 96 | 2,3-(CH₃)₂-phenyl | |
| 97 | 2,4-(CH₃)₂-phenyl | |
| 98 | 2,5-(CH₃)₂-phenyl | |
| 99 | 2,6-(CH₃)₂-phenyl | |
| 100 | 3,4-(CH₃)₂-phenyl | |
| 101 | 3,5-(CH₃)₂-phenyl | |
| 102 | 2,3,4-(CH₃)₃-phenyl | |
| 103 | 2,3,5-(CH₃)₃-phenyl | |
| 104 | 2,3,6-(CH₃)₃-phenyl | |
| 105 | 2,4,5-(CH₃)₃-phenyl | |
| 106 | 2,4,6-(CH₃)₃-phenyl | |
| 107 | 3,4,5-(CH₃)₃-phenyl | |
| 108 | 2,3,4,6-(CH₃)₄-phenyl | |
| 109 | 2,3,5,6-(CH₃)₄-phenyl | |
| 110 | (CH₃)₅-phenyl | |
| 111 | 2,4-(C₂H₅)₂-phenyl | |
| 112 | 2,6-(C₂H₅)₂-phenyl | |
| 113 | 3,5-(C₂H₅)₂-phenyl | |
| 114 | 2,4,6-(C₂H₅)₃-phenyl | |
| 115 | 2,4-(i-C₃H₇)₂-phenyl | |
| 116 | 2,6-(i-C₃H₇)₂-phenyl | |
| 117 | 3,5-(i-C₃H₇)₂-phenyl | |
| 118 | 2,4,6-(i-C₃H₇)₃-phenyl | |
| 119 | 2,3-(t-C₄H₉)₂-phenyl | |
| 120 | 2,4-(t-C₄H₉)₂-phenyl | |
| 121 | 2,5-(t-C₄H₉)₂-phenyl | |
| 122 | 2,6-(t-C₄H₉)₂-phenyl | |
| 123 | 3,5-(t-C₄H₉)₂-phenyl | |
| 124 | 2,4,6-(t-C₄H₉)₃-phenyl | |
| 125 | 2-t-C₄H₉, 4-CH₃-phenyl | |
| 126 | 2-t-C₄H₉, 5-CH₃-phenyl | |
| 127 | 2,6-(t-C₄H₉)₂, 4-CH₃-phenyl | |
| 128 | 2-CH₃, 4-t-C₄H₉-phenyl | |
| 129 | 2-CH₃, 6-t-C₄H₉-phenyl | |
| 130 | 2-CH₃, 4-i-C₃H₇-phenyl | |
| 131 | 2-CH₃, 5-i-C₃H₇-phenyl | |
| 132 | 3-CH₃, 4-i-C₃H₇-phenyl | |
| 133 | 2-i-C₃H₇, 5-CH₃-phenyl | |
| 134 | 2,4-(t-C₄H₉)₂-6-i-C₃H₇-phenyl | |
| 135 | 2-cyclo-C₆H₁₁-phenyl | |
| 136 | 3-cyclo-C₆H₁₁-phenyl | |
| 137 | 4-cyclo-C₆H₁₁-phenyl | |
| 138 | 2,4-(cyclo-C₆H₁₁)₂-6-CH₃-phenyl | |
| 139 | 2-CH₃, 4-cyclo-C₆H₁₁-phenyl | |
| 140 | 2-CH₂C₆H₅-phenyl | |
| 141 | 3-CH₂C₆H₅-phenyl | |
| 142 | 4-CH₂C₆H₅-phenyl | |
| 143 | 2-CH₂C₆H₅, 4-CH₃-phenyl | |
| 144 | 2-CH₃, 4-CH₂C₆H₅-phenyl | |
| 145 | 2-C₆H₅-phenyl | |
| 146 | 3-C₆H₅-phenyl | |
| 147 | 4-C₆H₅-phenyl | |
| 148 | 4-(2-i-C₃H₇—C₆H₄)-phenyl | |
| 149 | 4-C₆H₅, 2,6-(CH₃)₂-phenyl | |
| 150 | 2-Cl, 4-C₆H₅-phenyl | |
| 151 | 2-Br, 4-C₆H₅-phenyl | |
| 152 | 2-C₆H₅, 4-Cl-phenyl | |
| 153 | 2-C₆H₅, 4-Br-phenyl | |
| 154 | 2-CH₂C₆H₅, 4-Cl-phenyl | |
| 155 | 2-CH₂C₆H₅, 4-Br-phenyl | |
| 156 | 2-Cl, 4-CH₂C₆H₅-phenyl | |
| 157 | 2-Br, 4-CH₂C₆H₅-phenyl | |
| 158 | 2-cyclo-C₆H₁₁, 4-Cl-phenyl | |
| 159 | 2-cyclo-C₆H₁₁, 4-Br-phenyl | |
| 160 | 2-Cl, 4-cyclo-C₆H₁₁-phenyl | |
| 161 | 2-Br, 4-cyclo-C₆H₁₁-phenyl | |
| 162 | 3-OCH₃-phenyl | |
| 163 | 2,4-(OCH₃)₂-phenyl | |
| 164 | 2-CF₃-phenyl | |
| 165 | 3-CF₃-phenyl | |
| 166 | 4-CF₃-phenyl | |
| 167 | 2-NO₂-phenyl | |
| 168 | 3-NO₂-phenyl | |
| 169 | 4-NO₂-phenyl | |
| 170 | 2-CN-phenyl | |
| 171 | 3-CN-phenyl | |
| 172 | 4-CN-phenyl | |
| 173 | 2-CH₃, 3-Cl-phenyl | |
| 174 | 2-CH₃, 4-Cl-phenyl | |
| 175 | 2-CH₃, 5-Cl-phenyl | |
| 176 | 2-CH₃, 6-Cl-phenyl | |
| 177 | 2-CH₃, 3-F-phenyl | |
| 178 | 2-CH₃, 4-F-phenyl | |
| 179 | 2-CH₃, 5-F-phenyl | |
| 180 | 2-CH₃, 6-F-phenyl | |
| 181 | 2-CH₃, 3-Br-phenyl | |
| 182 | 2-CH₃, 4-Br-phenyl | |
| 183 | 2-CH₃, 5-Br-phenyl | |
| 184 | 2-CH₃, 6-Br-phenyl | |
| 185 | 2-Cl, 3-CH₃-phenyl | |
| 186 | 2-Cl, 4-CH₃-phenyl | |
| 187 | 2-Cl, 5-CH₃-phenyl | |
| 188 | 2-Cl, 3-i-C₃H₇ | |
| 189 | 2-F, 3-CH₃-phenyl | |
| 190 | 2-F, 4-CH₃-phenyl | |
| 191 | 2-F, 5-CH₃-phenyl | |
| 192 | 2-Br, 3-CH₃-phenyl | |
| 193 | 2-Br, 4-CH₃-phenyl | |
| 194 | 3-CH₃, 4-Cl-phenyl | |
| 195 | 3-CH₃, 5-Cl-phenyl | |
| 196 | 2-Br, 5-CH₃-phenyl | |
| 197 | 3-CH₃, 4-F-phenyl | |
| 198 | 3-CH₃, 5-F-phenyl | |
| 199 | 3-CH₃, 4-Br-phenyl | |
| 200 | 3-CH₃, 5-Br-phenyl | |
| 201 | 3-F, 4-CH₃-phenyl | |
| 202 | 3-Cl, 4-CH₃-phenyl | |
| 203 | 3-Br, 4-CH₃-phenyl | |
| 204 | 2-Cl, 4,5-(CH₃)₂-phenyl | |
| 205 | 2-Br, 4,5-(CH₃)₂-phenyl | |
| 206 | 2-Cl, 3,5-(CH₃)₂-phenyl | |
| 207 | 2-Br, 3,5-(CH₃)₂-phenyl | |
| 208 | 2,6-Cl₂, 4-CH₃-phenyl | |
| 209 | 2,6-F₂, 4-CH₃-phenyl | |
| 210 | 2,6-Br₂, 4-CH₃-phenyl | |
| 211 | 2,4-Cl₂, 6-CH₃-phenyl | |
| 212 | 2,4-F₂, 6-CH₃-phenyl | |
| 213 | 2,4-Br₂, 6-CH₃-phenyl | |
| 214 | 2,6-(CH₃)₂, 4-F-phenyl | |
| 215 | 2,6-(CH₃)₂, 4-Cl-phenyl | |
| 216 | 2,6-(CH₃)₂, 4-Br-phenyl | |
| 217 | 3,5-(CH₃)₂, 4-F-phenyl | |
| 218 | 3,5-(CH₃)₂, 4-Cl-phenyl | |
| 219 | 3,5-(CH₃)₂, 4-Br-phenyl | |
| 220 | 2,3,6-(CH₃)₃, 4-F-phenyl | |
| 221 | 2,3,6-(CH₃)₃, 4-Cl-phenyl | |
| 222 | 2,3,6-(CH₃)₃, 4-Br-phenyl | |

TABLE 2-continued

[Structure: phenyl ring with S—R substituent, and C(=O)—C(=N—OCH₃)—SCH₃ group]

| No. | R | mp(°C.)/IR(cm⁻¹) |
|---|---|---|
| 223 | 2,4-(CH₃)₂, 6-F-phenyl | |
| 224 | 2,4-(CH₃)₂, 6-Cl-phenyl | |
| 225 | 2,4-(CH₃)₂, 6-Br-phenyl | |
| 226 | 2-i-C₃H₇, 4-Cl, 5-CH₃-phenyl | |
| 227 | 2-Cl, 4-NO₂-phenyl | |
| 228 | 2-NO₂, 4-Cl-phenyl | |
| 229 | 2-OCH₃, 5-NO₂-phenyl | |
| 230 | 2,4-Cl₂, 5-NO₂-phenyl | |
| 231 | 2,4-Cl₂, 6-NO₂-phenyl | |
| 232 | 2,6-Cl₂, 4-NO₂-phenyl | |
| 233 | 2,6-Br₂, 4-NO₂-phenyl | |
| 234 | 2,6-I₂, 4-NO₂-phenyl | |
| 235 | 2-C₆H₅O-phenyl | |
| 236 | 3-C₆H₅O-phenyl | |
| 237 | 4-C₆H₅O-phenyl | |
| 238 | 3-t-C₄H₉O-phenyl | |
| 239 | 4-t-C₄H₉O-phenyl | |
| 240 | 1-naphthyl | |
| 241 | 2-naphthyl | |
| 242 | 2-pyridyl | |
| 243 | 6-methyl-2-pyridyl | |
| 244 | 6-ethyl-2-pyridyl | |
| 245 | 6-n-propyl-2-pyridyl | |
| 246 | 6-iso-propyl-2-pyridyl | |
| 247 | 6-n-butyl-2-pyridyl | |
| 248 | 6-tert.-butyl-2-pyridyl | |
| 249 | 6-n-pentyl-2-pyridyl | |
| 250 | 6-n-hexyl-2-pyridyl | |
| 251 | 6-phenyl-2-pyridyl | |
| 252 | 6-benzyl-2-pyridyl | |
| 253 | 6-trifluoromethyl-2-pyridyl | |
| 254 | 6-methoxy-2-pyridyl | |
| 255 | 6-chloro-2-pyridyl | |
| 256 | 3,6-dimethyl-2-pyridyl | |
| 257 | 3,6-diethyl-2-pyridyl | |
| 258 | 4,6-dimethyl-2-pyridyl | |
| 259 | 5,6-dimethyl-2-pyridyl | |
| 260 | 4-phenyl-6-methyl-2-pyridyl | |
| 261 | 4,6-diphenyl-2-pyridyl | |
| 262 | 3,4-dichloro-6-methyl-2-pyridyl | |
| 263 | 3,4,5-trichloro-6-phenyl-2-pyridyl | |
| 264 | 4-trifluoromethyl-6-methyl-2-pyridyl | |
| 265 | 3-cyano-6-methyl-2-pyridyl | |
| 266 | 3-cyano-6-ethyl-2-pyridyl | |
| 267 | 3-cyano-6-n-propyl-2-pyridyl | |
| 268 | 3-cyano-6-iso-propyl-2-pyridyl | |
| 269 | 3-cyano-6-cyclo-propyl-2-pyridyl | |
| 270 | 3-cyano-6-n-butyl-2-pyridyl | |
| 271 | 3-cyano-6-tert.-butyl-2-pyridyl | |
| 272 | 3-cyano-6-cyclo-hexyl-2-pyridyl | |
| 273 | 3-cyano-6-phenyl-2-pyridyl | |
| 274 | 3-cyano-4,6-dimethyl-2-pyridyl | |
| 275 | 3,5,6-trichloro-2-pyridyl | |
| 276 | 5-trifluoromethyl-2-pyridyl | |
| 277 | 3-chloro-5-trifluoromethyl-2-pyridyl | |
| 278 | 2-quinolyl | |
| 279 | 3-methyl-2-quinolyl | |
| 280 | 4-methyl-2-quinolyl | |
| 281 | 4-ethyl-2-quinolyl | |
| 282 | 4-phenyl-2-quinolyl | |
| 283 | 6-methyl-2-quinolyl | |
| 284 | 6-chloro-2-quinolyl | |
| 285 | 8-methyl-2-quinolyl | |
| 286 | 8-chloro-2-quinolyl | |
| 287 | 3,4-dimethyl-2-quinolyl | |
| 288 | 4-methyl-8-methoxy-2-quinolyl | |
| 289 | 4-phenyl-8-ethoxy-2-quinolyl | |
| 290 | 4-methyl-8-chloro-2-quinolyl | |
| 291 | 4-methyl-8-fluoro-2-quinolyl | |
| 292 | 4-quinolyl | |
| 293 | 2-methyl-4-quinolyl | |
| 294 | 2-trifluoromethyl-4-quinolyl | |
| 295 | 2-iso-propyl-4-quinolyl | |
| 296 | 2-n-pentyl-4-quinolyl | |
| 297 | 2-phenyl-4-quinolyl | |
| 298 | 2,6-dimethyl-4-quinolyl | |
| 299 | 2-methyl-6-chloro-4-quinolyl | |
| 300 | 2-methyl-6-fluoro-4-quinolyl | |
| 301 | 8-quinolyl | |
| 302 | 2-methyl-8-quinolyl | |
| 303 | 5,7-dichloro-8-quinolyl | |
| 304 | 4,6-dimethyl-2-pyrimidinyl | |
| 305 | 4-trifluoromethyl-2-pyrimidinyl | |
| 306 | 4,5,6-trimethyl-2-pyrimidinyl | |
| 307 | 4-benzyl-6-methyl-2-pyrimidinyl | |
| 308 | 4-methyl-6-phenyl-2-pyrimidinyl | |
| 309 | 4,6-dimethyl-5-chloro-2-pyrimidinyl | |
| 310 | 2,6-dimethyl-4-pyrimidinyl | |
| 311 | 2,6-bis-(trifluoromethyl)-4-pyrimidinyl | |
| 312 | 2-iso-propyl-6-methyl-4-pyrimidinyl | |
| 313 | 2-cyclo-propyl-6-methyl-4-pyrimidinyl | |
| 314 | 2-methyl-6-methoxymethyl-4-pyrimidinyl | |
| 315 | 2-iso-propyl-6-methoxymethyl-4-pyrimidinyl | |
| 316 | 2-phenyl-4-pyrimidinyl | |
| 317 | 3,5-dimethyl-4-pyrimidinyl | |
| 318 | 2-methyl-6-trifluoromethyl-4-pyrimidinyl | |
| 319 | 2-n-propyl-6-trifluoromethyl-4-pyrimidinyl | |
| 320 | 2-iso-propyl-6-trifluoromethyl-4-pyrimidinyl | |
| 321 | 2-methyl-5-chloro-6-trifluoromethyl-4-pyrimidinyl | |
| 322 | 2-n-propyl-5-chloro-6-trifluoromethyl-4-pyrimidinyl | |
| 323 | 2-iso-propyl-5-chloro-6-trifluoromethyl-4-pyrimidinyl | |
| 324 | 2-tert.-butyl-5-chloro-6-trifluoromethyl-4-pyrimidinyl | |
| 325 | 6-EtO-benzothiazol-2-yl | |
| 326 | benzoxazol-2-yl | |
| 327 | 1-Me-imidazol-2-yl | |
| 328 | 4-but-1H-imidazol-2-yl | |
| 329 | 2-thiazolin-2-yl | |
| 330 | 5-CF₃-benzimidazol-2-yl | |
| 331 | 1-Ph-tetrazol-5-yl | |
| 332 | 5-CF₃-benzothiazol-2-yl | |
| 333 | 4,4-Me₂-5-methylene-2-thiazolin-2-yl | |
| 334 | 6-Cl-4-Me-benzothiazol-2-yl | |
| 335 | 5-Me-benzothiazol-2-yl | |
| 336 | 4-Cl-benzothiazol-2-yl | |
| 337 | 1-(3-NO₂—Ph)tetrazol-5-yl | |
| 338 | 2-thienyl | |
| 339 | 5-Me-benzoxazol-2-yl | |
| 340 | 7-Cl-benzothiazol-2-yl | |
| 341 | 5,6-Cl₃-1H-benzimidazol-2-yl | |
| 342 | 5-Cl-benzoxazol-2-yl | |
| 343 | 6-Cl-benzothiazol-2-yl | |
| 344 | 2-Ph-thiazol-2-yl | |
| 345 | 3-CN-4,6-Me₂-2-pyridyl | |
| 346 | 1-Ph-1,2,4-triazol-3-yl | |
| 347 | 1-Pri-benzimidazol-2-yl | |
| 348 | 5-Br-benzothiazol-2-yl | |
| 349 | 5-Br-1H-benzimidazol-2-yl | |
| 350 | 7-Cl-4-MeO-benzothiazol-2-yl | |
| 351 | 1H-benzimidazol-2-yl | |

TABLE 2-continued

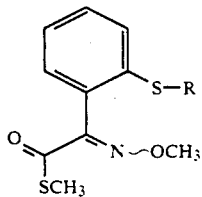

| No. | R | mp(°C.)/IR(cm$^{-1}$) |
|---|---|---|
| 352 | 5-Cl-benzothiazol-2-yl | |
| 353 | 5-NO$_2$-benzoxazol-2-yl | |
| 354 | 5-t-Bu-benzoxazol-2-yl | |
| 355 | 4,6,7-Cl$_3$-benzothiozol-2-yl | |
| 356 | 5-Ph-thiazol-2-yl | |
| 357 | 5,7-Me$_2$-benzoxazol-2-yl | |
| 358 | 6-Me-benzoxazol-2-yl | |
| 359 | 1,2,4-triazin-3-yl | |

TABLE 2-continued

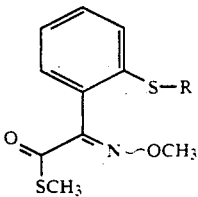

| No. | R | mp(°C.)/IR(cm$^{-1}$) |
|---|---|---|
| 360 | 6-Pr-benzothiazol-2-yl | |
| 361 | 6-PhO-benzothiazol-2-yl | |
| 362 | 4-(4-Cl—Ph)-thiazol-2-yl | |
| 363 | 4-(4-Me—Ph)-thiazol-2-yl | |
| 364 | 5-Me-4-Ph-thiazol-2-yl | |
| 365 | 5-Cl-1-H-benzimidazol-2-yl | |
| 366 | 5-Ph-1,2,4-triazol-3-yl | |
| 367 | 3-Ph-1,2,4-thiadiazol-5-yl | |

TABLE 3

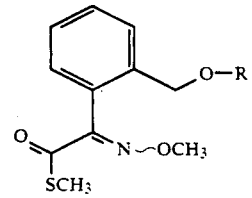

| No. | R | mp(°C.)/IR(cm$^{-1}$) |
|---|---|---|
| 1 | methyl | |
| 2 | ethyl | |
| 3 | n-propyl | |
| 4 | iso-propyl | |
| 5 | n-butyl | |
| 6 | s-butyl | |
| 7 | iso-butyl | |
| 8 | tert.-butyl | |
| 9 | pentyl | |
| 10 | hexyl | |
| 11 | phenyl | 1663, 1598, 1587, 1496, 1242, 1221, 1026, 845, 756, 691 |
| 12 | 2-F-phenyl | |
| 13 | 3-F-phenyl | |
| 14 | 4-F-phenyl | |
| 15 | 2-Cl-phenyl | 58–60° C. |
| 16 | 3-Cl-phenyl | |
| 17 | 4-Cl-phenyl | |
| 18 | 2-Br-phenyl | |
| 19 | 3-Br-phenyl | |
| 20 | 4-Br-phenyl | |
| 21 | 2-I-phenyl | |
| 22 | 3-I-phenyl | |
| 23 | 4-I-phenyl | |
| 24 | 2-CH$_3$-phenyl | 1662, 1494, 1461, 1240, 1190, 1122, 1051, 1025, 845, 753 (cm$^{-1}$) |
| 25 | 2-CN-phenyl | |
| 26 | 3-CN-phenyl | |
| 27 | 4-CN-phenyl | |
| 28 | 2,3-F$_2$-phenyl | |
| 29 | 2,4-F$_2$-phenyl | |
| 30 | 2,3-Cl$_2$-phenyl | |
| 31 | 2,4-Cl$_2$-phenyl | |
| 32 | 2,5-Cl$_2$-phenyl | |
| 33 | 2,6-Cl$_2$-phenyl | |
| 34 | 3,4-Cl$_2$-phenyl | |
| 35 | 3,5-Cl$_2$-phenyl | |
| 36 | 2,4-Br$_2$-phenyl | |
| 37 | 2,5-Br$_2$-phenyl | |
| 38 | 2,6-Br$_2$-phenyl | |
| 39 | 2,4-I$_2$-phenyl | |
| 40 | 2-Cl, 3-F-phenyl | |
| 41 | 2-Cl, 4-F-phenyl | |
| 42 | 2-Cl, 5-F-phenyl | |
| 43 | 2-Cl, 6-F-phenyl | |

TABLE 3-continued

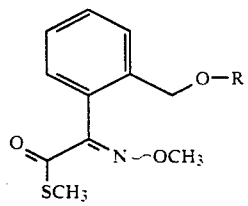

| No. | R | mp(°C.)/IR(cm$^{-1}$) |
|---|---|---|
| 44 | 2-Cl, 3-Br-phenyl | |
| 45 | 2-Cl, 4-Br-phenyl | |
| 46 | 2-Cl, 5-Br-phenyl | |
| 47 | 2-Cl, 6-Br-phenyl | |
| 48 | 2-Br, 3-Cl-phenyl | |
| 49 | 2-Br, 4-Cl-phenyl | |
| 50 | 2-Br, 3-F-phenyl | |
| 51 | 2-Br, 4-F-phenyl | |
| 52 | 2-Br, 5-F-phenyl | |
| 53 | 2-Br, 6-F-phenyl | |
| 54 | 2-F, 3-Cl-phenyl | |
| 55 | 2-F, 4-Cl-phenyl | |
| 56 | 2-F, 5-Cl-phenyl | |
| 57 | 3-Cl, 4-F-phenyl | |
| 58 | 3-Cl, 5-F-phenyl | |
| 59 | 3-Cl, 4-Br-phenyl | |
| 60 | 3-Cl, 5-Br-phenyl | |
| 61 | 3-F, 4-Cl-phenyl | |
| 62 | 3-F, 4-Br-phenyl | |
| 63 | 3-Br, 4-Cl-phenyl | |
| 64 | 3-Br, 4-F-phenyl | |
| 65 | 2,4,6-F$_3$-phenyl | |
| 66 | 2,3,4,-Cl$_3$-phenyl | |
| 67 | 2,3,5-Cl$_3$-phenyl | |
| 68 | 2,3,6-Cl$_3$-phenyl | |
| 69 | 2,4,5-Cl$_3$-phenyl | |
| 70 | 2,4,6-Cl$_3$-phenyl | |
| 71 | 3,4,5-Cl$_3$-phenyl | |
| 72 | 2,4,6-Br$_3$-phenyl | |
| 73 | 2,6-Cl$_2$-4-Br-phenyl | |
| 74 | 2,3,4,6-Cl$_4$-phenyl | |
| 75 | 2,3,5,6-Cl$_4$-phenyl | |
| 76 | F$_5$-phenyl | |
| 77 | Cl$_5$-phenyl | |
| 78 | Br$_5$-phenyl | |
| 79 | 2-CH$_3$-phenyl | |
| 80 | 3-CH$_3$-phenyl | |
| 81 | 4-CH$_3$-phenyl | |
| 82 | 2-C$_2$H$_5$-phenyl | |
| 83 | 3-C$_2$H$_5$-phenyl | |
| 84 | 4-C$_2$H$_5$-phenyl | |
| 85 | 2-n-C$_3$H$_7$-phenyl | |
| 86 | 3-n-C$_3$H$_7$-phenyl | |
| 87 | 4-n-C$_3$H$_7$-phenyl | |
| 88 | 2-i-C$_3$H$_7$-phenyl | |
| 89 | 3-i-C$_3$H$_7$-phenyl | |
| 90 | 4-i-C$_3$H$_7$-phenyl | |
| 91 | 2-s-C$_4$H$_9$-phenyl | |
| 92 | 3-s-C$_4$H$_9$-phenyl | |
| 93 | 4-s-C$_4$H$_9$-phenyl | |
| 94 | 2-t-C$_4$H$_9$-phenyl | |
| 95 | 3-t-C$_4$H$_9$-phenyl | |
| 96 | 4-t-C$_4$H$_9$-phenyl | |
| 97 | 2,3-(CH$_3$)$_2$-phenyl | |
| 98 | 2,4-(CH$_3$)$_2$-phenyl | |
| 99 | 2,5-(CH$_3$)$_2$-phenyl | |
| 100 | 2,6-(CH$_3$)$_2$-phenyl | |
| 101 | 3,4-(CH$_3$)$_2$-phenyl | |
| 102 | 3,5-(CH$_3$)$_2$-phenyl | |
| 103 | 2,3,4-(CH$_3$)$_3$-phenyl | |
| 104 | 2,3,5-(CH$_3$)$_3$-phenyl | |
| 105 | 2,3,6-(CH$_3$)$_3$-phenyl | |
| 106 | 2,4,5-(CH$_3$)$_3$-phenyl | |
| 107 | 2,4,6-(CH$_3$)$_3$-phenyl | |
| 108 | 3,4,5-(CH$_3$)$_3$-phenyl | |
| 109 | 2,3,4,6-(CH$_3$)$_4$-phenyl | |
| 110 | 2,3,5,6-(CH$_3$)$_4$-phenyl | |
| 111 | (CH$_3$)$_5$-phenyl | |
| 112 | 2,4-(C$_2$H$_5$)$_2$-phenyl | |
| 113 | 2,6-(C$_2$H$_5$)$_2$-phenyl | |

TABLE 3-continued

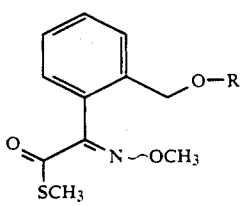

| No. | R | mp(°C.)/IR(cm$^{-1}$) |
|---|---|---|
| 114 | 3,5-(C$_2$H$_5$)$_2$-phenyl | |
| 115 | 2,4,6-(C$_2$H$_5$)$_3$-phenyl | |
| 116 | 2,4-(i-C$_3$H$_7$)$_2$-phenyl | |
| 117 | 2,6-(i-C$_3$H$_7$)$_2$-phenyl | |
| 118 | 3,5-(i-C$_3$H$_7$)$_2$-phenyl | |
| 119 | 2,4,6-(i-C$_3$H$_7$)$_3$-phenyl | |
| 120 | 2,3-(t-C$_4$H$_9$)$_2$-phenyl | |
| 121 | 2,4-(t-C$_4$H$_9$)$_2$-phenyl | |
| 122 | 2,5-(t-C$_4$H$_9$)$_2$-phenyl | |
| 123 | 2,6-(t-C$_4$H$_9$)$_2$-phenyl | |
| 124 | 3,5-(t-C$_4$H$_9$)$_2$-phenyl | |
| 125 | 2,4,6-(t-C$_4$H$_9$)$_3$-phenyl | |
| 126 | 2-t-C$_4$H$_9$, 4-CH$_3$-phenyl | |
| 127 | 2-t-C$_4$H$_9$, 5-CH$_3$-phenyl | |
| 128 | 2,6-(t-C$_4$H$_9$)$_2$, 4-CH$_3$-phenyl | |
| 129 | 2-CH$_3$, 4-t-C$_4$H$_9$-phenyl | |
| 130 | 2-CH$_3$, 6-t-C$_4$H$_9$-phenyl | |
| 131 | 1-CH$_3$, 4-i-C$_3$H$_7$-phenyl | |
| 132 | 2-CH$_3$, 5-i-C$_3$H$_7$-phenyl | |
| 133 | 3-CH$_3$, 4-i-C$_3$H$_7$-phenyl | |
| 134 | 2-i-C$_3$H$_7$, 5-CH$_3$-phenyl | |
| 135 | 2,4-(t-C$_4$H$_9$)$_2$-6-i-C$_3$H$_7$-phenyl | |
| 136 | 2-cyclo-C$_6$H$_{11}$-phenyl | |
| 137 | 3-cyclo-C$_6$H$_{11}$-phenyl | |
| 138 | 4-cyclo-C$_6$H$_{11}$-phenyl | |
| 139 | 2,4-(cyclo-C$_6$H$_{11}$)$_2$-6-CH$_3$-phenyl | |
| 140 | 2-CH$_3$, 4-cyclo-C$_6$H$_{11}$-phenyl | |
| 141 | 2-CH$_2$C$_6$H$_5$-phenyl | |
| 142 | 3-CH$_2$C$_6$H$_5$-phenyl | |
| 143 | 4-CH$_2$C$_6$H$_5$-phenyl | |
| 144 | 2-CH$_2$C$_6$H$_5$, 4-CH$_3$-phenyl | |
| 145 | 2-CH$_3$, 4-CH$_2$C$_6$H$_5$-phenyl | |
| 146 | 2-C$_6$H$_5$-phenyl | |
| 147 | 3-C$_6$H$_5$-phenyl | |
| 148 | 4-C$_6$H$_5$-phenyl | |
| 149 | 4-(2-i-C$_3$H$_7$—C$_6$H$_4$)-phenyl | |
| 150 | 4-C$_6$H$_5$, 2,6-(CH$_3$)$_2$-phenyl | |
| 151 | 2-Cl, 4-C$_6$H$_5$-phenyl | |
| 152 | 2-Br, 4-C$_6$H$_5$-phenyl | |
| 153 | 2-C$_6$H$_5$, 4-Cl-phenyl | |
| 154 | 2-C$_6$H$_5$, 4-Br-phenyl | |
| 155 | 2-CH$_2$C$_6$H$_5$, 4-Cl-phenyl | |
| 156 | 2-CH$_2$C$_6$H$_5$, 4-Br-phenyl | |
| 157 | 2-Cl, 4-CH$_2$C$_6$H$_5$-phenyl | |
| 158 | 2-Br, 4-CH$_2$C$_6$H$_5$-phenyl | |
| 159 | 2-cyclo-C$_6$H$_{11}$, 4-Cl-phenyl | |
| 160 | 2-cyclo-C$_6$H$_{11}$, 4-Br-phenyl | |
| 161 | 2-Cl, 4-cyclo-C$_6$H$_{11}$-phenyl | |
| 162 | 2-Br, 4-cyclo-C$_6$H$_{11}$-phenyl | |
| 163 | 3-OCH$_3$-phenyl | |
| 164 | 2,4-(OCH$_3$)$_2$-phenyl | |
| 165 | 2-CF$_3$-phenyl | |
| 166 | 3-CF$_3$-phenyl | |
| 167 | 4-CF$_3$-phenyl | |
| 168 | 2-NO$_2$-phenyl | |
| 169 | 3-NO$_2$-phenyl | |
| 170 | 4-NO$_2$-phenyl | |
| 171 | 2-CN-phenyl | |
| 172 | 3-CN-phenyl | |
| 173 | 4-CN-phenyl | |
| 174 | 2-CH$_3$, 3-Cl-phenyl | |
| 175 | 2-CH$_3$, 4-Cl-phenyl | |
| 176 | 2-CH$_3$, 5-Cl-phenyl | |
| 177 | 2-CH$_3$, 6-Cl-phenyl | |
| 178 | 2-CH$_3$, 3-F-phenyl | |
| 179 | 2-CH$_3$, 4-F-phenyl | |
| 180 | 2-CH$_3$, 5-F-phenyl | |
| 181 | 2-CH$_3$, 6-F-phenyl | |
| 182 | 2-CH$_3$, 3-Br-phenyl | |
| 183 | 2-CH$_3$, 4-Br-phenyl | |

TABLE 3-continued

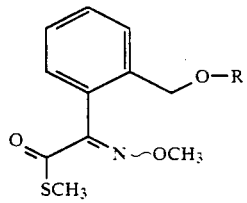

| No. | R | mp(°C.)/IR(cm$^{-1}$) |
|---|---|---|
| 184 | 2-CH$_3$, 5-Br-phenyl | |
| 185 | 2-CH$_3$, 6-Br-phenyl | |
| 186 | 2-Cl, 3-CH$_3$-phenyl | |
| 187 | 2-Cl, 4-CH$_3$-phenyl | |
| 188 | 2-Cl, 5-CH$_3$-phenyl | |
| 189 | 2-Cl, 3-i-C$_3$H$_7$ | |
| 190 | 2-F, 3-CH$_3$-phenyl | |
| 191 | 2-F, 4-CH$_3$-phenyl | |
| 192 | 2-F, 5-CH$_3$-phenyl | |
| 193 | 2-Br, 3-CH$_3$-phenyl | |
| 194 | 2-Br, 4-CH$_3$-phenyl | |
| 195 | 3-CH$_3$, 4-Cl-phenyl | |
| 196 | 3-CH$_3$, 5-Cl-phenyl | |
| 197 | 2-Br, 5-CH$_3$-phenyl | |
| 198 | 3-CH$_3$, 4-F-phenyl | |
| 199 | 3-CH$_3$, 5-F-phenyl | |
| 200 | 3-CH$_3$, 4-Br-phenyl | |
| 201 | 3-CH$_3$, 5-Br-phenyl | |
| 202 | 3-F, 4-CH$_3$-phenyl | |
| 203 | 3-Cl, 4-CH$_3$-phenyl | |
| 204 | 3-Br, 4-CH$_3$-phenyl | |
| 205 | 2-Cl, 4,5-(CH$_3$)$_2$-phenyl | |
| 206 | 2-Br, 4,5-(CH$_3$)$_2$-phenyl | |
| 207 | 2-Cl, 3,5-(CH$_3$)$_2$-phenyl | |
| 208 | 2-Br, 3,5-(CH$_3$)$_2$-phenyl | |
| 209 | 2,6-Cl$_2$, 4-CH$_3$-phenyl | |
| 210 | 2,6-F$_2$, 4-CH$_3$-phenyl | |
| 211 | 2,6-Br$_2$, 4-CH$_3$-phenyl | |
| 212 | 2,4-Cl$_2$, 6-CH$_3$-phenyl | |
| 213 | 2,4-F$_2$, 6-CH$_3$-phenyl | |
| 214 | 2,4-Br$_2$, 6-CH$_3$-phenyl | |
| 215 | 2,6-(CH$_3$)$_2$, 4-F-phenyl | |
| 216 | 2,6-(CH$_3$)$_2$, 4-Cl-phenyl | |
| 217 | 2,6-(CH$_3$)$_2$, 4-Br-phenyl | |
| 218 | 3,5-(CH$_3$)$_2$, 4-F-phenyl | |
| 219 | 3,5-(CH$_3$)$_2$, 4-Cl-phenyl | |
| 220 | 3,5-(CH$_3$)$_2$, 4-Br-phenyl | |
| 221 | 2,3,6-(CH$_3$)$_3$, 4-F-phenyl | |
| 222 | 2,3,6-(CH$_3$)$_3$, 4-Cl-phenyl | |
| 223 | 2,3,6-(CH$_3$)$_3$, 4-Br-phenyl | |
| 224 | 2,4-(CH$_3$)$_2$, 6-F-phenyl | |
| 225 | 2,4-(CH$_3$)$_2$, 6-Cl-phenyl | |
| 226 | 2,4-(CH$_3$)$_2$, 6-Br-phenyl | |
| 227 | 2-i-C$_3$H$_7$, 4-Cl, 5-CH$_3$-phenyl | |
| 228 | 2-Cl, 4-NO$_2$-phenyl | |
| 229 | 2-NO$_2$, 4-Cl-phenyl | |
| 230 | 2-OCH$_3$, 5-NO$_2$-phenyl | |
| 231 | 2,4-Cl$_2$, 5-NO$_2$-phenyl | |
| 232 | 2,4-Cl$_2$, 6-NO$_2$-phenyl | |
| 233 | 2,6-Cl$_2$, 4-NO$_2$-phenyl | |
| 234 | 2,6-Br$_2$, 4-NO$_2$-phenyl | |
| 235 | 2,6-I$_2$, 4-NO$_2$-phenyl | |
| 236 | 2-C$_6$H$_5$O-phenyl | |
| 237 | 3-C$_6$H$_5$O-phenyl | |
| 238 | 4-C$_6$H$_5$O-phenyl | |
| 239 | 3-t-C$_4$H$_9$O-phenyl | |
| 240 | 4-t-C$_4$H$_9$O-phenyl | |
| 241 | 1-naphthyl | |
| 242 | 2-naphthyl | |
| 243 | 2-pyridyl | |
| 244 | 6-methyl-2-pyridyl | |
| 245 | 6-ethyl-2-pyridyl | |
| 246 | 6-n-propyl-2-pyridyl | |
| 247 | 6-iso-propyl-2-pyridyl | |
| 248 | 6-n-butyl-2-pyridyl | |
| 249 | 6-tert.-butyl-2-pyridyl | |
| 250 | 6-n-pentyl-2-pyridyl | |
| 251 | 6-n-hexyl-2-pyridyl | |
| 252 | 6-phenyl-2-pyridyl | |
| 253 | 6-benzyl-2-pyridyl | |

TABLE 3-continued

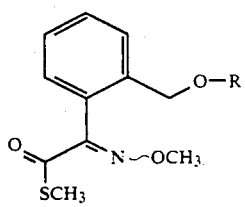

| No. | R | mp(°C.)/IR(cm$^{-1}$) |
|---|---|---|
| 254 | 6-trifluoromethyl-2-pyridyl | |
| 255 | 6-methoxy-2-pyridyl | |
| 256 | 6-chloro-2-pyridyl | |
| 257 | 3,6-dimethyl-2-pyridyl | |
| 258 | 3,6-diethyl-2-pyridyl | |
| 259 | 4,6-dimethyl-2-pyridyl | |
| 260 | 5,6-dimethyl-2-pyridyl | |
| 261 | 4-phenyl-6-methyl-2-pyridyl | |
| 262 | 4,6-diphenyl-2-pyridyl | |
| 263 | 3,4-dichloro-6-methyl-2-pyridyl | |
| 264 | 3,4,5-trichloro-6-phenyl-2-pyridyl | |
| 265 | 4-trifluoromethyl-6-methyl-2-pyridyl | |
| 266 | 3-cyano-6-methyl-2-pyridyl | |
| 267 | 3-cyano-6-ethyl-2-pyridyl | |
| 268 | 3-cyano-6-n-propyl-2-pyridyl | |
| 269 | 3-cyano-6-iso-propyl-2-pyridyl | |
| 270 | 3-cyano-6-cyclo-propyl-2-pyridyl | |
| 271 | 3-cyano-6-n-butyl-2-pyridyl | |
| 272 | 3-cyano-6-tert.-butyl-2-pyridyl | |
| 273 | 3-cyano-6-cyclo-hexyl-2-pyridyl | |
| 274 | 3-cyano-6-phenyl-2-pyridyl | |
| 275 | 3-cyano-4,6-dimethyl-2-pyridyl | |
| 276 | 3,5,6-trichloro-2-pyridyl | |
| 277 | 5-trifluoromethyl-2-pyridyl | |
| 278 | 3-chloro-5-trifluoromethyl-2-pyridyl | |
| 279 | 2-quinolyl | |
| 280 | 3-methyl-2-quinolyl | |
| 281 | 4-methyl-2-quinolyl | |
| 282 | 4-ethyl-2-quinolyl | |
| 283 | 4-phenyl-2-quinolyl | |
| 284 | 6-methyl-2-quinolyl | |
| 285 | 6-chloro-2-quinolyl | |
| 286 | 8-methyl-2-quinolyl | |
| 287 | 8-chloro-2-quinolyl | |
| 288 | 3,4-dimethyl-2-quinolyl | |
| 289 | 4-methyl-8-methoxy-2-quinolyl | |
| 290 | 4-phenyl-8-ethoxy-2-quinolyl | |
| 291 | 4-methyl-8-chloro-2-quinolyl | |
| 292 | 4-methyl-8-fluoro-2-quinolyl | |
| 293 | 4-quinolyl | |
| 294 | 2-methyl-4-quinolyl | |
| 295 | 2-trifluoromethyl-4-quinolyl | |
| 296 | 2-iso-propyl-4-quinolyl | |
| 297 | 2-n-pentyl-4-quinolyl | |
| 298 | 2-phenyl-4-quinolyl | |
| 299 | 2,6-dimethyl-4-quinolyl | |
| 300 | 2-methyl-6-chloro-4-quinolyl | |
| 301 | 2-methyl-6-fluoro-4-quinolyl | |
| 302 | 8-quinolyl | |
| 303 | 2-methyl-8-quinolyl | |
| 304 | 5,7-dichloro-8-quinolyl | |
| 305 | 4,6-dimethyl-2-pyrimidinyl | |
| 306 | 4-trifluoromethyl-2-pyrimidinyl | |
| 307 | 4,5,6-trimethyl-2-pyrimidinyl | |
| 308 | 4-benzyl-6-methyl-2-pyrimidinyl | |
| 309 | 4-methyl-6-phenyl-2-pyrimidinyl | |
| 310 | 4,6-dimethyl-5-chloro-2-pyrimidinyl | |
| 311 | 2,6-dimethyl-4-pyrimidinyl | |
| 312 | 2,6-bis-(trifluoromethyl)-4-pyrimidinyl | |
| 313 | 2-iso-propyl-6-methyl-4-pyrimidinyl | |
| 314 | 2-cyclo-propyl-6-methyl-4-pyrimidinyl | |
| 315 | 2-methyl-6-methoxymethyl-4-pyrimidinyl | |
| 316 | 2-iso-propyl-6-methoxymethyl-4-pyrimidinyl | |
| 317 | 2-phenyl-4-pyrimidinyl | |
| 318 | 3,5-dimethyl-4-pyrimidinyl | |
| 319 | 2-methyl-6-trifluoromethyl-4-pyrimidinyl | |
| 320 | 2-n-propyl-6-trifluoromethyl-4-pyrimidinyl | |
| 321 | 2-iso-propyl-6-trifluoromethyl-4-pyrimidinyl | |
| 322 | 2-methyl-5-chloro-6-trifluoromethyl-4-pyrimidinyl | |
| 323 | 2-n-propyl-5-chloro-6-trifluoromethyl-4-pyrimidinyl | |

TABLE 3-continued

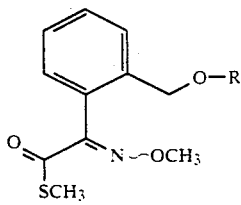

| No. | R |
|---|---|
| 324 | 2-iso-propyl-5-chloro-6-trifluoromethyl-4-pyrimidinyl |
| 325 | 2-tert.-butyl-5-chloro-6-trifluoromethyl-4-pyrimidinyl |

TABLE 4

| No. | R | mp (°C.)/IR (cm$^{-1}$) |
|---|---|---|
| 1 | methyl | |
| 2 | ethyl | |
| 3 | n-propyl | |
| 4 | iso-propyl | |
| 5 | n-butyl | |
| 6 | s-butyl | |
| 7 | iso-butyl | |
| 8 | tert.-butyl | |
| 9 | pentyl | |
| 10 | hexyl | |
| 11 | phenyl | |
| 12 | 2-F-phenyl | |
| 13 | 3-F-phenyl | |
| 14 | 4-F-phenyl | |
| 15 | 2-Cl-phenyl | 1661, 1451, 1443, 1139, 1115, 1043, 1035, 1024, 846, 749 |
| 16 | 3-Cl-phenyl | |
| 17 | 4-Cl-phenyl | |
| 18 | 2-Br-phenyl | |
| 19 | 3-Br-phenyl | |
| 20 | 4-Br-phenyl | |
| 21 | 2-I-phenyl | |
| 22 | 3-I-phenyl | |
| 23 | 4-I-phenyl | |
| 24 | 2-CN-phenyl | |
| 25 | 3-CN-phenyl | |
| 26 | 4-CN-phenyl | |
| 27 | 2,3-F$_2$-phenyl | |
| 28 | 2,4-F$_2$-phenyl | |
| 29 | 2,3-Cl$_2$-phenyl | |
| 30 | 2,4-Cl$_2$-phenyl | |
| 31 | 2,5-Cl$_2$-phenyl | |
| 32 | 2,6-Cl$_2$-phenyl | |
| 33 | 3,4-Cl$_2$-phenyl | |
| 34 | 3,5-Cl$_2$-phenyl | |
| 35 | 2,4-Br$_2$-phenyl | |
| 36 | 2,5-Br$_2$-phenyl | |
| 37 | 2,6-Br$_2$-phenyl | |
| 38 | 2,4-I$_2$-phenyl | |
| 39 | 2-Cl, 3-F-phenyl | |
| 40 | 2-Cl, 4-F-phenyl | |
| 41 | 2-Cl, 5-F-phenyl | |
| 42 | 2-Cl, 6-F-phenyl | |
| 43 | 2-Cl, 3-Br-phenyl | |
| 44 | 2-Cl, 4-Br-phenyl | |
| 45 | 2-Cl, 5-Br-phenyl | |
| 46 | 2-Cl, 6-Br-phenyl | |
| 47 | 2-Br, 3-Cl-phenyl | |
| 48 | 2-Br, 4-Cl-phenyl | |
| 49 | 2-Br, 3-F-phenyl | |
| 50 | 2-Br, 4-F-phenyl | |
| 51 | 2-Br, 5-F-phenyl | |
| 52 | 2-Br, 6-F-phenyl | |
| 53 | 2-F, 3-Cl-phenyl | |
| 54 | 2-F, 4-Cl-phenyl | |
| 55 | 2-F, 5-Cl-phenyl | |
| 56 | 3-Cl, 4-F-phenyl | |
| 57 | 3-Cl, 5-F-phenyl | |
| 58 | 3-Cl, 4-Br-phenyl | |
| 59 | 3-Cl, 5-Br-phenyl | |
| 60 | 3-F, 4-Cl-phenyl | |
| 61 | 3-F, 4-Br-phenyl | |
| 62 | 3-Br, 4-Cl-phenyl | |
| 63 | 3-Br, 4-F-phenyl | |
| 64 | 2,4,6-F$_3$-phenyl | |
| 65 | 2,3,4,-Cl$_3$-phenyl | |
| 66 | 2,3,5-Cl$_3$-phenyl | |
| 67 | 2,3,6-Cl$_3$-phenyl | |
| 68 | 2,4,5-Cl$_3$-phenyl | |
| 69 | 2,4,6-Cl$_3$-phenyl | |
| 70 | 3,4,5-Cl$_3$-phenyl | |
| 71 | 2,4,6-Br$_3$-phenyl | |
| 72 | 2,6-Cl$_2$-4-Br-phenyl | |
| 73 | 2,3,4,6-Cl$_4$-phenyl | |
| 74 | 2,3,5,6-Cl$_4$-phenyl | |
| 75 | F$_5$-phenyl | |
| 76 | Cl$_5$-phenyl | |
| 77 | Br$_5$-phenyl | |
| 78 | 2-CH$_3$-phenyl | |
| 79 | 3-CH$_3$-phenyl | |
| 80 | 4-CH$_3$-phenyl | |
| 81 | 2-C$_2$H$_5$-phenyl | |
| 82 | 3-C$_2$H$_5$-phenyl | |
| 83 | 4-C$_2$H$_5$-phenyl | |
| 84 | 2-n-C$_3$H$_7$-phenyl | |
| 85 | 3-n-C$_3$H$_7$-phenyl | |
| 86 | 4-n-C$_3$H$_7$-phenyl | |
| 87 | 2-i-C$_3$H$_7$-phenyl | |
| 88 | 3-i-C$_3$H$_7$-phenyl | |
| 89 | 4-i-C$_3$H$_7$-phenyl | |
| 90 | 2-s-C$_4$H$_9$-phenyl | |
| 91 | 3-s-C$_4$H$_9$-phenyl | |
| 92 | 4-s-C$_4$H$_9$-phenyl | |
| 93 | 2-t-C$_4$H$_9$-phenyl | |
| 94 | 3-t-C$_4$H$_9$-phenyl | |
| 95 | 4-t-C$_4$H$_9$-phenyl | |
| 96 | 2,3-(CH$_3$)$_2$-phenyl | |
| 97 | 2,4-(CH$_3$)$_2$-phenyl | |
| 98 | 2,5-(CH$_3$)$_2$-phenyl | |
| 99 | 2,6-(CH$_3$)$_2$-phenyl | |
| 100 | 3,4-(CH$_3$)$_2$-phenyl | |

TABLE 4-continued

Structure: 2-(CH₂-S-R)-phenyl group attached to C(=NOCH₃)-C(=O)-SCH₃

| No. | R | mp (°C.)/IR (cm⁻¹) |
|---|---|---|
| 101 | 3,5-(CH₃)₂-phenyl | |
| 102 | 2,3,4-(CH₃)₃-phenyl | |
| 103 | 2,3,5-(CH₃)₃-phenyl | |
| 104 | 2,3,6-(CH₃)₃-phenyl | |
| 105 | 2,4,5-(CH₃)₃-phenyl | |
| 106 | 2,4,6-(CH₃)₃-phenyl | |
| 107 | 3,4,5-(CH₃)₃-phenyl | |
| 108 | 2,3,4,6-(CH₃)₄-phenyl | |
| 109 | 2,3,5,6-(CH₃)₄-phenyl | |
| 110 | (CH₃)₅-phenyl | |
| 111 | 2,4-(C₂H₅)₂-phenyl | |
| 112 | 2,6-(C₂H₅)₂-phenyl | |
| 113 | 3,5-(C₂H₅)₂-phenyl | |
| 114 | 2,4,6-(C₂H₅)₃-phenyl | |
| 115 | 2,4-(i-C₃H₇)₂-phenyl | |
| 116 | 2,6-(i-C₃H₇)₂-phenyl | |
| 117 | 3,5-(i-C₃H₇)₂-phenyl | |
| 118 | 2,4,6-(i-C₃H₇)₃-phenyl | |
| 119 | 2,3-(t-C₄H₉)₂-phenyl | |
| 120 | 2,4-(t-C₄H₉)₂-phenyl | |
| 121 | 2,5-(t-C₄H₉)₂-phenyl | |
| 122 | 2,6-(t-C₄H₉)₂-phenyl | |
| 123 | 3,5-(t-C₄H₉)₂-phenyl | |
| 124 | 2,4,6-(t-C₄H₉)₃-phenyl | |
| 125 | 2-t-C₄H₉, 4-CH₃-phenyl | |
| 126 | 2-t-C₄H₉, 5-CH₃-phenyl | |
| 127 | 2,6-(t-C₄H₉)₂, 4-CH₃-phenyl | |
| 128 | 2-CH₃, 4-t-C₄H₉-phenyl | |
| 129 | 2-CH₃, 6-t-C₄H₉-phenyl | |
| 130 | 2-CH₃, 4-i-C₃H₇-phenyl | |
| 131 | 2-CH₃, 5-i-C₃H₇-phenyl | |
| 132 | 3-CH₃, 4-i-C₃H₇-phenyl | |
| 133 | 2-i-C₃H₇, 5-CH₃-phenyl | |
| 134 | 2,4-(t-C₄H₉)₂-6-i-C₃H₇-phenyl | |
| 135 | 2-cyclo-C₆H₁₁-phenyl | |
| 136 | 3-cyclo-C₆H₁₁-phenyl | |
| 137 | 4-cyclo-C₆H₁₁-phenyl | |
| 138 | 2,4-(cyclo-C₆H₁₁)₂-6-CH₃-phenyl | |
| 139 | 2-CH₃, 4-cyclo-C₆H₁₁-phenyl | |
| 140 | 2-CH₂C₆H₅-phenyl | |
| 141 | 3-CH₂C₆H₅-phenyl | |
| 142 | 4-CH₂C₆H₅-phenyl | |
| 143 | 2-CH₂C₆H₅, 4-CH₃-phenyl | |
| 144 | 2-CH₃, 4-CH₂C₆H₅-phenyl | |
| 145 | 2-C₆H₅-phenyl | |
| 146 | 3-C₆H₅-phenyl | |
| 147 | 4-C₆H₅-phenyl | |
| 148 | 4-(2-i-C₃H₇—C₆H₄)-phenyl | |
| 149 | 4-C₆H₅, 2,6-(CH₃)₂-phenyl | |
| 150 | 2-Cl, 4-C₆H₅-phenyl | |
| 151 | 2-Br, 4-C₆H₅-phenyl | |
| 152 | 2-C₆H₅, 4-Cl-phenyl | |
| 153 | 2-C₆H₅, 4-Br-phenyl | |
| 154 | 2-CH₂C₆H₅, 4-Cl-phenyl | |
| 155 | 2-CH₂C₆H₅, 4-Br-phenyl | |
| 156 | 2-Cl, 4-CH₂C₆H₅-phenyl | |
| 157 | 2-Br, 4-CH₂C₆H₅-phenyl | |
| 158 | 2-cyclo-C₆H₁₁, 4-Cl-phenyl | |
| 159 | 2-cyclo-C₆H₁₁, 4-Br-phenyl | |
| 160 | 2-Cl, 4-cyclo-C₆H₁₁-phenyl | |
| 161 | 2-Br, 4-cyclo-C₆H₁₁-phenyl | |
| 162 | 3-OCH₃-phenyl | |
| 163 | 2,4-(OCH₃)₂-phenyl | |
| 164 | 2-CF₃-phenyl | |
| 165 | 3-CF₃-phenyl | |
| 166 | 4-CF₃-phenyl | |
| 167 | 2-NO₂-phenyl | |
| 168 | 3-NO₂-phenyl | |
| 169 | 4-NO₂-phenyl | |
| 170 | 2-CN-phenyl | |
| 171 | 3-CN-phenyl | |
| 172 | 4-CN-phenyl | |
| 173 | 2-CH₃, 3-Cl-phenyl | |
| 174 | 2-CH₃, 4-Cl-phenyl | |
| 175 | 2-CH₃, 5-Cl-phenyl | |
| 176 | 2-CH₃, 6-Cl-phenyl | |
| 177 | 2-CH₃, 3-F-phenyl | |
| 178 | 2-CH₃, 4-F-phenyl | |
| 179 | 2-CH₃, 5-F-phenyl | |
| 180 | 2-CH₃, 6-F-phenyl | |
| 181 | 2-CH₃, 3-Br-phenyl | |
| 182 | 2-CH₃, 4-Br-phenyl | |
| 183 | 2-CH₃, 5-Br-phenyl | |
| 184 | 2-CH₃, 6-Br-phenyl | |
| 185 | 2-Cl, 3-CH₃-phenyl | |
| 186 | 2-Cl, 4-CH₃-phenyl | |
| 187 | 2-Cl, 5-CH₃-phenyl | |
| 188 | 2-Cl, 3-i-C₃H₇ | |
| 189 | 2-F, 3-CH₃-phenyl | |
| 190 | 2-F, 4-CH₃-phenyl | |
| 191 | 2-F, 5-CH₃-phenyl | |
| 192 | 2-Br, 3-CH₃-phenyl | |
| 193 | 2-Br, 4-CH₃-phenyl | |
| 194 | 3-CH₃, 4-Cl-phenyl | |
| 195 | 3-CH₃, 5-Cl-phenyl | |
| 196 | 2-Br, 5-CH₃-phenyl | |
| 197 | 3-CH₃, 4-F-phenyl | |
| 198 | 3-CH₃, 5-F-phenyl | |
| 199 | 3-CH₃, 4-Br-phenyl | |
| 200 | 3-CH₃, 5-Br-phenyl | |
| 201 | 3-F, 4-CH₃-phenyl | |
| 202 | 3-Cl, 4-CH₃-phenyl | |
| 203 | 3-Br, 4-CH₃-phenyl | |
| 204 | 2-Cl, 4,5-(CH₃)₂-phenyl | |
| 205 | 2-Br, 4,5-(CH₃)₂-phenyl | |
| 206 | 2-Cl, 3,5-(CH₃)₂-phenyl | |
| 207 | 2-Br, 3,5-(CH₃)₂-phenyl | |
| 208 | 2,6-Cl₂, 4-CH₃-phenyl | |
| 209 | 2,6-F₂, 4-CH₃-phenyl | |
| 210 | 2,6-Br₂, 4-CH₃-phenyl | |
| 211 | 2,4-Cl₂, 6-CH₃-phenyl | |
| 212 | 2,4-F₂, 6-CH₃-phenyl | |
| 213 | 2,4-Br₂, 6-CH₃-phenyl | |
| 214 | 2,6-(CH₃)₂, 4-F-phenyl | |
| 215 | 2,6-(CH₃)₂, 4-Cl-phenyl | |
| 216 | 2,6-(CH₃)₂, 4-Br-phenyl | |
| 217 | 3,5-(CH₃)₂, 4-F-phenyl | |
| 218 | 3,5-(CH₃)₂, 4-Cl-phenyl | |
| 219 | 3,5-(CH₃)₂, 4-Br-phenyl | |
| 220 | 2,3,6-(CH₃)₃, 4-F-phenyl | |
| 221 | 2,3,6-(CH₃)₃, 4-Cl-phenyl | |
| 222 | 2,3,6-(CH₃)₃, 4-Br-phenyl | |
| 223 | 2,4-(CH₃)₂, 6-F-phenyl | |
| 224 | 2,4-(CH₃)₂, 6-Cl-phenyl | |
| 225 | 2,4-(CH₃)₂, 6-Br-phenyl | |
| 226 | 2-i-C₃H₇, 4-Cl, 5-CH₃-phenyl | |
| 227 | 2-Cl, 4-NO₂-phenyl | |
| 228 | 2-NO₂, 4-Cl-phenyl | |
| 229 | 2-OCH₃, 5-NO₂-phenyl | |
| 230 | 2,4-Cl₂, 5-NO₂-phenyl | |
| 231 | 2,4-Cl₂, 6-NO₂-phenyl | |
| 232 | 2,6-Cl₂, 4-NO₂-phenyl | |
| 233 | 2,6-Br₂, 4-NO₂-phenyl | |
| 234 | 2,6-J₂, 4-NO₂-phenyl | |
| 235 | 2-C₆H₅O-phenyl | |
| 236 | 3-C₆H₅O-phenyl | |
| 237 | 4-C₆H₅O-phenyl | |
| 238 | 3-t-C₄H₉O-phenyl | |
| 239 | 4-t-C₄H₉O-phenyl | |
| 240 | 1-naphthyl | |

TABLE 4-continued

Structure: 2-position of benzene ring bears –CH$_2$–S–R; 1-position bears C(=O)–C(=N–OCH$_3$)–SCH$_3$

| No. | R | mp (°C.)/IR (cm$^{-1}$) |
|---|---|---|
| 241 | 2-naphthyl | |
| 242 | 2-pyridyl | |
| 243 | 6-methyl-2-pyridyl | 89–94° C. |
| 244 | 6-ethyl-2-pyridyl | |
| 245 | 6-n-propyl-2-pyridyl | |
| 246 | 6-iso-propyl-2-pyridyl | |
| 247 | 6-n-butyl-2-pyridyl | |
| 248 | 6-tert.-butyl-2-pyridyl | |
| 249 | 6-n-pentyl-2-pyridyl | |
| 250 | 6-n-hexyl-2-pyridyl | |
| 251 | 6-phenyl-2-pyridyl | |
| 252 | 6-benzyl-2-pyridyl | |
| 253 | 6-trifluoromethyl-2-pyridyl | |
| 254 | 6-methoxy-2-pyridyl | |
| 255 | 6-chloro-2-pyridyl | |
| 256 | 3,6-dimethyl-2-pyridyl | |
| 257 | 3,6-diethyl-2-pyridyl | |
| 258 | 4,6-dimethyl-2-pyridyl | |
| 259 | 5,6-dimethyl-2-pyridyl | |
| 260 | 4-phenyl-6-methyl-2-pyridyl | |
| 261 | 4,6-diphenyl-2-pyridyl | |
| 262 | 3,4-dichloro-6-methyl-2-pyridyl | |
| 263 | 3,4,5-trichloro-6-phenyl-2-pyridyl | |
| 264 | 4-trifluoromethyl-6-methyl-2-pyridyl | |
| 265 | 3-cyano-6-methyl-2-pyridyl | |
| 266 | 3-cyano-6-ethyl-2-pyridyl | |
| 267 | 3-cyano-6-n-propyl-2-pyridyl | |
| 268 | 3-cyano-6-iso-propyl-2-pyridyl | |
| 269 | 3-cyano-6-cyclo-propyl-2-pyridyl | |
| 270 | 3-cyano-6-n-butyl-2-pyridyl | |
| 271 | 3-cyano-6-tert.-butyl-2-pyridyl | |
| 272 | 3-cyano-6-cyclo-hexyl-2-pyridyl | |
| 273 | 3-cyano-6-phenyl-2-pyridyl | |
| 274 | 3-cyano-4,6-dimethyl-2-pyridyl | |
| 275 | 3,5,6-trichloro-2-pyridyl | |
| 276 | 5-trifluoromethyl-2-pyridyl | |
| 277 | 3-chloro-5-trifluoromethyl-2-pyridyl | |
| 278 | 2-quinolyl | |
| 279 | 3-methyl-2-quinolyl | |
| 280 | 4-methyl-2-quinolyl | |
| 281 | 4-ethyl-2-quinolyl | |
| 282 | 4-phenyl-2-quinolyl | |
| 283 | 6-methyl-2-quinolyl | |
| 284 | 6-chloro-2-quinolyl | |
| 285 | 8-methyl-2-quinolyl | |
| 286 | 8-chloro-2-quinolyl | |
| 287 | 3,4-dimethyl-2-quinolyl | |
| 288 | 4-methyl-8-methoxy-2-quinolyl | |
| 289 | 4-phenyl-8-ethoxy-2-quinolyl | |
| 290 | 4-methyl-8-chloro-2-quinolyl | |
| 291 | 4-methyl-8-fluoro-2-quinolyl | |
| 292 | 4-quinolyl | |
| 293 | 2-methyl-4-quinolyl | |
| 294 | 2-trifluoromethyl-4-quinolyl | |
| 295 | 2-iso-propyl-4-quinolyl | |
| 296 | 2-n-pentyl-4-quinolyl | |
| 297 | 2-phenyl-4-quinolyl | |
| 298 | 2,6-dimethyl-4-quinolyl | |
| 299 | 2-methyl-6-chloro-4-quinolyl | |
| 300 | 2-methyl-6-fluoro-4-quinolyl | |
| 301 | 8-quinolyl | |
| 302 | 2-methyl-8-quinolyl | |
| 303 | 5,7-dichloro-8-quinolyl | |
| 304 | 4,6-dimethyl-2-pyrimidinyl | |
| 305 | 4-trifluoromethyl-2-pyrimidinyl | |
| 306 | 4,5,6-trimethyl-2-pyrimidinyl | |
| 307 | 4-benzyl-6-methyl-2-pyrimidinyl | |
| 308 | 4-methyl-6-phenyl-2-pyrimidinyl | |
| 309 | 4,6-dimethyl-5-chloro-2-pyrimidinyl | |
| 310 | 2,6-dimethyl-4-pyrimidinyl | |
| 311 | 2,6-bis-(trifluoromethyl)-4-pyrimidinyl | |
| 312 | 2-iso-propyl-6-methyl-4-pyrimidinyl | |
| 313 | 2-cyclo-propyl-6-methyl-4-pyrimidinyl | |
| 314 | 2-methyl-6-methoxymethyl-4-pyrimidinyl | |
| 315 | 2-iso-propyl-6-methoxymethyl-4-pyrimidinyl | |
| 316 | 2-phenyl-4-pyrimidinyl | |
| 317 | 3,5-dimethyl-4-pyrimidinyl | |
| 318 | 2-methyl-6-trifluoromethyl-4-pyrimidinyl | |
| 319 | 2-n-propyl-6-trifluoromethyl-4-pyrimidinyl | |
| 320 | 2-iso-propyl-6-trifluoromethyl-4-pyrimidinyl | |
| 321 | 2-methyl-5-chloro-6-trifluoromethyl-4-pyrimidinyl | |
| 322 | 2-n-propyl-5-chloro-6-trifluoromethyl-4-pyrimidinyl | |
| 323 | 2-iso-propyl-5-chloro-6-trifluoromethyl-4-pyrimidinyl | |
| 324 | 2-tert.-butyl-5-chloro-6-trifluoromethyl-4-pyrimidinyl | |
| 325 | 6-EtO-benzothiazol-2-yl | |
| 326 | benzoxazol-2-yl | |
| 327 | 1-Me-imidazol-2-yl | |
| 328 | 4-but-1H-imidazol-2-yl | |
| 329 | 2-thiazolin-2-yl | |
| 330 | 5-CF$_3$-benzimidazol-2-yl | |
| 331 | 1-Ph-tetrazol-5-yl | |
| 332 | 5-CF$_3$-benzothiazol-2-yl | |
| 333 | 4,4-Me$_2$-5-methylene-2-thiazolin-2-yl | |
| 334 | 6-Cl-4-Me-benzothiazol-2-yl | |
| 335 | 5-Me-benzothiazol-2-yl | |
| 336 | 4-Cl-benzothiazol-2-yl | |
| 337 | 1-(3-NO$_2$—Ph)tetrazol-5-yl | |
| 338 | 2-thienyl | |
| 339 | 5-Me-benzoxazol-2-yl | |
| 340 | 7-Cl-benzothiazol-2-yl | |
| 341 | 5,6-Cl$_3$-1H-benzimidazol-2-yl | |
| 342 | 5-Cl-benzoxazol-2-yl | |
| 343 | 6-Cl-benzothiazol-2-yl | |
| 344 | 2-Ph-thiazol-2-yl | |
| 345 | 3-CN-4,6-Me$_2$-2-pyridyl | |
| 346 | 1-Ph-1,2,4-triazol-3-yl | |
| 347 | 1-Pri-benzimidazol-2-yl | |
| 348 | 5-Br-benzothiazol-2-yl | |
| 349' | 5-Br-1H-benzimidazol-2-yl | |
| 350 | 7-Cl-4-MeO-benzothiazol-2-yl | |
| 351 | 1H-benzimidazol-2-yl | |
| 352 | 5-Cl-benzothiazol-2-yl | |
| 353 | 5-NO$_2$-benzoxazol-2-yl | |
| 354 | 5-t-Bu-benzoxazol-2-yl | |
| 355 | 4,6,7-Cl$_3$-benzothiozol-2-yl | |
| 356 | 5-Ph-thiazol-2-yl | |
| 357 | 5,7-Me$_2$-benzoxazol-2-yl | |
| 358 | 6-Me-benzoxazol-2-yl | |
| 359 | 1,2,4-triazin-3-yl | |
| 360 | 6-Pr-benzothiazol-2-yl | |
| 361 | 6-PhO-benzothiazol-2-yl | |
| 362 | 4-(4-Cl—Ph)-thiazol-2-yl | |
| 363 | 4-(4-Me—Ph)-thiazol-2-yl | |
| 364 | 5-Me-4-Ph-thiazol-2-yl | |

TABLE 4-continued

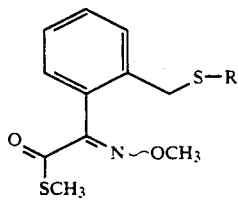

| No. | R | mp (°C.)/IR (cm$^{-1}$) |
|---|---|---|
| 365 | 5-Cl-1-H-benzimidazol-2-yl | |
| 366 | 5-Ph-1,2,4-triazol-3-yl | |
| 367 | 3-Ph-1,2,4-thiadiazol-5-yl | |

TABLE 5

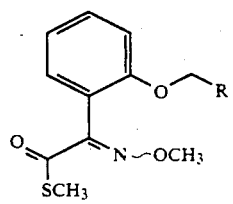

| No. | R | mp(°C.)/IR(cm$^{-1}$) |
|---|---|---|
| 1 | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-NO$_2$-phenyl | |
| 29 | 3-NO$_3$-phenyl | |
| 30 | 4-NO$_2$-phenyl | |
| 31 | 2-CH$_3$-phenyl | |
| 32 | 3-CH$_3$-phenyl | |
| 33 | 4-CH$_3$-phenyl | |
| 34 | 2-OMe-phenyl | |
| 35 | 3-OMe-phenyl | |
| 36 | 4-OMe-phenyl | |
| 37 | 2-CF$_3$-phenyl | |
| 38 | 3-CF$_3$-phenyl | |
| 39 | 4-CF$_3$-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |
| 50 | 2-thienyl | |

TABLE 5-continued

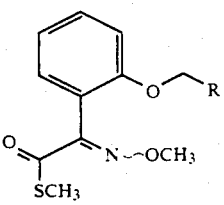

| No. | R | mp(°C.)/IR(cm$^{-1}$) |
|---|---|---|
| 51 | 2-furyl | |
| 52 | 2-imidazolyl | |

TABLE 6

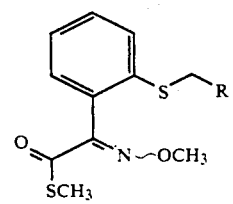

| No. | R | mp(°C.)/IR(cm$^{-1}$) |
|---|---|---|
| 1 | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-NO$_2$-phenyl | |
| 29 | 3-NO$_3$-phenyl | |
| 30 | 4-NO$_2$-phenyl | |
| 31 | 2-CH$_3$-phenyl | |
| 32 | 3-CH$_3$-phenyl | |
| 33 | 4-CH$_3$-phenyl | |
| 34 | 2-OMe-phenyl | |
| 35 | 3-OMe-phenyl | |
| 36 | 4-OMe-phenyl | |
| 37 | 2-CF$_3$-phenyl | |
| 38 | 3-CF$_3$-phenyl | |
| 39 | 4-CF$_3$-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |
| 50 | 2-thienyl | |
| 51 | 2-furyl | |

TABLE 6-continued

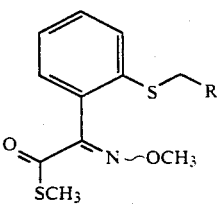

| No. | R | mp(°C.)/IR(cm⁻¹) |
|---|---|---|
| 52 | 2-imidazolyl | |

TABLE 7

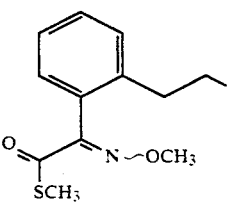

| No. | R | mp(°C.)/IR(cm⁻¹) |
|---|---|---|
| 1 | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-NO₂-phenyl | |
| 29 | 3-NO₃-phenyl | |
| 30 | 4-NO₂-phenyl | |
| 31 | 2-CH₃-phenyl | |
| 32 | 3-CH₃-phenyl | |
| 33 | 4-CH₃-phenyl | |
| 34 | 2-OMe-phenyl | |
| 35 | 3-OMe-phenyl | |
| 36 | 4-OMe-phenyl | |
| 37 | 2-CF₃-phenyl | |
| 38 | 3-CF₃-phenyl | |
| 39 | 4-CF₃-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |
| 50 | 2-thienyl | |
| 51 | 2-furyl | |

TABLE 7-continued

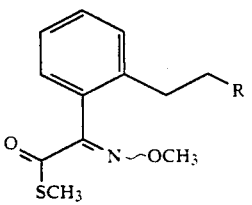

| No. | R | mp(°C.)/IR(cm⁻¹) |
|---|---|---|
| 52 | 2-imidazolyl | |

TABLE 8

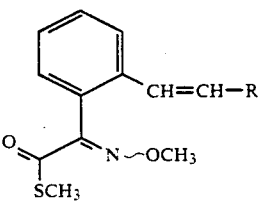

| No. | R | mp(°C.)/IR(cm⁻¹) |
|---|---|---|
| 1 | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-NO₂-phenyl | |
| 29 | 3-NO₃-phenyl | |
| 30 | 4-NO₂-phenyl | |
| 31 | 2-CH₃-phenyl | |
| 32 | 3-CH₃-phenyl | |
| 33 | 4-CH₃-phenyl | |
| 34 | 2-OMe-phenyl | |
| 35 | 3-OMe-phenyl | |
| 36 | 4-OMe-phenyl | |
| 37 | 2-CF₃-phenyl | |
| 38 | 3-CF₃-phenyl | |
| 39 | 4-CF₃-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |
| 50 | 2-thienyl | |
| 51 | 2-furyl | |

TABLE 8-continued

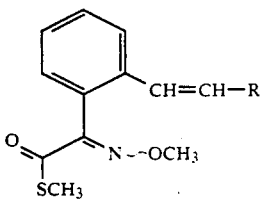

| No. | R | mp(°C.)/IR(cm⁻¹) |
|---|---|---|
| 52 | 2-imidazolyl | |

TABLE 9

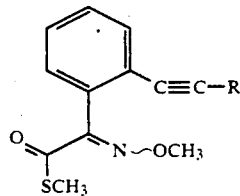

| No. | R | mp(°C.)/IR(cm⁻¹) |
|---|---|---|
| 1 | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-NO₂-phenyl | |
| 29 | 3-NO₂-phenyl | |
| 30 | 4-NO₂-phenyl | |
| 31 | 2-CH₃-phenyl | |
| 32 | 3-CH₃-phenyl | |
| 33 | 4-CH₃-phenyl | |
| 34 | 2-OMe-phenyl | |
| 35 | 3-OMe-phenyl | |
| 36 | 4-OMe-phenyl | |
| 37 | 2-CF₃-phenyl | |
| 38 | 3-CF₃-phenyl | |
| 39 | 4-CF₃-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |
| 50 | 2-thienyl | |
| 51 | 2-furyl | |

TABLE 9-continued

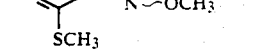

| No. | R | mp(°C.)/IR(cm⁻¹) |
|---|---|---|
| 52 | 2-imidazolyl | |

TABLE 10

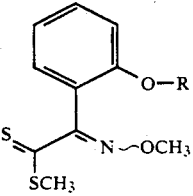

| No. | R | mp(°C.)/IR(cm⁻¹) |
|---|---|---|
| 1 | methyl | |
| 2 | ethyl | |
| 3 | n-propyl | |
| 4 | iso-propyl | |
| 5 | n-butyl | |
| 6 | s-butyl | |
| 7 | iso-butyl | |
| 8 | tert.-butyl | |
| 9 | pentyl | |
| 10 | hexyl | |
| 11 | phenyl | |
| 12 | 2-F-phenyl | |
| 13 | 3-F-phenyl | |
| 14 | 4-F-phenyl | |
| 15 | 2-Cl-phenyl | |
| 16 | 3-Cl-phenyl | |
| 17 | 4-Cl-phenyl | |
| 18 | 2-Br-phenyl | |
| 19 | 3-Br-phenyl | |
| 20 | 4-Br-phenyl | |
| 21 | 2-I-phenyl | |
| 22 | 3-I-phenyl | |
| 23 | 4-I-phenyl | |
| 24 | 2-CN-phenyl | |
| 25 | 3-CN-phenyl | |
| 26 | 4-CN-phenyl | |
| 27 | 2,3-F₂-phenyl | |
| 28 | 2,4-F₂-phenyl | |
| 29 | 2,3-Cl₂-phenyl | |
| 30 | 2,4-Cl₂-phenyl | |
| 31 | 2,5-Cl₂-phenyl | |
| 32 | 2,6-Cl₂-phenyl | |
| 33 | 3,4-Cl₂-phenyl | |
| 34 | 3,5-Cl₂-phenyl | |
| 35 | 2,4-Br₂-phenyl | |
| 36 | 2,5-Br₂-phenyl | |
| 37 | 2,6-Br₂-phenyl | |
| 38 | 2,4-I₂-phenyl | |
| 39 | 2-Cl, 3-F-phenyl | |
| 40 | 2-Cl, 4-F-phenyl | |
| 41 | 2-Cl, 5-F-phenyl | |
| 42 | 2-Cl, 6-F-phenyl | |
| 43 | 2-Cl, 3-Br-phenyl | |
| 44 | 2-Cl, 4-Br-phenyl | |
| 45 | 2-Cl, 5-Br-phenyl | |
| 46 | 2-Cl, 6-Br-phenyl | |
| 47 | 2-Br, 3-Cl-phenyl | |
| 48 | 2-Br, 4-Cl-phenyl | |
| 49 | 2-Br, 3-F-phenyl | |
| 50 | 2-Br, 4-F-phenyl | |
| 51 | 2-Br, 5-F-phenyl | |

TABLE 10-continued

[Structure: 2-(O-R)-phenyl group attached to C(=S-SCH₃)(=N-OCH₃)]

| No. | R | mp(°C.)/IR(cm⁻¹) |
|---|---|---|
| 52 | 2-Br, 6-F-phenyl | |
| 53 | 2-F, 3-Cl-phenyl | |
| 54 | 2-F, 4-Cl-phenyl | |
| 55 | 2-F, 5-Cl-phenyl | |
| 56 | 3-Cl, 4-F-phenyl | |
| 57 | 3-Cl, 5-F-phenyl | |
| 58 | 3-Cl, 4-Br-phenyl | |
| 59 | 3-Cl, 5-Br-phenyl | |
| 60 | 3-F, 4-Cl-phenyl | |
| 61 | 3-F, 4-Br-phenyl | |
| 62 | 3-Br, 4-Cl-phenyl | |
| 63 | 3-Br, 4-F-phenyl | |
| 64 | 2,4,6-F₃-phenyl | |
| 65 | 2,3,4,-Cl₃-phenyl | |
| 66 | 2,3,5-Cl₃-phenyl | |
| 67 | 2,3,6-Cl₃-phenyl | |
| 68 | 2,4,5-Cl₃-phenyl | |
| 69 | 2,4,6-Cl₃-phenyl | |
| 70 | 3,4,5-Cl₃-phenyl | |
| 71 | 2,4,6-Br₃-phenyl | |
| 72 | 2,6-Cl₂-4-Br-phenyl | |
| 73 | 2,3,4,6-Cl₄-phenyl | |
| 74 | 2,3,5,6-Cl₄-phenyl | |
| 75 | F₅-phenyl | |
| 76 | Cl₅-phenyl | |
| 77 | Br₅-phenyl | |
| 78 | 2-CH₃-phenyl | |
| 79 | 3-CH₃-phenyl | |
| 80 | 4-CH₃-phenyl | |
| 81 | 2-C₂H₅-phenyl | |
| 82 | 3-C₂H₅-phenyl | |
| 83 | 4-C₂H₅-phenyl | |
| 84 | 2-n-C₃H₇-phenyl | |
| 85 | 3-n-C₃H₇-phenyl | |
| 86 | 4-n-C₃H₇-phenyl | |
| 87 | 2-i-C₃H₇-phenyl | |
| 88 | 3-i-C₃H₇-phenyl | |
| 89 | 4-i-C₃H₇-phenyl | |
| 90 | 2-s-C₄H₉-phenyl | |
| 91 | 3-s-C₄H₉-phenyl | |
| 92 | 4-s-C₄H₉-phenyl | |
| 93 | 2-t-C₄H₉-phenyl | |
| 94 | 3-t-C₄H₉-phenyl | |
| 95 | 4-t-C₄H₉-phenyl | |
| 96 | 2,3-(CH₃)₂-phenyl | |
| 97 | 2,4-(CH₃)₂-phenyl | |
| 98 | 2,5-(CH₃)₂-phenyl | |
| 99 | 2,6-(CH₃)₂-phenyl | |
| 100 | 3,4-(CH₃)₂-phenyl | |
| 101 | 3,5-(CH₃)₂-phenyl | |
| 102 | 2,3,4-(CH₃)₃-phenyl | |
| 103 | 2,3,5-(CH₃)₃-phenyl | |
| 104 | 2,3,6-(CH₃)₃-phenyl | |
| 105 | 2,4,5-(CH₃)₃-phenyl | |
| 106 | 2,4,6-(CH₃)₃-phenyl | |
| 107 | 3,4,5-(CH₃)₃-phenyl | |
| 108 | 2,3,4,6-(CH₃)₄-phenyl | |
| 109 | 2,3,5,6-(CH₃)₄-phenyl | |
| 110 | (CH₃)₅-phenyl | |
| 111 | 2,4-(C₂H₅)₂-phenyl | |
| 112 | 2,6-(C₂H₅)₂-phenyl | |
| 113 | 3,5-(C₂H₅)₂-phenyl | |
| 114 | 2,4,6-(C₂H₅)₃-phenyl | |
| 115 | 2,4-(i-C₃H₇)₂-phenyl | |
| 116 | 2,6-(i-C₃H₇)₂-phenyl | |
| 117 | 3,5-(i-C₃H₇)₂-phenyl | |
| 118 | 2,4,6-(i-C₃H₇)₃-phenyl | |
| 119 | 2,3-(t-C₄H₉)₂-phenyl | |
| 120 | 2,4-(t-C₄H₉)₂-phenyl | |
| 121 | 2,5-(t-C₄H₉)₂-phenyl | |
| 122 | 2,6-(t-C₄H₉)₂-phenyl | |
| 123 | 3,5-(t-C₄H₉)₂-phenyl | |
| 124 | 2,4,6-(t-C₄H₉)₃-phenyl | |
| 125 | 2-t-C₄H₉, 4-CH₃-phenyl | |
| 126 | 2-t-C₄H₉, 5-CH₃-phenyl | |
| 127 | 2,6-(t-C₄H₉)₂, 4-CH₃-phenyl | |
| 128 | 2-CH₃, 4-t-C₄H₉-phenyl | |
| 129 | 2-CH₃, 6-t-C₄H₉-phenyl | |
| 130 | 2-CH₃, 4-i-C₃H₇-phenyl | |
| 131 | 2-CH₃, 5-i-C₃H₇-phenyl | |
| 132 | 3-CH₃, 4-i-C₃H₇-phenyl | |
| 133 | 2-i-C₃H₇, 5-CH₃-phenyl | |
| 134 | 2,4-(t-C₄H₉)₂-6-i-C₃H₇-phenyl | |
| 135 | 2-cyclo-C₆H₁₁-phenyl | |
| 136 | 3-cyclo-C₆H₁₁-phenyl | |
| 137 | 4-cyclo-C₆H₁₁-phenyl | |
| 138 | 2,4-(cyclo-C₆H₁₁)₂-6-CH₃-phenyl | |
| 139 | 2-CH₃, 4-cyclo-C₆H₁₁-phenyl | |
| 140 | 2-CH₂C₆H₅-phenyl | |
| 141 | 3-CH₂C₆H₅-phenyl | |
| 142 | 4-CH₂C₆H₅-phenyl | |
| 143 | 2-CH₂C₆H₅, 4-CH₃-phenyl | |
| 144 | 2-CH₃, 4-CH₂C₆H₅-phenyl | |
| 145 | 2-C₆H₅-phenyl | |
| 146 | 3-C₆H₅-phenyl | |
| 147 | 4-C₆H₅-phenyl | |
| 148 | 4-(2-i-C₃H₇—C₆H₄)-phenyl | |
| 149 | 4-C₆H₅, 2,6-(CH₃)₂-phenyl | |
| 150 | 2-Cl, 4-C₆H₅-phenyl | |
| 151 | 2-Br, 4-C₆H₅-phenyl | |
| 152 | 2-C₆H₅, 4-Cl-phenyl | |
| 153 | 2-C₆H₅, 4-Br-phenyl | |
| 154 | 2-CH₂C₆H₅, 4-Cl-phenyl | |
| 155 | 2-CH₂C₆H₅, 4-Br-phenyl | |
| 156 | 2-Cl, 4-CH₂C₆H₅-phenyl | |
| 157 | 2-Br, 4-CH₂C₆H₅-phenyl | |
| 158 | 2-cyclo-C₆H₁₁, 4-Cl-phenyl | |
| 159 | 2-cyclo-C₆H₁₁, 4-Br-phenyl | |
| 160 | 2-Cl, 4-cyclo-C₆H₁₁-phenyl | |
| 161 | 2-Br, 4-cyclo-C₆H₁₁-phenyl | |
| 162 | 2-OCH₃-phenyl | |
| 163 | 3-OCH₃-phenyl | |
| 164 | 4-OCH₃-phenyl | |
| 165 | 2,4-(OCH₃)₂-phenyl | |
| 166 | 2-CF₃-phenyl | |
| 167 | 3-CF₃-phenyl | |
| 168 | 4-CF₃-phenyl | |
| 169 | 2-NO₂-phenyl | |
| 170 | 3-NO₂-phenyl | |
| 171 | 4-NO₂-phenyl | |
| 172 | 2-CN-phenyl | |
| 173 | 3-CN-phenyl | |
| 174 | 4-CN-phenyl | |
| 175 | 2-CH₃, 3-Cl-phenyl | |
| 176 | 2-CH₃, 4-Cl-phenyl | |
| 177 | 2-CH₃, 5-Cl-phenyl | |
| 178 | 2-CH₃, 6-Cl-phenyl | |
| 179 | 2-CH₃, 3-F-phenyl | |
| 180 | 2-CH₃, 4-F-phenyl | |
| 181 | 2-CH₃, 5-F-phenyl | |
| 182 | 2-CH₃, 6-F-phenyl | |
| 183 | 2-CH₃, 3-Br-phenyl | |
| 184 | 2-CH₃, 4-Br-phenyl | |
| 185 | 2-CH₃, 5-Br-phenyl | |
| 186 | 2-CH₃, 6-Br-phenyl | |
| 187 | 2-Cl, 3-CH₃-phenyl | |
| 188 | 2-Cl, 4-CH₃-phenyl | |
| 189 | 2-Cl, 5-CH₃-phenyl | |

TABLE 10-continued

[Structure: phenyl ring with O-R at ortho position, C(=S)(SCH3)-C(=N-OCH3) substituent]

| No. | R | mp(°C.)/IR(cm⁻¹) |
|---|---|---|
| 190 | 2-Cl, 3-i-C₃H₇ | |
| 191 | 2-F, 3-CH₃-phenyl | |
| 192 | 2-F, 4-CH₃-phenyl | |
| 193 | 2-F, 5-CH₃-phenyl | |
| 194 | 2-Br, 3-CH₃-phenyl | |
| 195 | 2-Br, 4-CH₃-phenyl | |
| 196 | 3-CH₃, 4-Cl-phenyl | |
| 197 | 3-CH₃, 5-Cl-phenyl | |
| 198 | 2-Br, 5-CH₃-phenyl | |
| 199 | 3-CH₃, 4-F-phenyl | |
| 200 | 3-CH₃, 5-F-phenyl | |
| 201 | 3-CH₃, 4-Br-phenyl | |
| 202 | 3-CH₃, 5-Br-phenyl | |
| 203 | 3-F, 4-CH₃-phenyl | |
| 204 | 3-Cl, 4-CH₃-phenyl | |
| 205 | 3-Br, 4-CH₃-phenyl | |
| 206 | 2-Cl, 4,5-(CH₃)₂-phenyl | |
| 207 | 2-Br, 4,5-(CH₃)₂-phenyl | |
| 208 | 2-Cl, 3,5-(CH₃)₂-phenyl | |
| 209 | 2-Br, 3,5-(CH₃)₂-phenyl | |
| 210 | 2,6-Cl₂, 4-CH₃-phenyl | |
| 211 | 2,6-F₂, 4-CH₃-phenyl | |
| 212 | 2,6-Br₂, 4-CH₃-phenyl | |
| 213 | 2,4-Cl₂, 6-CH₃-phenyl | |
| 214 | 2,4-F₂, 6-CH₃-phenyl | |
| 215 | 2,4-Br₂, 6-CH₃-phenyl | |
| 216 | 2,6-(CH₃)₂, 4-F-phenyl | |
| 217 | 2,6-(CH₃)₂, 4-Cl-phenyl | |
| 218 | 2,6-(CH₃)₂, 4-Br-phenyl | |
| 219 | 3,5-(CH₃)₂, 4-F-phenyl | |
| 220 | 3,5-(CH₃)₂, 4-Cl-phenyl | |
| 221 | 3,5-(CH₃)₂, 4-Br-phenyl | |
| 222 | 2,3,6-(CH₃)₃, 4-F-phenyl | |
| 223 | 2,3,6-(CH₃)₃, 4-Cl-phenyl | |
| 224 | 2,3,6-(CH₃)₃, 4-Br-phenyl | |
| 225 | 2,4-(CH₃)₂, 6-F-phenyl | |
| 226 | 2,4-(CH₃)₂, 6-Cl-phenyl | |
| 227 | 2,4-(CH₃)₂, 6-Br-phenyl | |
| 228 | 2-i-C₃H₇, 4-Cl, 5-CH₃-phenyl | |
| 229 | 2-Cl, 4-NO₂-phenyl | |
| 230 | 2-NO₂, 4-Cl-phenyl | |
| 231 | 2-OCH₃, 5-NO₂-phenyl | |
| 232 | 2,4-Cl₂, 5-NO₂-phenyl | |
| 233 | 2,4-Cl₂, 6-NO₂-phenyl | |
| 234 | 2,6-Cl₂, 4-NO₂-phenyl | |
| 235 | 2,6-Br₂, 4-NO₂-phenyl | |
| 236 | 2,6-I₂, 4-NO₂-phenyl | |
| 237 | 2-C₆H₅O-phenyl | |
| 238 | 3-C₆H₅O-phenyl | |
| 239 | 4-C₆H₅O-phenyl | |
| 240 | 3-t-C₄H₉O-phenyl | |
| 241 | 4-t-C₄H₉O-phenyl | |
| 242 | 1-naphthyl | |
| 243 | 2-naphthyl | |
| 244 | 2-pyridyl | |
| 245 | 6-methyl-2-pyridyl | |
| 246 | 6-ethyl-2-pyridyl | |
| 247 | 6-n-propyl-2-pyridyl | |
| 248 | 6-iso-propyl-2-pyridyl | |
| 249 | 6-n-butyl-2-pyridyl | |
| 250 | 6-tert.-butyl-2-pyridyl | |
| 251 | 6-n-pentyl-2-pyridyl | |
| 252 | 6-n-hexyl-2-pyridyl | |
| 253 | 6-phenyl-2-pyridyl | |
| 254 | 6-benzyl-2-pyridyl | |
| 255 | 6-trifluoromethyl-2-pyridyl | |
| 256 | 6-methoxy-2-pyridyl | |
| 257 | 6-chloro-2-pyridyl | |
| 258 | 3,6-dimethyl-2-pyridyl | |
| 259 | 3,6-diethyl-2-pyridyl | |
| 260 | 4,6-dimethyl-2-pyridyl | |
| 261 | 5,6-dimethyl-2-pyridyl | |
| 262 | 4-phenyl-6-methyl-2-pyridyl | |
| 263 | 4,6-diphenyl-2-pyridyl | |
| 264 | 3,4-dichloro-6-methyl-2-pyridyl | |
| 265 | 3,4,5-trichloro-6-phenyl-2-pyridyl | |
| 266 | 4-trifluoromethyl-6-methyl-2-pyridyl | |
| 267 | 3-cyano-6-methyl-2-pyridyl | |
| 268 | 3-cyano-6-ethyl-2-pyridyl | |
| 269 | 3-cyano-6-n-propyl-2-pyridyl | |
| 270 | 3-cyano-6-iso-propyl-2-pyridyl | |
| 271 | 3-cyano-6-cyclo-propyl-2-pyridyl | |
| 272 | 3-cyano-6-n-butyl-2-pyridyl | |
| 273 | 3-cyano-6-tert.-butyl-2-pyridyl | |
| 274 | 3-cyano-6-cyclo-hexyl-2-pyridyl | |
| 275 | 3-cyano-6-phenyl-2-pyridyl | |
| 276 | 3-cyano-4,6-dimethyl-2-pyridyl | |
| 277 | 3,5,6-trichloro-2-pyridyl | |
| 278 | 5-trifluoromethyl-2-pyridyl | |
| 279 | 3-chloro-5-trifluoromethyl-2-pyridyl | |
| 280 | 2-quinolyl | |
| 281 | 3-methyl-2-quinolyl | |
| 282 | 4-methyl-2-quinolyl | |
| 283 | 4-ethyl-2-quinolyl | |
| 284 | 4-phenyl-2-quinolyl | |
| 285 | 6-methyl-2-quinolyl | |
| 286 | 6-chloro-2-quinolyl | |
| 287 | 8-methyl-2-quinolyl | |
| 288 | 8-chloro-2-quinolyl | |
| 289 | 3,4-dimethyl-2-quinolyl | |
| 290 | 4-methyl-8-methoxy-2-quinolyl | |
| 291 | 4-phenyl-8-ethoxy-2-quinolyl | |
| 292 | 4-methyl-8-chloro-2-quinolyl | |
| 293 | 4-methyl-8-fluoro-2-quinolyl | |
| 294 | 4-quinolyl | |
| 295 | 2-methyl-4-quinolyl | |
| 296 | 2-trifluoromethyl-4-quinolyl | |
| 297 | 2-iso-propyl-4-quinolyl | |
| 298 | 2-n-pentyl-4-quinolyl | |
| 299 | 2-phenyl-4-quinolyl | |
| 300 | 2,6-dimethyl-4-quinolyl | |
| 301 | 2-methyl-6-chloro-4-quinolyl | |
| 302 | 2-methyl-6-fluoro-4-quinolyl | |
| 303 | 8-quinolyl | |
| 304 | 2-methyl-8-quinolyl | |
| 305 | 5,7-dichloro-8-quinolyl | |
| 306 | 4,6-dimethyl-2-pyrimidinyl | |
| 307 | 4-trifluoromethyl-2-pyrimidinyl | |
| 308 | 4,5,6-trimethyl-2-pyrimidinyl | |
| 309 | 4-benzyl-6-methyl-2-pyrimidinyl | |
| 310 | 4-methyl-6-phenyl-2-pyrimidinyl | |
| 311 | 4,6-dimethyl-5-chloro-2-pyrimidinyl | |
| 312 | 2,6-dimethyl-4-pyrimidinyl | |
| 313 | 2,6-bis-(trifluoromethyl)-4-pyrimidinyl | |
| 314 | 2-iso-propyl-6-methyl-4-pyrimidinyl | |
| 315 | 2-cyclo-propyl-6-methyl-4-pyrimidinyl | |
| 316 | 2-methyl-6-methoxymethyl-4-pyrimidinyl | |
| 317 | 2-iso-propyl-6-methoxymethyl-4-pyrimidinyl | |
| 318 | 2-phenyl-4-pyrimidinyl | |
| 319 | 3,5-dimethyl-4-pyrimidinyl | |
| 320 | 2-methyl-6-trifluoromethyl-4-pyrimidinyl | |
| 321 | 2-n-propyl-6-trifluoromethyl-4-pyrimidinyl | |
| 322 | 2-iso-propyl-6-trifluoromethyl-4-pyrimidinyl | |
| 323 | 2-methyl-5-chloro-6-trifluoromethyl-4-pyrimidinyl | |
| 324 | 2-n-propyl-5-chloro-6-trifluoromethyl-4-pyrimidinyl | |
| 325 | 2-iso-propyl-5-chloro-6-trifluoromethyl- | |

TABLE 10-continued

Structure: 2-(OR)-phenyl group attached to C(=S)(SCH₃) and C(=NOCH₃)

| No. | R | mp(°C.)/IR(cm⁻¹) |
|---|---|---|
| | 4-pyrimidinyl | |
| 326 | 2-tert.-butyl-5-chloro-6-trifluoromethyl-4-pyrimidinyl | |

TABLE 11

Structure: 2-(SR)-phenyl group attached to C(=S)(SMe) and C(=NOCH₃)

| No. | R | mp(°C.)/IR(cm⁻¹) |
|---|---|---|
| 1 | methyl | |
| 2 | ethyl | |
| 3 | n-propyl | |
| 4 | iso-propyl | |
| 5 | n-butyl | |
| 6 | s-butyl | |
| 7 | iso-butyl | |
| 8 | tert.-butyl | |
| 9 | pentyl | |
| 10 | hexyl | |
| 11 | phenyl | |
| 12 | 2-F-phenyl | |
| 13 | 3-F-phenyl | |
| 14 | 4-F-phenyl | |
| 15 | 2-Cl-phenyl | |
| 16 | 3-Cl-phenyl | |
| 17 | 4-Cl-phenyl | |
| 18 | 2-Br-phenyl | |
| 19 | 3-Br-phenyl | |
| 20 | 4-Br-phenyl | |
| 21 | 2-I-phenyl | |
| 22 | 3-I-phenyl | |
| 23 | 4-I-phenyl | |
| 24 | 2-CN-phenyl | |
| 25 | 3-CN-phenyl | |
| 26 | 4-CN-phenyl | |
| 27 | 2,3-F₂-phenyl | |
| 28 | 2,4-F₂-phenyl | |
| 29 | 2,3-Cl₂-phenyl | |
| 30 | 2,4-Cl₂-phenyl | |
| 31 | 2,5-Cl₂-phenyl | |
| 32 | 2,6-Cl₂-phenyl | |
| 33 | 3,4-Cl₂-phenyl | |
| 34 | 3,5-Cl₂-phenyl | |
| 35 | 2,4-Br₂-phenyl | |
| 36 | 2,5-Br₂-phenyl | |
| 37 | 2,6-Br₂-phenyl | |
| 38 | 2,4-I₂-phenyl | |
| 39 | 2-Cl, 3-F-phenyl | |
| 40 | 2-Cl, 4-F-phenyl | |
| 41 | 2-Cl, 5-F-phenyl | |
| 42 | 2-Cl, 6-F-phenyl | |
| 43 | 2-Cl, 3-Br-phenyl | |
| 44 | 2-Cl, 4-Br-phenyl | |
| 45 | 2-Cl, 5-Br-phenyl | |
| 46 | 2-Cl, 6-Br-phenyl | |
| 47 | 2-Br, 3-Cl-phenyl | |
| 48 | 2-Br, 4-Cl-phenyl | |
| 49 | 2-Br, 3-F-phenyl | |
| 50 | 2-Br, 4-F-phenyl | |
| 51 | 2-Br, 5-F-phenyl | |
| 52 | 2-Br, 6-F-phenyl | |
| 53 | 2-F, 3-Cl-phenyl | |
| 54 | 2-F, 4-Cl-phenyl | |
| 55 | 2-F, 5-Cl-phenyl | |
| 56 | 3-Cl, 4-F-phenyl | |
| 57 | 3-Cl, 5-F-phenyl | |
| 58 | 3-Cl, 4-Br-phenyl | |
| 59 | 3-Cl, 5-Br-phenyl | |
| 60 | 3-F, 4-Cl-phenyl | |
| 61 | 3-F, 4-Br-phenyl | |
| 62 | 3-Br, 4-Cl-phenyl | |
| 63 | 3-Br, 4-F-phenyl | |
| 64 | 2,4,6-F₃-phenyl | |
| 65 | 2,3,4,-Cl₃-phenyl | |
| 66 | 2,3,5-Cl₃-phenyl | |
| 67 | 2,3,6-Cl₃-phenyl | |
| 68 | 2,4,5-Cl₃-phenyl | |
| 69 | 2,4,6-Cl₃-phenyl | |
| 70 | 3,4,5-Cl₃-phenyl | |
| 71 | 2,4,6-Br₃-phenyl | |
| 72 | 2,6-Cl₂-4-Br-phenyl | |
| 73 | 2,3,4,6-Cl₄-phenyl | |
| 74 | 2,3,5,6-Cl₄-phenyl | |
| 75 | F₅-phenyl | |
| 76 | Cl₅-phenyl | |
| 77 | Br₅-phenyl | |
| 78 | 2-CH₃-phenyl | |
| 79 | 3-CH₃-phenyl | |
| 80 | 4-CH₃-phenyl | |
| 81 | 2-C₂H₅-phenyl | |
| 82 | 3-C₂H₅-phenyl | |
| 83 | 4-C₂H₅-phenyl | |
| 84 | 2-n-C₃H₇-phenyl | |
| 85 | 3-n-C₃H₇-phenyl | |
| 86 | 4-n-C₃H₇-phenyl | |
| 87 | 2-i-C₃H₇-phenyl | |
| 88 | 3-i-C₃H₇-phenyl | |
| 89 | 4-i-C₃H₇-phenyl | |
| 90 | 2-s-C₄H₉-phenyl | |
| 91 | 3-s-C₄H₉-phenyl | |
| 92 | 4-s-C₄H₉-phenyl | |
| 93 | 2-t-C₄H₉-phenyl | |
| 94 | 3-t-C₄H₉-phenyl | |
| 95 | 4-t-C₄H₉-phenyl | |
| 96 | 2,3-(CH₃)₂-phenyl | |
| 97 | 2,4-(CH₃)₂-phenyl | |
| 98 | 2,5-(CH₃)₂-phenyl | |
| 99 | 2,6-(CH₃)₂-phenyl | |
| 100 | 3,4-(CH₃)₂-phenyl | |
| 101 | 3,5-(CH₃)₂-phenyl | |
| 102 | 2,3,4-(CH₃)₃-phenyl | |
| 103 | 2,3,5-(CH₃)₃-phenyl | |
| 104 | 2,3,6-(CH₃)₃-phenyl | |
| 105 | 2,4,5-(CH₃)₃-phenyl | |
| 106 | 2,4,6-(CH₃)₃-phenyl | |
| 107 | 3,4,5-(CH₃)₃-phenyl | |
| 108 | 2,3,4,6-(CH₃)₄-phenyl | |
| 109 | 2,3,5,6-(CH₃)₄-phenyl | |
| 110 | (CH₃)₅-phenyl | |
| 111 | 2,4-(C₂H₅)₂-phenyl | |
| 112 | 2,6-(C₂H₅)₂-phenyl | |
| 113 | 3,5-(C₂H₅)₂-phenyl | |
| 114 | 2,4,6-(C₂H₅)₃-phenyl | |
| 115 | 2,4-(i-C₃H₇)₂-phenyl | |
| 116 | 2,6-(i-C₃H₇)₂-phenyl | |
| 117 | 3,5-(i-C₃H₇)₂-phenyl | |
| 118 | 2,4,6-(i-C₃H₇)₃-phenyl | |
| 119 | 2,3-(t-C₄H₉)₂-phenyl | |
| 120 | 2,4-(t-C₄H₉)₂-phenyl | |

TABLE 11-continued

| No. | R | mp(°C.)/IR(cm$^{-1}$) |
|---|---|---|
| 121 | 2,5-(t-C$_4$H$_9$)$_2$-phenyl | |
| 122 | 2,6-(t-C$_4$H$_9$)$_2$-phenyl | |
| 123 | 3,5-(t-C$_4$H$_9$)$_2$-phenyl | |
| 124 | 2,4,6-(t-C$_4$H$_9$)$_3$-phenyl | |
| 125 | 2-t-C$_4$H$_9$, 4-CH$_3$-phenyl | |
| 126 | 2-t-C$_4$H$_9$, 5-CH$_3$-phenyl | |
| 127 | 2,6-(t-C$_4$H$_9$)$_2$, 4-CH$_3$-phenyl | |
| 128 | 2-CH$_3$, 4-t-C$_4$H$_9$-phenyl | |
| 129 | 2-CH$_3$, 6-t-C$_4$H$_9$-phenyl | |
| 130 | 2-CH$_3$, 4-i-C$_3$H$_7$-phenyl | |
| 131 | 2-CH$_3$, 5-i-C$_3$H$_7$-phenyl | |
| 132 | 3-CH$_3$, 4-i-C$_3$H$_7$-phenyl | |
| 133 | 2-i-C$_3$H$_7$, 5-CH$_3$-phenyl | |
| 134 | 2,4-(t-C$_4$H$_9$)$_2$-6-i-C$_3$H$_7$-phenyl | |
| 135 | 2-cyclo-C$_6$H$_{11}$-phenyl | |
| 136 | 3-cyclo-C$_6$H$_{11}$-phenyl | |
| 137 | 4-cyclo-C$_6$H$_{11}$-phenyl | |
| 138 | 2,4-(cyclo-C$_6$H$_{11}$)$_2$-6-CH$_3$-phenyl | |
| 139 | 2-CH$_3$, 4-cyclo-C$_6$H$_{11}$-phenyl | |
| 140 | 2-CH$_2$C$_6$H$_5$-phenyl | |
| 141 | 3-CH$_2$C$_6$H$_5$-phenyl | |
| 142 | 4-CH$_2$C$_6$H$_5$-phenyl | |
| 143 | 2-CH$_2$C$_6$H$_5$, 4-CH$_3$-phenyl | |
| 144 | 2-CH$_3$, 4-CH$_2$C$_6$H$_5$-phenyl | |
| 145 | 2-C$_6$H$_5$-phenyl | |
| 146 | 3-C$_6$H$_5$-phenyl | |
| 147 | 4-C$_6$H$_5$-phenyl | |
| 148 | 4-(2-i-C$_3$H$_7$—C$_6$H$_4$)-phenyl | |
| 149 | 2-C$_6$H$_5$, 2,6-(CH$_3$)$_2$-phenyl | |
| 150 | 2-Cl, 4-C$_6$H$_5$-phenyl | |
| 151 | 2-Br, 4-C$_6$H$_5$-phenyl | |
| 152 | 2-C$_6$H$_5$, 4-Cl-phenyl | |
| 153 | 2-C$_6$H$_5$, 4-Br-phenyl | |
| 154 | 2-CH$_2$C$_6$H$_5$, 4-Cl-phenyl | |
| 155 | 2-CH$_2$C$_6$H$_5$, 4-Br-phenyl | |
| 156 | 2-Cl, 4-CH$_2$C$_6$H$_5$-phenyl | |
| 157 | 2-Br, 4-CH$_2$C$_6$H$_5$-phenyl | |
| 158 | 2-cyclo-C$_6$H$_{11}$, 4-Cl-phenyl | |
| 159 | 2-cyclo-C$_6$H$_{11}$, 4-Br-phenyl | |
| 160 | 2-Cl, 4-cyclo-C$_6$H$_{11}$-phenyl | |
| 161 | 2-Br, 4-cyclo-C$_6$H$_{11}$-phenyl | |
| 162 | 3-OCH$_3$-phenyl | |
| 163 | 2,4-(OCH$_3$)$_2$-phenyl | |
| 164 | 2-CF$_3$-phenyl | |
| 165 | 3-CF$_3$-phenyl | |
| 166 | 4-CF$_3$-phenyl | |
| 167 | 2-NO$_2$-phenyl | |
| 168 | 3-NO$_2$-phenyl | |
| 169 | 4-NO$_2$-phenyl | |
| 170 | 2-CN-phenyl | |
| 171 | 3-CN-phenyl | |
| 172 | 4-CN-phenyl | |
| 173 | 2-CH$_3$, 3-Cl-phenyl | |
| 174 | 2-CH$_3$, 4-Cl-phenyl | |
| 175 | 2-CH$_3$, 5-Cl-phenyl | |
| 176 | 2-CH$_3$, 6-Cl-phenyl | |
| 177 | 2-CH$_3$, 3-F-phenyl | |
| 178 | 2-CH$_3$, 4-F-phenyl | |
| 179 | 2-CH$_3$, 5-F-phenyl | |
| 180 | 2-CH$_3$, 6-F-phenyl | |
| 181 | 2-CH$_3$, 3-Br-phenyl | |
| 182 | 2-CH$_3$, 4-Br-phenyl | |
| 183 | 2-CH$_3$, 5-Br-phenyl | |
| 184 | 2-CH$_3$, 6-Br-phenyl | |
| 185 | 2-Cl, 3-CH$_3$-phenyl | |
| 186 | 2-Cl, 4-CH$_3$-phenyl | |
| 187 | 2-Cl, 5-CH$_3$-phenyl | |
| 188 | 2-Cl, 3-i-C$_3$H$_7$ | |
| 189 | 2-F, 3-CH$_3$-phenyl | |
| 190 | 2-F, 4-CH$_3$-phenyl | |

TABLE 11-continued

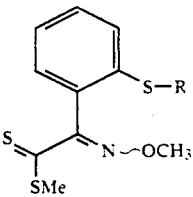

| No. | R | mp(°C.)/IR(cm$^{-1}$) |
|---|---|---|
| 191 | 2-F, 5-CH$_3$-phenyl | |
| 192 | 2-Br, 3-CH$_3$-phenyl | |
| 193 | 2-Br, 4-CH$_3$-phenyl | |
| 194 | 3-CH$_3$, 4-Cl-phenyl | |
| 195 | 3-CH$_3$, 5-Cl-phenyl | |
| 196 | 2-Br, 5-CH$_3$-phenyl | |
| 197 | 3-CH$_3$, 4-F-phenyl | |
| 198 | 3-CH$_3$, 5-F-phenyl | |
| 199 | 3-CH$_3$, 4-Br-phenyl | |
| 200 | 3-CH$_3$, 5-Br-phenyl | |
| 201 | 3-F, 4-CH$_3$-phenyl | |
| 202 | 3-Cl, 4-CH$_3$-phenyl | |
| 203 | 3-Br, 4-CH$_3$-phenyl | |
| 204 | 2-Cl, 4,5-(CH$_3$)$_2$-phenyl | |
| 205 | 2-Br, 4,5-(CH$_3$)$_2$-phenyl | |
| 206 | 2-Cl, 3,5-(CH$_3$)$_2$-phenyl | |
| 207 | 2-Br, 3,5-(CH$_3$)$_2$-phenyl | |
| 208 | 2,6-Cl$_2$, 4-CH$_3$-phenyl | |
| 209 | 2,6-F$_2$, 4-CH$_3$-phenyl | |
| 210 | 2,6-Br$_2$, 4-CH$_3$-phenyl | |
| 211 | 2,4-Cl$_2$, 6-CH$_3$-phenyl | |
| 212 | 2,4-F$_2$, 6-CH$_3$-phenyl | |
| 213 | 2,4-Br$_2$, 6-CH$_3$-phenyl | |
| 214 | 2,6-(CH$_3$)$_2$, 4-F-phenyl | |
| 215 | 2,6-(CH$_3$)$_2$, 4-Cl-phenyl | |
| 216 | 2,6-(CH$_3$)$_2$, 4-Br-phenyl | |
| 217 | 3,5-(CH$_3$)$_2$, 4-F-phenyl | |
| 218 | 3,5-(CH$_3$)$_2$, 4-Cl-phenyl | |
| 219 | 3,5-(CH$_3$)$_2$, 4-Br-phenyl | |
| 220 | 2,3,6-(CH$_3$)$_3$, 4-F-phenyl | |
| 221 | 2,3,6-(CH$_3$)$_3$, 4-Cl-phenyl | |
| 222 | 2,3,6-(CH$_3$)$_3$, 4-Br-phenyl | |
| 223 | 2,4-(CH$_3$)$_2$, 6-F-phenyl | |
| 224 | 2,4-(CH$_3$)$_2$, 6-Cl-phenyl | |
| 225 | 2,4-(CH$_3$)$_2$, 6-Br-phenyl | |
| 226 | 2-i-C$_3$H$_7$, 4-Cl, 5-CH$_3$-phenyl | |
| 227 | 2-Cl, 4-NO$_2$-phenyl | |
| 228 | 2-NO$_2$, 4-Cl-phenyl | |
| 229 | 2-OCH$_3$, 5-NO$_2$-phenyl | |
| 230 | 2,4-Cl$_2$, 5-NO$_2$-phenyl | |
| 231 | 2,4-Cl$_2$, 6-NO$_2$-phenyl | |
| 232 | 2,6-Cl$_2$, 4-NO$_2$-phenyl | |
| 233 | 2,6-Br$_2$, 4-NO$_2$-phenyl | |
| 234 | 2,6-I$_2$, 4-NO$_2$-phenyl | |
| 235 | 2-C$_6$H$_5$O-phenyl | |
| 236 | 3-C$_6$H$_5$O-phenyl | |
| 237 | 4-C$_6$H$_5$O-phenyl | |
| 238 | 3-t-C$_4$H$_9$O-phenyl | |
| 239 | 4-t-C$_4$H$_9$O-phenyl | |
| 240 | 1-naphthyl | |
| 241 | 2-naphthyl | |
| 242 | 2-pyridyl | |
| 243 | 6-methyl-2-pyridyl | |
| 244 | 6-ethyl-2-pyridyl | |
| 245 | 6-n-propyl-2-pyridyl | |
| 246 | 6-iso-propyl-2-pyridyl | |
| 247 | 6-n-butyl-2-pyridyl | |
| 248 | 6-tert.-butyl-2-pyridyl | |
| 249 | 6-n-pentyl-2-pyridyl | |
| 250 | 6-n-hexyl-2-pyridyl | |
| 251 | 6-phenyl-2-pyridyl | |
| 252 | 6-benzyl-2-pyridyl | |
| 253 | 6-trifluoromethyl-2-pyridyl | |
| 254 | 6-methoxy-2-pyridyl | |
| 255 | 6-chloro-2-pyridyl | |
| 256 | 3,6-dimethyl-2-pyridyl | |
| 257 | 3,6-diethyl-2-pyridyl | |
| 258 | 4,6-dimethyl-2-pyridyl | |
| 259 | 5,6-dimethyl-2-pyridyl | |
| 260 | 4-phenyl-6-methyl-2-pyridyl | |

TABLE 11-continued

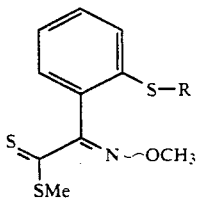

| No. | R | mp(°C.)/IR(cm$^{-1}$) |
|---|---|---|
| 261 | 4,6-diphenyl-2-pyridyl | |
| 262 | 3,4-dichloro-6-methyl-2-pyridyl | |
| 263 | 3,4,5-trichloro-6-phenyl-2-pyridyl | |
| 264 | 4-trifluoromethyl-6-methyl-2-pyridyl | |
| 265 | 3-cyano-6-methyl-2-pyridyl | |
| 266 | 3-cyano-6-ethyl-2-pyridyl | |
| 267 | 3-cyano-6-n-propyl-2-pyridyl | |
| 268 | 3-cyano-6-iso-propyl-2-pyridyl | |
| 269 | 3-cyano-6-cyclo-propyl-2-pyridyl | |
| 270 | 3-cyano-6-n-butyl-2-pyridyl | |
| 271 | 3-cyano-6-tert.-butyl-2-pyridyl | |
| 272 | 3-cyano-6-cyclo-hexyl-2-pyridyl | |
| 273 | 3-cyano-6-phenyl-2-pyridyl | |
| 274 | 3-cyano-4,6-dimethyl-2-pyridyl | |
| 275 | 3,5,6-trichloro-2-pyridyl | |
| 276 | 5-trifluoromethyl-2-pyridyl | |
| 277 | 3-chloro-5-trifluoromethyl-2-pyridyl | |
| 278 | 2-quinolyl | |
| 279 | 3-methyl-2-quinolyl | |
| 280 | 4-methyl-2-quinolyl | |
| 281 | 4-ethyl-2-quinolyl | |
| 282 | 4-phenyl-2-quinolyl | |
| 283 | 6-methyl-2-quinolyl | |
| 284 | 6-chloro-2-quinolyl | |
| 285 | 8-methyl-2-quinolyl | |
| 286 | 8-chloro-2-quinolyl | |
| 287 | 3,4-dimethyl-2-quinolyl | |
| 288 | 4-methyl-8-methoxy-2-quinolyl | |
| 289 | 4-phenyl-8-ethoxy-2-quinolyl | |
| 290 | 4-methyl-8-chloro-2-quinolyl | |
| 291 | 4-methyl-8-fluoro-2-quinolyl | |
| 292 | 4-quinolyl | |
| 293 | 2-methyl-4-quinolyl | |
| 294 | 2-trifluoromethyl-4-quinolyl | |
| 295 | 2-iso-propyl-4-quinolyl | |
| 296 | 2-n-pentyl-4-quinolyl | |
| 297 | 2-phenyl-4-quinolyl | |
| 298 | 2,6-dimethyl-4-quinolyl | |
| 299 | 2-methyl-6-chloro-4-quinolyl | |
| 300 | 2-methyl-6-fluoro-4-quinolyl | |
| 301 | 8-quinolyl | |
| 302 | 2-methyl-8-quinolyl | |
| 303 | 5,7-dichloro-8-quinolyl | |
| 304 | 4,6-dimethyl-2-pyrimidinyl | |
| 305 | 4-trifluoromethyl-2-pyrimidinyl | |
| 306 | 4,5,6-trimethyl-2-pyrimidinyl | |
| 307 | 4-benzyl-6-methyl-2-pyrimidinyl | |
| 308 | 4-methyl-6-phenyl-2-pyrimidinyl | |
| 309 | 4,6-dimethyl-5-chloro-2-pyrimidinyl | |
| 310 | 2,6-dimethyl-4-pyrimidinyl | |
| 311 | 2,6-bis-(trifluoromethyl)-4-pyrimidinyl | |
| 312 | 2-iso-propyl-6-methyl-4-pyrimidinyl | |
| 313 | 2-cyclo-propyl-6-methyl-4-pyrimidinyl | |
| 314 | 2-methyl-6-methoxymethyl-4-pyrimidinyl | |
| 315 | 2-iso-propyl-6-methoxymethyl-4-pyrimidinyl | |
| 316 | 2-phenyl-4-pyrimidinyl | |
| 317 | 3,5-dimethyl-4-pyrimidinyl | |
| 318 | 2-methyl-6-trifluoromethyl-4-pyrimidinyl | |
| 319 | 2-n-propyl-6-trifluoromethyl-4-pyrimidinyl | |
| 320 | 2-iso-propyl-6-trifluoromethyl-4-pyrimidinyl | |
| 321 | 2-methyl-5-chloro-6-trifluoromethyl-4-pyrimidinyl | |
| 322 | 2-n-propyl-5-chloro-6-trifluoromethyl-4-pyrimidinyl | |
| 323 | 2-iso-propyl-5-chloro-6-trifluoromethyl-4-pyrimidinyl | |
| 324 | 2-tert.-butyl-5-chloro-6-trifluoromethyl-4-pyrimidinyl | |
| 325 | 6-EtO-benzothiazol-2-yl | |
| 326 | benzoxazol-2-yl | |
| 327 | 1-Me-imidazol-2-yl | |
| 328 | 4-but-1H-imidazol-2-yl | |
| 329 | 2-thiazolin-2-yl | |
| 330 | 5-CF$_3$-benzimidazol-2-yl | |

TABLE 11-continued

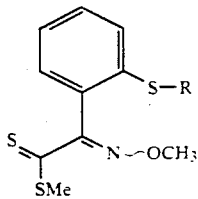

| No. | R | mp(°C.)/IR(cm$^{-1}$) |
|---|---|---|
| 331 | 1-Ph-tetrazol-5-yl | |
| 332 | 5-CF$_3$-benzothiazol-2-yl | |
| 333 | 4,4-Me$_2$-5-methylene-2-thiazolin-2-yl | |
| 334 | 6-Cl-4-Me-benzothiazol-2-yl | |
| 335 | 5-Me-benzothiazol-2-yl | |
| 336 | 4-Cl-benzothiazol-2-yl | |
| 337 | 1-(3-NO$_2$—Ph)tetrazol-5-yl | |
| 338 | 2-thienyl | |
| 339 | 5-Me-benzoxazol-2-yl | |
| 340 | 7-Cl-benzothiazol-2-yl | |
| 341 | 5,6-Cl$_3$-1H-benzimidazol-2-yl | |
| 342 | 5-Cl-benzoxazol-2-yl | |
| 343 | 6-Cl-benzothiazol-2-yl | |
| 344 | 2-Ph-thiazol-2-yl | |
| 345 | 3-CN-4,6-Me$_2$-2-pyridyl | |
| 346 | 1-Ph-1,2,4-triazol-3-yl | |
| 347 | 1-Pri-benzimidazol-2-yl | |
| 348 | 5-Br-benzothiazol-2-yl | |
| 349 | 5-Br-1H-benzimidazol-2-yl | |
| 350 | 7-Cl-4-MeO-benzothiazol-2-yl | |
| 351 | 1H-benzimidazol-2-yl | |
| 352 | 5-Cl-benzothiazol-2-yl | |
| 353 | 5-NO$_2$-benzoxazol-2-yl | |
| 354 | 5-t-Bu-benzoxazol-2-yl | |
| 355 | 4,6,7-Cl$_3$-benzothiozol-2-yl | |
| 356 | 5-Ph-thiazol-2-yl | |
| 357 | 5,7-Me$_2$-benzoxazol-2-yl | |
| 358 | 6-Me-benzoxazol-2-yl | |
| 359 | 1,2,4-triazin-3-yl | |
| 360 | 6-Pr-benzothiazol-2-yl | |
| 361 | 6-PhO-benzothiazol-2-yl | |
| 362 | 4-(4-Cl—Ph)-thiazol-2-yl | |
| 363 | 4-(4-Me—Ph)-thiazol-2-yl | |
| 364 | 5-Me-4-Ph-thiazol-2-yl | |
| 365 | 5-Cl-1-H-benzimidazol-2-yl | |
| 366 | 5-Ph-1,2,4-triazol-3-yl | |
| 367 | 3-Ph-1,2,4-thiadiazol-5-yl | |

TABLE 12

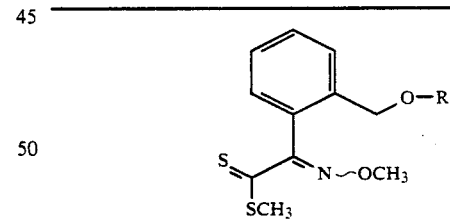

| No. | R | mp(°C.)/IR(cm$^{-1}$) |
|---|---|---|
| 1 | methyl | |
| 2 | ethyl | |
| 3 | n-propyl | |
| 4 | iso-propyl | |
| 5 | n-butyl | |
| 6 | s-butyl | |
| 7 | iso-butyl | |
| 8 | tert.-butyl | |
| 9 | pentyl | |
| 10 | hexyl | |
| 11 | phenyl | |
| 12 | 2-F-phenyl | |
| 13 | 3-F-phenyl | |
| 14 | 4-F-phenyl | |
| 15 | 2-Cl-phenyl | 58–60° C. |
| 16 | 3-Cl-phenyl | |
| 17 | 4-Cl-phenyl | |

TABLE 12-continued

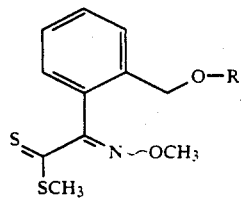

| No. | R | mp(°C.)/IR(cm$^{-1}$) |
|---|---|---|
| 18 | 2-Br-phenyl | |
| 19 | 3-Br-phenyl | |
| 20 | 4-Br-phenyl | |
| 21 | 2-I-phenyl | |
| 22 | 3-I-phenyl | |
| 23 | 4-I-phenyl | |
| 24 | 2-CH$_3$-phenyl | 1662, 1494, 1461, 1240, 1190, 1122, 1051, 1025, 845, 753 (cm$^{-1}$) |
| 25 | 2-CN-phenyl | |
| 26 | 3-CN-phenyl | |
| 27 | 4-CN-phenyl | |
| 28 | 2,3-F$_2$-phenyl | |
| 29 | 2,4-F$_2$-phenyl | |
| 30 | 2,3-Cl$_2$-phenyl | |
| 31 | 2,4-Cl$_2$-phenyl | |
| 32 | 2,5-Cl$_2$-phenyl | |
| 33 | 2,6-Cl$_2$-phenyl | |
| 34 | 3,4-Cl$_2$-phenyl | |
| 35 | 3,5-Cl$_2$-phenyl | |
| 36 | 2,4-Br$_2$-phenyl | |
| 37 | 2,5-Br$_2$-phenyl | |
| 38 | 2,6-Br$_2$-phenyl | |
| 39 | 2,4-I$_2$-phenyl | |
| 40 | 2-Cl, 3-F-phenyl | |
| 41 | 2-Cl, 4-F-phenyl | |
| 42 | 2-Cl, 5-F-phenyl | |
| 43 | 2-Cl, 6-F-phenyl | |
| 44 | 2-Cl, 3-Br-phenyl | |
| 45 | 2-Cl, 4-Br-phenyl | |
| 46 | 2-Cl, 5-Br-phenyl | |
| 47 | 2-Cl, 6-Br-phenyl | |
| 48 | 2-Br, 3-Cl-phenyl | |
| 49 | 2-Br, 4-Cl-phenyl | |
| 50 | 2-Br, 3-F-phenyl | |
| 51 | 2-Br, 4-F-phenyl | |
| 52 | 2-Br, 5-F-phenyl | |
| 53 | 2-Br, 6-F-phenyl | |
| 54 | 2-F, 3-Cl-phenyl | |
| 55 | 2-F, 4-Cl-phenyl | |
| 56 | 2-F, 5-Cl-phenyl | |
| 57 | 3-Cl, 4-F-phenyl | |
| 58 | 3-Cl, 5-F-phenyl | |
| 59 | 3-Cl, 4-Br-phenyl | |
| 60 | 3-Cl, 5-Br-phenyl | |
| 61 | 3-F, 4-Cl-phenyl | |
| 62 | 3-F, 4-Br-phenyl | |
| 63 | 3-Br, 4-Cl-phenyl | |
| 64 | 3-Br, 4-F-phenyl | |
| 65 | 2,4,6-F$_3$-phenyl | |
| 66 | 2,3,4,-Cl$_3$-phenyl | |
| 67 | 2,3,5-Cl$_3$-phenyl | |
| 68 | 2,3,6-Cl$_3$-phenyl | |
| 69 | 2,4,5-Cl$_3$-phenyl | |
| 70 | 2,4,6-Cl$_3$-phenyl | |
| 71 | 3,4,5-Cl$_3$-phenyl | |
| 72 | 2,4,6-Br$_3$-phenyl | |
| 73 | 2,6-Cl$_2$-4-Br-phenyl | |
| 74 | 2,3,4,6-Cl$_4$-phenyl | |
| 75 | 2,3,5,6-Cl$_4$-phenyl | |
| 76 | F$_5$-phenyl | |
| 77 | Cl$_5$-phenyl | |
| 78 | Br$_5$-phenyl | |
| 79 | 2-CH$_3$-phenyl | |
| 80 | 3-CH$_3$-phenyl | |
| 81 | 4-CH$_3$-phenyl | |
| 82 | 2-C$_2$H$_5$-phenyl | |
| 83 | 3-C$_2$H$_5$-phenyl | |
| 84 | 4-C$_2$H$_5$-phenyl | |

TABLE 12-continued

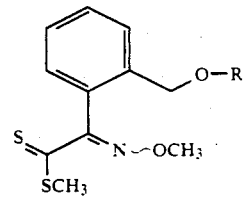

| No. | R | mp(°C.)/IR(cm$^{-1}$) |
|---|---|---|
| 85 | 2-n-C$_3$H$_7$-phenyl | |
| 86 | 3-n-C$_3$H$_7$-phenyl | |
| 87 | 4-n-C$_3$H$_7$-phenyl | |
| 88 | 2-i-C$_3$H$_7$-phenyl | |
| 89 | 3-i-C$_3$H$_7$-phenyl | |
| 90 | 4-i-C$_3$H$_7$-phenyl | |
| 91 | 2-s-C$_4$H$_9$-phenyl | |
| 92 | 3-s-C$_4$H$_9$-phenyl | |
| 93 | 4-s-C$_4$H$_9$-phenyl | |
| 94 | 2-t-C$_4$H$_9$-phenyl | |
| 95 | 3-t-C$_4$H$_9$-phenyl | |
| 96 | 4-t-C$_4$H$_9$-phenyl | |
| 97 | 2,3-(CH$_3$)$_2$-phenyl | |
| 98 | 2,4-(CH$_3$)$_2$-phenyl | |
| 99 | 2,5-(CH$_3$)$_2$-phenyl | |
| 100 | 2,6-(CH$_3$)$_2$-phenyl | |
| 101 | 3,4-(CH$_3$)$_2$-phenyl | |
| 102 | 3,5-(CH$_3$)$_2$-phenyl | |
| 103 | 2,3,4-(CH$_3$)$_3$-phenyl | |
| 104 | 2,3,5-(CH$_3$)$_3$-phenyl | |
| 105 | 2,3,6-(CH$_3$)$_3$-phenyl | |
| 106 | 2,4,5-(CH$_3$)$_3$-phenyl | |
| 107 | 2,4,6-(CH$_3$)$_3$-phenyl | |
| 108 | 3,4,5-(CH$_3$)$_3$-phenyl | |
| 109 | 2,3,4,6-(CH$_3$)$_4$-phenyl | |
| 110 | 2,3,5,6-(CH$_3$)$_4$-phenyl | |
| 111 | (CH$_3$)$_5$-phenyl | |
| 112 | 2,4-(C$_2$H$_5$)$_2$-phenyl | |
| 113 | 2,6-(C$_2$H$_5$)$_2$-phenyl | |
| 114 | 3,5-(C$_2$H$_5$)$_2$-phenyl | |
| 115 | 2,4,6-(C$_2$H$_5$)$_3$-phenyl | |
| 116 | 2,4-(i-C$_3$H$_7$)$_2$-phenyl | |
| 117 | 2,6-(i-C$_3$H$_7$)$_2$-phenyl | |
| 118 | 3,5-(i-C$_3$H$_7$)$_2$-phenyl | |
| 119 | 2,4,6-(i-C$_3$H$_7$)$_3$-phenyl | |
| 120 | 2,3-(t-C$_4$H$_9$)$_2$-phenyl | |
| 121 | 2,4-(t-C$_4$H$_9$)$_2$-phenyl | |
| 122 | 2,5-(t-C$_4$H$_9$)$_2$-phenyl | |
| 123 | 2,6-(t-C$_4$H$_9$)$_2$-phenyl | |
| 124 | 3,5-(t-C$_4$H$_9$)$_2$-phenyl | |
| 125 | 2,4,6-(t-C$_4$H$_9$)$_3$-phenyl | |
| 126 | 2-t-C$_4$H$_9$, 4-CH$_3$-phenyl | |
| 127 | 2-t-C$_4$H$_9$, 5-CH$_3$-phenyl | |
| 128 | 2,6-(t-C$_4$H$_9$)$_2$, 4-CH$_3$-phenyl | |
| 129 | 2-CH$_3$, 4-t-C$_4$H$_9$-phenyl | |
| 130 | 2-CH$_3$, 6-t-C$_4$H$_9$-phenyl | |
| 131 | 1-CH$_3$, 4-i-C$_3$H$_7$-phenyl | |
| 132 | 2-CH$_3$, 5-i-C$_3$H$_7$-phenyl | |
| 133 | 3-CH$_3$, 4-i-C$_3$H$_7$-phenyl | |
| 134 | 2-i-C$_3$H$_7$, 5-CH$_3$-phenyl | |
| 135 | 2,4-(t-C$_4$H$_9$)$_2$-6-i-C$_3$H$_7$-phenyl | |
| 136 | 2-cyclo-C$_6$H$_{11}$-phenyl | |
| 137 | 3-cyclo-C$_6$H$_{11}$-phenyl | |
| 138 | 4-cyclo-C$_6$H$_{11}$-phenyl | |
| 139 | 2,4-(cyclo-C$_6$H$_{11}$)$_2$-6-CH$_3$-phenyl | |
| 140 | 2-CH$_3$, 4-cyclo-C$_6$H$_{11}$-phenyl | |
| 141 | 2-CH$_2$C$_6$H$_5$-phenyl | |
| 142 | 3-CH$_2$C$_6$H$_5$-phenyl | |
| 143 | 4-CH$_2$C$_6$H$_5$-phenyl | |
| 144 | 2-CH$_2$C$_6$H$_5$, 4-CH$_3$-phenyl | |
| 145 | 2-CH$_3$, 4-CH$_2$C$_6$H$_5$-phenyl | |
| 146 | 2-C$_6$H$_5$-phenyl | |
| 147 | 3-C$_6$H$_5$-phenyl | |
| 148 | 4-C$_6$H$_5$-phenyl | |
| 149 | 4-(2-i-C$_3$H$_7$—C$_6$H$_4$)-phenyl | |
| 150 | 4-C$_6$H$_5$, 2,6-(CH$_3$)$_2$-phenyl | |
| 151 | 2-Cl, 4-C$_6$H$_5$-phenyl | |
| 152 | 2-Br, 4-C$_6$H$_5$-phenyl | |
| 153 | 2-C$_6$H$_5$, 4-Cl-phenyl | |
| 154 | 2-C$_6$H$_5$, 4-Br-phenyl | |

TABLE 12-continued

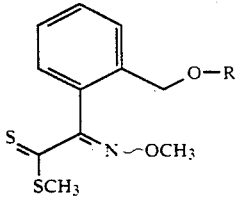

| No. | R | mp(°C.)/IR(cm⁻¹) |
|---|---|---|
| 155 | 2-CH₂C₆H₅, 4-Cl-phenyl | |
| 156 | 2-CH₂C₆H₅, 4-Br-phenyl | |
| 157 | 2-Cl, 4-CH₂C₆H₅-phenyl | |
| 158 | 2-Br, 4-CH₂C₆H₅-phenyl | |
| 159 | 2-cyclo-C₆H₁₁, 4-Cl-phenyl | |
| 160 | 2-cyclo-C₆H₁₁, 4-Br-phenyl | |
| 161 | 2-Cl, 4-cyclo-C₆H₁₁-phenyl | |
| 162 | 2-Br, 4-cyclo-C₆H₁₁-phenyl | |
| 163 | 3-OCH₃-phenyl | |
| 164 | 2,4-(OCH₃)₂-phenyl | |
| 165 | 2-CF₃-phenyl | |
| 166 | 3-CF₃-phenyl | |
| 167 | 4-CF₃-phenyl | |
| 168 | 2-NO₂-phenyl | |
| 169 | 3-NO₂-phenyl | |
| 170 | 4-NO₂-phenyl | |
| 171 | 2-CN-phenyl | |
| 172 | 3-CN-phenyl | |
| 173 | 4-CN-phenyl | |
| 174 | 2-CH₃, 3-Cl-phenyl | |
| 175 | 2-CH₃, 4-Cl-phenyl | |
| 176 | 2-CH₃, 5-Cl-phenyl | |
| 177 | 2-CH₃, 6-Cl-phenyl | |
| 178 | 2-CH₃, 3-F-phenyl | |
| 179 | 2-CH₃, 4-F-phenyl | |
| 180 | 2-CH₃, 5-F-phenyl | |
| 181 | 2-CH₃, 6-F-phenyl | |
| 182 | 2-CH₃, 3-Br-phenyl | |
| 183 | 2-CH₃, 4-Br-phenyl | |
| 184 | 2-CH₃, 5-Br-phenyl | |
| 185 | 2-CH₃, 6-Br-phenyl | |
| 186 | 2-Cl, 3-CH₃-phenyl | |
| 187 | 2-Cl, 4-CH₃-phenyl | |
| 188 | 2-Cl, 5-CH₃-phenyl | |
| 189 | 2-Cl, 3-i-C₃H₇ | |
| 190 | 2-F, 3-CH₃-phenyl | |
| 191 | 2-F, 4-CH₃-phenyl | |
| 192 | 2-F, 5-CH₃-phenyl | |
| 193 | 2-Br, 3-CH₃-phenyl | |
| 194 | 2-Br, 4-CH₃-phenyl | |
| 195 | 3-CH₃, 4-Cl-phenyl | |
| 196 | 3-CH₃, 5-Cl-phenyl | |
| 197 | 2-Br, 5-CH₃-phenyl | |
| 198 | 3-CH₃, 4-F-phenyl | |
| 199 | 3-CH₃, 5-F-phenyl | |
| 200 | 3-CH₃, 4-Br-phenyl | |
| 201 | 3-CH₃, 5-Br-phenyl | |
| 202 | 3-F, 4-CH₃-phenyl | |
| 203 | 3-Cl, 4-CH₃-phenyl | |
| 204 | 3-Br, 4-CH₃-phenyl | |
| 205 | 2-Cl, 4,5-(CH₃)₂-phenyl | |
| 206 | 2-Br, 4,5-(CH₃)₂-phenyl | |
| 207 | 2-Cl, 3,5-(CH₃)₂-phenyl | |
| 208 | 2-Br, 3,5-(CH₃)₂-phenyl | |
| 209 | 2,6-Cl₂, 4-CH₃-phenyl | |
| 210 | 2,6-F₂, 4-CH₃-phenyl | |
| 211 | 2,6-Br₂, 4-CH₃-phenyl | |
| 212 | 2,4-Cl₂, 6-CH₃-phenyl | |
| 213 | 2,4-F₂, 6-CH₃-phenyl | |
| 214 | 2,4-Br₂, 6-CH₃-phenyl | |
| 215 | 2,6-(CH₃)₂, 4-F-phenyl | |
| 216 | 2,6-(CH₃)₂, 4-Cl-phenyl | |
| 217 | 2,6-(CH₃)₂, 4-Br-phenyl | |
| 218 | 3,5-(CH₃)₂, 4-F-phenyl | |
| 219 | 3,5-(CH₃)₂, 4-Cl-phenyl | |
| 220 | 3,5-(CH₃)₂, 4-Br-phenyl | |
| 221 | 2,3,6-(CH₃)₃, 4-F-phenyl | |
| 222 | 2,3,6-(CH₃)₃, 4-Cl-phenyl | |
| 223 | 2,3,6-(CH₃)₃, 4-Br-phenyl | |
| 224 | 2,4-(CH₃)₂, 6-F-phenyl | |

TABLE 12-continued

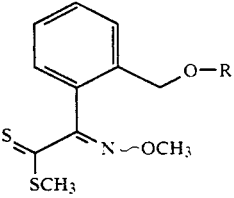

| No. | R | mp(°C.)/IR(cm⁻¹) |
|---|---|---|
| 225 | 2,4-(CH₃)₂, 6-Cl-phenyl | |
| 226 | 2,4-(CH₃)₂, 6-Br-phenyl | |
| 227 | 2-i-C₃H₇, 4-Cl, 5-CH₃-phenyl | |
| 228 | 2-Cl, 4-NO₂-phenyl | |
| 229 | 2-NO₂, 4-Cl-phenyl | |
| 230 | 2-OCH₃, 5-NO₂-phenyl | |
| 231 | 2,4-Cl₂, 5-NO₂-phenyl | |
| 232 | 2,4-Cl₂, 6-NO₂-phenyl | |
| 233 | 2,6-Cl₂, 4-NO₂-phenyl | |
| 234 | 2,6-Br₂, 4-NO₂-phenyl | |
| 235 | 2,6-I₂, 4-NO₂-phenyl | |
| 236 | 2-C₆H₅O-phenyl | |
| 237 | 3-C₆H₅O-phenyl | |
| 238 | 4-C₆H₅O-phenyl | |
| 239 | 3-t-C₄H₉O-phenyl | |
| 240 | 4-t-C₄H₉O-phenyl | |
| 241 | 1-naphthyl | |
| 242 | 2-naphthyl | |
| 243 | 2-pyridyl | |
| 244 | 6-methyl-2-pyridyl | |
| 245 | 6-ethyl-2-pyridyl | |
| 246 | 6-n-propyl-2-pyridyl | |
| 247 | 6-iso-propyl-2-pyridyl | |
| 248 | 6-n-butyl-2-pyridyl | |
| 249 | 6-tert.-butyl-2-pyridyl | |
| 250 | 6-n-pentyl-2-pyridyl | |
| 251 | 6-n-hexyl-2-pyridyl | |
| 252 | 6-phenyl-2-pyridyl | |
| 253 | 6-benzyl-2-pyridyl | |
| 254 | 6-trifluoromethyl-2-pyridyl | |
| 255 | 6-methoxy-2-pyridyl | |
| 256 | 6-chloro-2-pyridyl | |
| 257 | 3,6-dimethyl-2-pyridyl | |
| 258 | 3,6-diethyl-2-pyridyl | |
| 259 | 4,6-dimethyl-2-pyridyl | |
| 260 | 5,6-dimethyl-2-pyridyl | |
| 261 | 4-phenyl-6-methyl-2-pyridyl | |
| 262 | 4,6-diphenyl-2-pyridyl | |
| 263 | 3,4-dichloro-6-methyl-2-pyridyl | |
| 264 | 3,4,5-trichloro-6-phenyl-2-pyridyl | |
| 265 | 4-trifluoromethyl-6-methyl-2-pyridyl | |
| 266 | 3-cyano-6-methyl-2-pyridyl | |
| 267 | 3-cyano-6-ethyl-2-pyridyl | |
| 268 | 3-cyano-6-n-propyl-2-pyridyl | |
| 269 | 3-cyano-6-iso-propyl-2-pyridyl | |
| 270 | 3-cyano-6-cyclo-propyl-2-pyridyl | |
| 271 | 3-cyano-6-n-butyl-2-pyridyl | |
| 272 | 3-cyano-6-tert.-butyl-2-pyridyl | |
| 273 | 3-cyano-6-cyclo-hexyl-2-pyridyl | |
| 274 | 3-cyano-6-phenyl-2-pyridyl | |
| 275 | 3-cyano-4,6-dimethyl-2-pyridyl | |
| 276 | 3,5,6-trichloro-2-pyridyl | |
| 277 | 5-trifluoromethyl-2-pyridyl | |
| 278 | 3-chloro-5-trifluoromethyl-2-pyridyl | |
| 279 | 2-quinolyl | |
| 280 | 3-methyl-2-quinolyl | |
| 281 | 4-methyl-2-quinolyl | |
| 282 | 4-ethyl-2-quinolyl | |
| 283 | 4-phenyl-2-quinolyl | |
| 284 | 6-methyl-2-quinolyl | |
| 285 | 6-chloro-2-quinolyl | |
| 286 | 8-methyl-2-quinolyl | |
| 287 | 8-chloro-2-quinolyl | |
| 288 | 3,4-dimethyl-2-quinolyl | |
| 289 | 4-methyl-8-methoxy-2-quinolyl | |
| 290 | 4-phenyl-8-ethoxy-2-quinolyl | |
| 291 | 4-methyl-8-chloro-2-quinolyl | |
| 292 | 4-methyl-8-fluoro-2-quinolyl | |
| 293 | 4-quinolyl | |
| 294 | 2-methyl-4-quinolyl | |

TABLE 12-continued

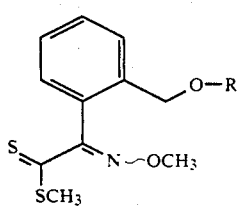

| No. | R | mp(°C.)/IR(cm⁻¹) |
|---|---|---|
| 295 | 2-trifluoromethyl-4-quinolyl | |
| 296 | 2-iso-propyl-4-quinolyl | |
| 297 | 2-n-pentyl-4-quinolyl | |
| 298 | 2-phenyl-4-quinolyl | |
| 299 | 2,6-dimethyl-4-quinolyl | |
| 300 | 2-methyl-6-chloro-4-quinolyl | |
| 301 | 2-methyl-6-fluoro-4-quinolyl | |
| 302 | 8-quinolyl | |
| 303 | 2-methyl-8-quinolyl | |
| 304 | 5,7-dichloro-8-quinolyl | |
| 305 | 4,6-dimethyl-2-pyrimidinyl | |
| 306 | 4-trifluoromethyl-2-pyrimidinyl | |
| 307 | 4,5,6-trimethyl-2-pyrimidinyl | |
| 308 | 4-benzyl-6-methyl-2-pyrimidinyl | |
| 309 | 4-methyl-6-phenyl-2-pyrimidinyl | |
| 310 | 4,6-dimethyl-5-chloro-2-pyrimidinyl | |
| 311 | 2,6-dimethyl-4-pyrimidinyl | |
| 312 | 2,6-bis-(trifluoromethyl)-4-pyrimidinyl | |
| 313 | 2-iso-propyl-6-methyl-4-pyrimidinyl | |
| 314 | 2-cyclo-propyl-6-methyl-4-pyrimidinyl | |
| 315 | 2-methyl-6-methoxymethyl-4-pyrimidinyl | |
| 316 | 2-iso-propyl-6-methoxymethyl-4-pyrimidinyl | |
| 317 | 2-phenyl-4-pyrimidinyl | |
| 318 | 3,5-dimethyl-4-pyrimidinyl | |
| 319 | 2-methyl-6-trifluoromethyl-4-pyrimidinyl | |
| 320 | 2-n-propyl-6-trifluoromethyl-4-pyrimidinyl | |
| 321 | 2-iso-propyl-6-trifluoromethyl-4-pyrimidinyl | |
| 322 | 2-methyl-5-chloro-6-trifluoromethyl-4-pyrimidinyl | |
| 323 | 2-n-propyl-5-chloro-6-trifluoromethyl-4-pyrimidinyl | |
| 324 | 2-iso-propyl-5-chloro-6-trifluoromethyl-4-pyrimidinyl | |
| 325 | 2-tert.-butyl-5-chloro-6-trifluoromethyl-4-pyrimidinyl | |

TABLE 13

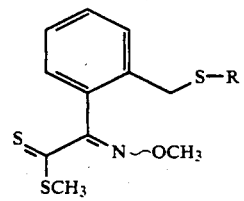

| No. | R | mp(°C.)/IR (cm⁻¹) |
|---|---|---|
| 1 | methyl | |
| 2 | ethyl | |
| 3 | n-propyl | |
| 4 | iso-propyl | |
| 5 | n-butyl | |
| 6 | s-butyl | |
| 7 | iso-butyl | |
| 8 | tert.-butyl | |
| 9 | pentyl | |
| 10 | hexyl | |
| 11 | phenyl | |
| 12 | 2-F-phenyl | |
| 13 | 3-F-phenyl | |
| 14 | 4-F-phenyl | |
| 15 | 2-Cl-phenyl | 1661, 1451, 1443, 1139, 1115, 1043, 1035, 1024, 846, 749 |
| 16 | 3-Cl-phenyl | |
| 17 | 4-Cl-phenyl | |
| 18 | 2-Br-phenyl | |
| 19 | 3-Br-phenyl | |
| 20 | 4-Br-phenyl | |
| 21 | 2-I-phenyl | |
| 22 | 3-I-phenyl | |
| 23 | 4-I-phenyl | |
| 24 | 2-CN-phenyl | |
| 25 | 3-CN-phenyl | |
| 26 | 4-CN-phenyl | |
| 27 | 2,3-F₂-phenyl | |
| 28 | 2,4-F₂-phenyl | |
| 29 | 2,3-Cl₂-phenyl | |
| 30 | 2,4-Cl₂-phenyl | |
| 31 | 2,5-Cl₂-phenyl | |
| 32 | 2,6-Cl₂-phenyl | |
| 33 | 3,4-Cl₂-phenyl | |
| 34 | 3,5-Cl₂-phenyl | |
| 35 | 2,4-Br₂-phenyl | |
| 36 | 2,5-Br₂-phenyl | |
| 37 | 2,6-Br₂-phenyl | |
| 38 | 2,4-I₂-phenyl | |
| 39 | 2-Cl, 3-F-phenyl | |
| 40 | 2-Cl, 4-F-phenyl | |
| 41 | 2-Cl, 5-F-phenyl | |
| 42 | 2-Cl, 6-F-phenyl | |
| 43 | 2-Cl, 3-Br-phenyl | |
| 44 | 2-Cl, 4-Br-phenyl | |
| 45 | 2-Cl, 5-Br-phenyl | |
| 46 | 2-Cl, 6-Br-phenyl | |
| 47 | 2-Br, 3-Cl-phenyl | |
| 48 | 2-Br, 4-Cl-phenyl | |
| 49 | 2-Br, 3-F-phenyl | |
| 50 | 2-Br, 4-F-phenyl | |
| 51 | 2-Br, 5-F-phenyl | |
| 52 | 2-Br, 6-F-phenyl | |
| 53 | 2-F, 3-Cl-phenyl | |
| 54 | 2-F, 4-Cl-phenyl | |
| 55 | 2-F, 5-Cl-phenyl | |
| 56 | 3-Cl, 4-F-phenyl | |
| 57 | 3-Cl, 5-F-phenyl | |
| 58 | 3-Cl, 4-Br-phenyl | |
| 59 | 3-Cl, 5-Br-phenyl | |
| 60 | 3-F, 4-Cl-phenyl | |
| 61 | 3-F, 4-Br-phenyl | |
| 62 | 3-Br, 4-Cl-phenyl | |
| 63 | 3-Br, 4-F-phenyl | |
| 64 | 2,4,6-F₃-phenyl | |
| 65 | 2,3,4-Cl₃-phenyl | |
| 66 | 2,3,5-Cl₃-phenyl | |
| 67 | 2,3,6-Cl₃-phenyl | |
| 68 | 2,4,5-Cl₃-phenyl | |
| 69 | 2,4,6-Cl₃-phenyl | |
| 70 | 3,4,5-Cl₃-phenyl | |
| 71 | 2,4,6-Br₃-phenyl | |
| 72 | 2,6-Cl₂-4-Br-phenyl | |
| 73 | 2,3,4,6-Cl₄-phenyl | |
| 74 | 2,3,5,6-Cl₄-phenyl | |
| 75 | F₅-phenyl | |
| 76 | Cl₅-phenyl | |
| 77 | Br₅-phenyl | |

TABLE 13-continued

[Structure: 2-position of phenyl ring bears CH₂-S-R; the ring also bears C(=NOCH₃)-C(=S)-SCH₃]

| No. | R | mp(°C.)/IR (cm⁻¹) |
|---|---|---|
| 78 | 2-CH₃-phenyl | |
| 79 | 3-CH₃-phenyl | |
| 80 | 4-CH₃-phenyl | |
| 81 | 2-C₂H₅-phenyl | |
| 82 | 3-C₂H₅-phenyl | |
| 83 | 4-C₂H₅-phenyl | |
| 84 | 2-n-C₃H₇-phenyl | |
| 85 | 3-n-C₃H₇-phenyl | |
| 86 | 4-n-C₃H₇-phenyl | |
| 87 | 2-i-C₃H₇-phenyl | |
| 88 | 3-i-C₃H₇-phenyl | |
| 89 | 4-i-C₃H₇-phenyl | |
| 90 | 2-s-C₄H₉-phenyl | |
| 91 | 3-s-C₄H₉-phenyl | |
| 92 | 4-s-C₄H₉-phenyl | |
| 93 | 2-t-C₄H₉-phenyl | |
| 94 | 3-t-C₄H₉-phenyl | |
| 95 | 4-t-C₄H₉-phenyl | |
| 96 | 2,3-(CH₃)₂-phenyl | |
| 97 | 2,4-(CH₃)₂-phenyl | |
| 98 | 2,5-(CH₃)₂-phenyl | |
| 99 | 2,6-(CH₃)₂-phenyl | |
| 100 | 3,4-(CH₃)₂-phenyl | |
| 101 | 3,5-(CH₃)₂-phenyl | |
| 102 | 2,3,4-(CH₃)₃-phenyl | |
| 103 | 2,3,5-(CH₃)₃-phenyl | |
| 104 | 2,3,6-(CH₃)₃-phenyl | |
| 105 | 2,4,5-(CH₃)₃-phenyl | |
| 106 | 2,4,6-(CH₃)₃-phenyl | |
| 107 | 3,4,5-(CH₃)₃-phenyl | |
| 108 | 2,3,4,6-(CH₃)₄-phenyl | |
| 109 | 2,3,5,6-(CH₃)₄-phenyl | |
| 110 | (CH₃)₅-phenyl | |
| 111 | 2,4-(C₂H₅)₂-phenyl | |
| 112 | 2,6-(C₂H₅)₂-phenyl | |
| 113 | 3,5-(C₂H₅)₂-phenyl | |
| 114 | 2,4,6-(C₂H₅)₃-phenyl | |
| 115 | 2,4-(i-C₃H₇)₂-phenyl | |
| 116 | 2,6-(i-C₃H₇)₂-phenyl | |
| 117 | 3,5-(i-C₃H₇)₂-phenyl | |
| 118 | 2,4,6-(i-C₃H₇)₃-phenyl | |
| 119 | 2,3-(t-C₄H₉)₂-phenyl | |
| 120 | 2,4-(t-C₄H₉)₂-phenyl | |
| 121 | 2,5-(t-C₄H₉)₂-phenyl | |
| 122 | 2,6-(t-C₄H₉)₂-phenyl | |
| 123 | 3,5-(t-C₄H₉)₂-phenyl | |
| 124 | 2,4,6-(t-C₄H₉)₃-phenyl | |
| 125 | 2-t-C₄H₉, 4-CH₃-phenyl | |
| 126 | 2-t-C₄H₉, 5-CH₃-phenyl | |
| 127 | 2,6-(t-C₄H₉)₂, 4-CH₃-phenyl | |
| 128 | 2-CH₃, 4-t-C₄H₉-phenyl | |
| 129 | 2-CH₃, 6-t-C₄H₉-phenyl | |
| 130 | 2-CH₃, 4-i-C₃H₇-phenyl | |
| 131 | 2-CH₃, 5-i-C₃H₇-phenyl | |
| 132 | 3-CH₃, 4-i-C₃H₇-phenyl | |
| 133 | 2-i-C₃H₇, 5-CH₃-phenyl | |
| 134 | 2,4-(t-C₄H₉)₂-6-i-C₃H₇-phenyl | |
| 135 | 2-cyclo-C₆H₁₁-phenyl | |
| 136 | 3-cyclo-C₆H₁₁-phenyl | |
| 137 | 4-cyclo-C₆H₁₁-phenyl | |
| 138 | 2,4-(cyclo-C₆H₁₁)₂-6-CH₃-phenyl | |
| 139 | 2-CH₃, 4-cyclo-C₆H₁₁-phenyl | |
| 140 | 2-CH₂C₆H₅-phenyl | |
| 141 | 3-CH₂C₆H₅-phenyl | |
| 142 | 4-CH₂C₆H₅-phenyl | |
| 143 | 2-CH₂C₆H₅, 4-CH₃-phenyl | |
| 144 | 2-CH₃, 4-CH₂C₆H₅-phenyl | |
| 145 | 2-C₆H₅-phenyl | |
| 146 | 3-C₆H₅-phenyl | |
| 147 | 4-C₆H₅-phenyl | |
| 148 | 4-(2-i-C₃H₇—C₆H₄)-phenyl | |
| 149 | 4-C₆H₅, 2,6-(CH₃)₂-phenyl | |
| 150 | 2-Cl, 4-C₆H₅-phenyl | |
| 151 | 2-Br, 4-C₆H₅-phenyl | |
| 152 | 2-C₆H₅, 4-Cl-phenyl | |
| 153 | 2-C₆H₅, 4-Br-phenyl | |
| 154 | 2-CH₂C₆H₅, 4-Cl-phenyl | |
| 155 | 2-CH₂C₆H₅, 4-Br-phenyl | |
| 156 | 2-Cl, 4-CH₂C₆H₅-phenyl | |
| 157 | 2-Br, 4-CH₂C₅H₅-phenyl | |
| 158 | 2-cyclo-C₆H₁₁, 4-Cl-phenyl | |
| 159 | 2-cyclo-C₆H₁₁, 4-Br-phenyl | |
| 160 | 2-Cl, 4-cyclo-C₆H₁₁-phenyl | |
| 161 | 2-Br, 4-cyclo-C₆H₁₁-phenyl | |
| 162 | 3-OCH₃-phenyl | |
| 163 | 2,4-(OCH₃)₂-phenyl | |
| 164 | 2-CF₃-phenyl | |
| 165 | 3-CF₃-phenyl | |
| 166 | 4-CF₃-phenyl | |
| 167 | 2-NO₂-phenyl | |
| 168 | 3-NO₂-phenyl | |
| 169 | 4-NO₂-phenyl | |
| 170 | 2-CN-phenyl | |
| 171 | 3-CN-phenyl | |
| 172 | 4-CN-phenyl | |
| 173 | 2-CH₃, 3-Cl-phenyl | |
| 174 | 2-CH₃, 4-Cl-phenyl | |
| 175 | 2-CH₃, 5-Cl-phenyl | |
| 176 | 2-CH₃, 6-Cl-phenyl | |
| 177 | 2-CH₃, 3-F-phenyl | |
| 178 | 2-CH₃, 4-F-phenyl | |
| 179 | 2-CH₃, 5-F-phenyl | |
| 180 | 2-CH₃, 6-F-phenyl | |
| 181 | 2-CH₃, 3-Br-phenyl | |
| 182 | 2-CH₃, 4-Br-phenyl | |
| 183 | 2-CH₃, 5-Br-phenyl | |
| 184 | 2-CH₃, 6-Br-phenyl | |
| 185 | 2-Cl, 3-CH₃-phenyl | |
| 186 | 2-Cl, 4-CH₃-phenyl | |
| 187 | 2-Cl, 5-CH₃-phenyl | |
| 188 | 2-Cl, 3-i-C₃H₇ | |
| 189 | 2-F, 3-CH₃-phenyl | |
| 190 | 2-F, 4-CH₃-phenyl | |
| 191 | 2-F, 5-CH₃-phenyl | |
| 192 | 2-Br, 3-CH₃-phenyl | |
| 193 | 2-Br, 4-CH₃-phenyl | |
| 194 | 3-CH₃, 4-Cl-phenyl | |
| 195 | 3-CH₃, 5-Cl-phenyl | |
| 196 | 2-Br, 5-CH₃-phenyl | |
| 197 | 3-CH₃, 4-F-phenyl | |
| 198 | 3-CH₃, 5-F-phenyl | |
| 199 | 3-CH₃, 4-Br-phenyl | |
| 200 | 3-CH₃, 5-Br-phenyl | |
| 201 | 3-F, 4-CH₃-phenyl | |
| 202 | 3-Cl, 4-CH₃-phenyl | |
| 203 | 3-Br, 4-CH₃-phenyl | |
| 204 | 2-Cl, 4,5-(CH₃)₂-phenyl | |
| 205 | 2-Br, 4,5-(CH₃)₂-phenyl | |
| 206 | 2-Cl, 3,5-(CH₃)₂-phenyl | |
| 207 | 2-Br, 3,5-(CH₃)₂-phenyl | |
| 208 | 2,6-Cl₂, 4-CH₃-phenyl | |
| 209 | 2,6-F₂, 4-CH₃-phenyl | |
| 210 | 2,6-Br₂, 4-CH₃-phenyl | |
| 211 | 2,4-Cl₂, 6-CH₃-phenyl | |
| 212 | 2,4-F₂, 6-CH₃-phenyl | |
| 213 | 2,4-Br₂, 6-CH₃-phenyl | |
| 214 | 2,6-(CH₃)₂, 4-F-phenyl | |
| 215 | 2,6-(CH₃)₂, 4-Cl-phenyl | |

TABLE 13-continued

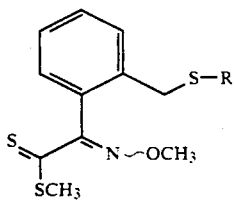

| No. | R | mp(°C.)/IR (cm$^{-1}$) |
|---|---|---|
| 216 | 2,6-(CH$_3$)$_2$, 4-Br-phenyl | |
| 217 | 3,5-(CH$_3$)$_2$, 4-F-phenyl | |
| 218 | 3,5-(CH$_3$)$_2$, 4-Cl-phenyl | |
| 219 | 3,5-(CH$_3$)$_2$, 4-Br-phenyl | |
| 220 | 2,3,6-(CH$_3$)$_3$, 4-F-phenyl | |
| 221 | 2,3,6-(CH$_3$)$_3$, 4-Cl-phenyl | |
| 222 | 2,3,6-(CH$_3$)$_3$, 4-Br-phenyl | |
| 223 | 2,4-(CH$_3$)$_2$, 6-F-phenyl | |
| 224 | 2,4-(CH$_3$)$_2$, 6-Cl-phenyl | |
| 225 | 2,4-(CH$_3$)$_2$, 6-Br-phenyl | |
| 226 | 2-i-C$_3$H$_7$, 4-Cl, 5-CH$_3$-phenyl | |
| 227 | 2-Cl, 4-NO$_2$-phenyl | |
| 228 | 2-NO$_2$, 4-Cl-phenyl | |
| 229 | 2-OCH$_3$, 5-NO$_2$-phenyl | |
| 230 | 2,4-Cl$_2$, 5-NO$_2$-phenyl | |
| 231 | 2,4-Cl$_2$, 6-NO$_2$-phenyl | |
| 232 | 2,6-Cl$_2$, 4-NO$_2$-phenyl | |
| 233 | 2,6-Br$_2$, 4-NO$_2$-phenyl | |
| 234 | 2,6-I$_2$, 4-NO$_2$-phenyl | |
| 235 | 2-C$_6$H$_5$O-phenyl | |
| 236 | 3-C$_6$H$_5$O-phenyl | |
| 237 | 4-C$_6$H$_5$O-phenyl | |
| 238 | 3-t-C$_4$H$_9$O-phenyl | |
| 239 | 4-t-C$_4$H$_9$O-phenyl | |
| 240 | 1-napthyl | |
| 241 | 2-napthyl | |
| 242 | 2-pyridyl | |
| 243 | 6-methyl-2-pyridyl | 89–94° C. |
| 244 | 6-ethyl-2-pyridyl | |
| 245 | 6-n-propyl-2-pyridyl | |
| 246 | 6-iso-propyl-2-pyridyl | |
| 247 | 6-n-butyl-2-pyridyl | |
| 248 | 6-tert.-butyl-2-pyridyl | |
| 249 | 6-n-pentyl-2-pyridyl | |
| 250 | 6-n-hexyl-2-pyridyl | |
| 251 | 6-phenyl-2-pyridyl | |
| 252 | 6-benzyl-2-pyridyl | |
| 253 | 6-trifluoromethyl-2-pyridyl | |
| 254 | 6-methoxy-2-pyridyl | |
| 255 | 6-chloro-2-pyridyl | |
| 256 | 3,6-dimethyl-2-pyridyl | |
| 257 | 3,6-diethyl-2-pyridyl | |
| 258 | 4,6-dimethyl-2-pyridyl | |
| 259 | 5,6-dimethyl-2-pyridyl | |
| 260 | 4-phenyl-6-methyl-2-pyridyl | |
| 261 | 4,6-diphenyl-2-pyridyl | |
| 262 | 3,4-dichloro-6-methyl-2-pyridyl | |
| 263 | 3,4,5-trichloro-6-phenyl-2-pyridyl | |
| 264 | 4-trifluoromethyl-6-methyl-2-pyridyl | |
| 265 | 3-cyano-6-methyl-2-pyridyl | |
| 266 | 3-cyano-6-ethyl-2-pyridyl | |
| 267 | 3-cyano-6-n-propyl-2-pyridyl | |
| 268 | 3-cyano-6-iso-propyl-2-pyridyl | |
| 269 | 3-cyano-6-cyclo-propyl-2-pyridyl | |
| 270 | 3-cyano-6-n-butyl-2-pyridyl | |
| 271 | 3-cyano-6-tert.-butyl-2-pyridyl | |
| 272 | 3-cyano-6-cyclo-hexyl-2-pyridyl | |
| 273 | 3-cyano-6-phenyl-2-pyridyl | |
| 274 | 3-cyano-4,6-dimethyl-2-pyridyl | |
| 275 | 3,5,6-trichloro-2-pyridyl | |
| 276 | 5-trifluoromethyl-2-pyridyl | |
| 277 | 3-chloro-5-trifluoromethyl-2-pyridyl | |
| 278 | 2-quinolyl | |
| 279 | 3-methyl-2-quinolyl | |
| 280 | 4-methyl-2-quinolyl | |
| 281 | 4-ethyl-2-quinolyl | |
| 282 | 4-phenyl-2-quinolyl | |
| 283 | 6-methyl-2-quinolyl | |
| 284 | 6-chloro-2-quinolyl | |

TABLE 13-continued

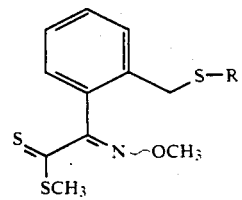

| No. | R | mp(°C.)/IR (cm$^{-1}$) |
|---|---|---|
| 285 | 8-methyl-2-quinolyl | |
| 286 | 8-chloro-2-quinolyl | |
| 287 | 3,4-dimethyl-2-quinolyl | |
| 288 | 4-methyl-8-methoxy-2-quinolyl | |
| 289 | 4-phenyl-8-ethoxy-2-quinolyl | |
| 290 | 4-methyl-8-chloro-2-quinolyl | |
| 291 | 4-methyl-8-fluoro-2-quinolyl | |
| 292 | 4-quinolyl | |
| 293 | 2-methyl-4-quinolyl | |
| 294 | 2-trifluoromethyl-4-quinolyl | |
| 295 | 2-iso-propyl-4-quinolyl | |
| 296 | 2-n-pentyl-4-quinolyl | |
| 297 | 2-phenyl-4-quinolyl | |
| 298 | 2,6-dimethyl-4-quinolyl | |
| 299 | 2-methyl-6-chloro-4-quinolyl | |
| 300 | 2-methyl-6-fluoro-4-quinolyl | |
| 301 | 8-quinolyl | |
| 302 | 2-methyl-8-quinolyl | |
| 303 | 5,7-dichloro-8-quinolyl | |
| 304 | 4,6-dimethyl-2-pyrimidinyl | |
| 305 | 4-trifluoromethyl-2-pyrimidinyl | |
| 306 | 4,5,6-trimethyl-2-pyrimidinyl | |
| 307 | 4-benzyl-6-methyl-2-pyrimidinyl | |
| 308 | 4-methyl-6-phenyl-2-pyrimidinyl | |
| 309 | 4,6-dimethyl-5-chloro-2-pyrimidinyl | |
| 310 | 2,6-dimethyl-4-pyrimidinyl | |
| 311 | 2,6-bis-(trifluoromethyl)-4-pyrimidinyl | |
| 312 | 2-iso-propyl-6-methyl-4-pyrimidinyl | |
| 313 | 2-cyclo-propyl-6-methyl-4-pyrimidinyl | |
| 314 | 2-methyl-6-methoxymethyl-4-pyrimidinyl | |
| 315 | 2-iso-propyl-6-methoxymethyl-4-pyrimidinyl | |
| 316 | 2-phenyl-4-pyrimidinyl | |
| 317 | 3,5-dimethyl-4-pyrimidinyl | |
| 318 | 2-methyl-6-trifluoromethyl-4-pyrimidinyl | |
| 319 | 2-n-propyl-6-trifluoromethyl-4-pyrimidinyl | |
| 320 | 2-iso-propyl-6-trifluoromethyl-4-pyrimidinyl | |
| 321 | 2-methyl-5-chloro-6-trifluoromethyl-4-pyrimidinyl | |
| 322 | 2-n-propyl-5-chloro-6-trifluoromethyl-4-pyrimidinyl | |
| 323 | 2-iso-propyl-5-chloro-6-trifluoromethyl-4-pyrimidinyl | |
| 324 | 2-tert.-butyl-5-chloro-6-trifluoromethyl-4-pyrimidinyl | |
| 325 | 6-EtO-benzothiazol-2-yl | |
| 326 | benzoxazol-2-yl | |
| 327 | 1-Me-imidazol-2-yl | |
| 328 | 4-but-1H-imidazol-2-yl | |
| 329 | 2-thiazolin-2-yl | |
| 330 | 5-CF$_3$-benzimidazol-2-yl | |
| 331 | 1-Ph-tetrazol-5-yl | |
| 332 | 5-CF$_3$-benzothiazol-2-yl | |
| 333 | 4,4-Me$_2$-5-methylene-2-thiazolin-2-yl | |
| 334 | 6-Cl-4-Me-benzothiazol-2-yl | |
| 335 | 5-Me-benzothiazol-2-yl | |
| 336 | 4-Cl-benzothiazol-2-yl | |
| 337 | 1-(3-NO$_2$—Ph)tetrazol-5-yl | |
| 338 | 2-thienyl | |
| 339 | 5-Me-benzoxazol-2-yl | |
| 340 | 7-Cl-benzothiazol-2-yl | |
| 341 | 5,6-Cl$_3$-1H-benzimidazol-2-yl | |
| 342 | 5-Cl-benzoxazol-2-yl | |
| 343 | 6-Cl-benzothiazol-2-yl | |
| 344 | 2-Ph-thiazol-2-yl | |
| 345 | 3-CN-4,6-Me$_2$-2-pyridyl | |
| 346 | 1-Ph-1,2,4-triazol-3-yl | |
| 347 | 1-Pri-benzimidazol-2-yl | |
| 348 | 5-Br-benzothiazol-2-yl | |
| 349 | 5-Br-1H-benzimidazol-2-yl | |

TABLE 13-continued

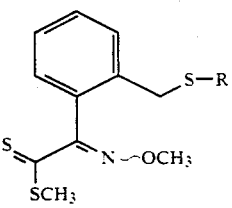

| No. | R | mp(°C.)/IR (cm⁻¹) |
|---|---|---|
| 350 | 7-Cl-4-MeO-benzothiazol-2-yl | |
| 351 | 1H-benzimidazol-2-yl | |
| 352 | 5-Cl-benzothiazol-2-yl | |
| 353 | 5-$NO_2$-benzoxazol-2-yl | |
| 354 | 5-t-Bu-benzoxazol-2-yl | |
| 355 | 4,6,7-$Cl_3$-benzothiozol-2-yl | |
| 356 | 5-Ph-thiazol-2-yl | |
| 357 | 5,7-$Me_2$-benzoxazol-2-yl | |
| 358 | 6-Me-benzoxazol-2-yl | |
| 359 | 1,2,4-triazin-3-yl | |
| 360 | 6-Pr-benzothiazol-2-yl | |
| 361 | 6-PhO-benzothiazol-2-yl | |
| 362 | 4-(4-Cl—Ph)-thiazol-2-yl | |
| 363 | 4-(4-Me—Ph)-thiazol-2-yl | |
| 364 | 5-Me-4-Ph-thiazol-2-yl | |
| 365 | 5-Cl-1-H-benzimidazol-2-yl | |
| 366 | 5-Ph-1,2,4-triazol-3-yl | |
| 367 | 3-Ph-1,2,4-thiadiazol-5-yl | |

TABLE 14

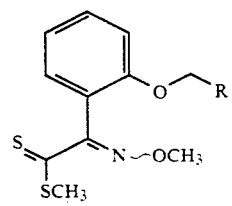

| No. | R | mp(°C.)/IR(cm⁻¹) |
|---|---|---|
| 1 | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-$NO_2$-phenyl | |
| 29 | 3-$NO_3$-phenyl | |
| 30 | 4-$NO_2$-phenyl | |
| 31 | 2-$CH_3$-phenyl | |
| 32 | 3-$CH_3$-phenyl | |
| 33 | 4-$CH_3$-phenyl | |
| 34 | 2-OMe-phenyl | |

TABLE 14-continued

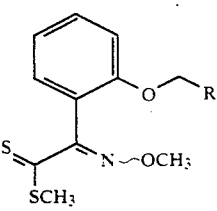

| No. | R | mp(°C.)/IR(cm⁻¹) |
|---|---|---|
| 35 | 3-OMe-phenyl | |
| 36 | 4-OMe-phenyl | |
| 37 | 2-$CF_3$-phenyl | |
| 38 | 3-$CF_3$-phenyl | |
| 39 | 4-$CF_3$-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |
| 50 | 2-thienyl | |
| 51 | 2-furyl | |
| 52 | 2-imidazolyl | |

TABLE 15

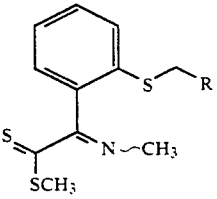

| No. | R | mp(°C.)/IR(cm⁻¹) |
|---|---|---|
| 1 | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-$NO_2$-phenyl | |
| 29 | 3-$NO_3$-phenyl | |
| 30 | 4-$NO_2$-phenyl | |
| 31 | 2-$CH_3$-phenyl | |
| 32 | 3-$CH_3$-phenyl | |
| 33 | 4-$CH_3$-phenyl | |
| 34 | 2-OMe-phenyl | |
| 35 | 3-OMe-phenyl | |

TABLE 15-continued

Structure: 2-(SCH2R)-phenyl group with C(=S)(SCH3)=N-CH3 substituent

| No. | R | mp(°C.)/IR(cm⁻¹) |
|---|---|---|
| 36 | 4-OMe-phenyl | |
| 37 | 2-CF₃-phenyl | |
| 38 | 3-CF₃-phenyl | |
| 39 | 4-CF₃-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |
| 50 | 2-thienyl | |
| 51 | 2-furyl | |
| 52 | 2-imidazolyl | |

TABLE 16

Structure: 2-(CH2CH2R)-phenyl group with C(=S)(SCH3)=N-OCH3 substituent

| No. | R | mp (°C.) IR (cm⁻¹) |
|---|---|---|
| 1 | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-NO₂-phenyl | |
| 29 | 3-NO₃-phenyl | |
| 30 | 4-NO₂-phenyl | |
| 31 | 2-CH₃-phenyl | |
| 32 | 3-CH₃-phenyl | |
| 33 | 4-CH₃-phenyl | |
| 34 | 2-OMe-phenyl | |
| 35 | 3-OMe-phenyl | |

TABLE 16-continued

Structure: 2-(CH2CH2R)-phenyl group with C(=S)(SCH3)=N-OCH3 substituent

| No. | R | mp (°C.) IR (cm⁻¹) |
|---|---|---|
| 36 | 4-OMe-phenyl | |
| 37 | 2-CF₃-phenyl | |
| 38 | 3-CF₃-phenyl | |
| 39 | 4-CF₃-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |
| 50 | 2-thienyl | |
| 51 | 2-furyl | |
| 52 | 2-imidazolyl | |

TABLE 17

Structure: 2-(CH=CH-R)-phenyl group with C(=S)(SCH3)=N-OCH3 substituent

| No. | R | mp(°C.)/IR(cm⁻¹) |
|---|---|---|
| 1. | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-NO₂-phenyl | |
| 29 | 3-NO₃-phenyl | |
| 30 | 4-NO₂-phenyl | |
| 31 | 2-CH₃-phenyl | |
| 32 | 3-CH₃-phenyl | |
| 33 | 4-CH₃-phenyl | |
| 34 | 2-OMe-phenyl | |
| 35 | 3-OMe-phenyl | |

TABLE 17-continued

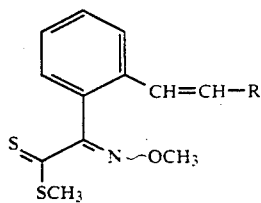

| No. | R | mp(°C.)/IR(cm⁻¹) |
|---|---|---|
| 36 | 4-OMe-phenyl | |
| 37 | 2-CF₃-phenyl | |
| 38 | 3-CF₃-phenyl | |
| 39 | 4-CF₃-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |
| 50 | 2-thienyl | |
| 51 | 2-furyl | |
| 52 | 2-imidazolyl | |

TABLE 18

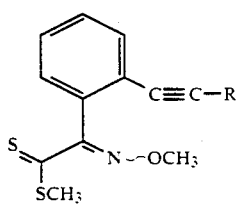

| No. | R | mp (°C.)/IR (cm⁻¹) |
|---|---|---|
| 1 | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-NO₂-phenyl | |
| 29 | 3-NO₂-phenyl | |
| 30 | 4-NO₂-phenyl | |
| 31 | 2-CH₃-phenyl | |
| 32 | 3-CH₃-phenyl | |
| 33 | 4-CH₃-phenyl | |
| 34 | 2-OMe-phenyl | |
| 35 | 3-OMe-phenyl | |
| 36 | 4-OMe-phenyl | |

TABLE 18-continued

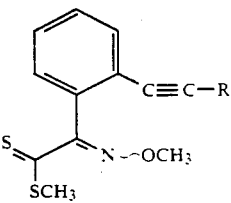

| No. | R | mp (°C.)/IR (cm⁻¹) |
|---|---|---|
| 37 | 2-CF₃-phenyl | |
| 38 | 3-CF₃-phenyl | |
| 39 | 4-CF₃-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |
| 50 | 2-thienyl | |
| 51 | 2-furyl | |
| 52 | 2-imidazolyl | |

TABLE 19

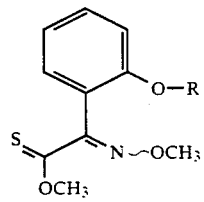

| No. | R | mp (°C.) IR (cm⁻¹) |
|---|---|---|
| 1 | methyl | |
| 2 | ethyl | |
| 3 | n-propyl | |
| 4 | iso-propyl | |
| 5 | n-butyl | |
| 6 | s-butyl | |
| 7 | iso-butyl | |
| 8 | tert.-butyl | |
| 9 | pentyl | |
| 10 | hexyl | |
| 11 | phenyl | |
| 12 | 2-F-phenyl | |
| 13 | 3-F-phenyl | |
| 14 | 4-F-phenyl | |
| 15 | 2-Cl-phenyl | |
| 16 | 3-Cl-phenyl | |
| 17 | 4-Cl-phenyl | |
| 18 | 2-Br-phenyl | |
| 19 | 3-Br-phenyl | |
| 20 | 4-Br-phenyl | |
| 21 | 2-I-phenyl | |
| 22 | 3-I-phenyl | |
| 23 | 4-I-phenyl | |
| 24 | 2-CN-phenyl | |
| 25 | 3-CN-phenyl | |
| 26 | 4-CN-phenyl | |
| 27 | 2,3-F₂-phenyl | |
| 28 | 2,4-F₂-phenyl | |
| 29 | 2,3-Cl₂-phenyl | |
| 30 | 2,4-Cl₂-phenyl | |
| 31 | 2,5-Cl₂-phenyl | |
| 32 | 2,6-Cl₂-phenyl | |
| 33 | 3,4-Cl₂-phenyl | |
| 34 | 3,5-Cl₂-phenyl | |
| 35 | 2,4-Br₂-phenyl | |
| 36 | 2,5-Br₂-phenyl | |

TABLE 19-continued

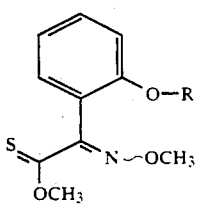

| No. | R | mp (°C.) IR (cm$^{-1}$) |
|---|---|---|
| 37 | 2,6-Br$_2$-phenyl | |
| 38 | 2,4-I$_2$-phenyl | |
| 39 | 2-Cl, 3-F-phenyl | |
| 40 | 2-Cl, 4-F-phenyl | |
| 41 | 2-Cl, 5-F-phenyl | |
| 42 | 2-Cl, 6-F-phenyl | |
| 43 | 2-Cl, 3-Br-phenyl | |
| 44 | 2-Cl, 4-Br-phenyl | |
| 45 | 2-Cl, 5-Br-phenyl | |
| 46 | 2-Cl, 6-Br-phenyl | |
| 47 | 2-Br, 3-Cl-phenyl | |
| 48 | 2-Br, 4-Cl-phenyl | |
| 49 | 2-Br, 3-F-phenyl | |
| 50 | 2-Br, 4-F-phenyl | |
| 51 | 2-Br, 5-F-phenyl | |
| 52 | 2-Br, 6-F-phenyl | |
| 53 | 2-F, 3-Cl-phenyl | |
| 54 | 2-F, 4-Cl-phenyl | |
| 55 | 2-F, 5-Cl-phenyl | |
| 56 | 3-Cl, 4-F-phenyl | |
| 57 | 3-Cl, 5-F-phenyl | |
| 58 | 3-Cl, 4-Br-phenyl | |
| 59 | 3-Cl, 5-Br-phenyl | |
| 60 | 3-F, 4-Cl-phenyl | |
| 61 | 3-F, 4-Br-phenyl | |
| 62 | 3-Br, 4-Cl-phenyl | |
| 63 | 3-Br, 4-F-phenyl | |
| 64 | 2,4,6-F$_3$-phenyl | |
| 65 | 2,3,4-Cl$_3$-phenyl | |
| 66 | 2,3,5-Cl$_3$-phenyl | |
| 67 | 2,3,6-Cl$_3$-phenyl | |
| 68 | 2,4,5-Cl$_3$-phenyl | |
| 69 | 2,4,6-Cl$_3$-phenyl | |
| 70 | 3,4,5-Cl$_3$-phenyl | |
| 71 | 2,4,6-BrS-phenyl | |
| 72 | 2,6-Cl$_2$-4-Br-phenyl | |
| 73 | 2,3,4,6-Cl$_4$-phenyl | |
| 74 | 2,3,5,6-Cl$_4$-phenyl | |
| 75 | F$_5$-phenyl | |
| 76 | Cl$_5$-phenyl | |
| 77 | Br$_5$-phenyl | |
| 78 | 2-CH$_3$-phenyl | |
| 79 | 3-CH$_3$-phenyl | |
| 80 | 4-CH$_3$-phenyl | |
| 81 | 2-C$_2$H$_5$-phenyl | |
| 82 | 3-C$_2$H$_5$-phenyl | |
| 83 | 4-C$_2$H$_5$-phenyl | |
| 84 | 2-n-C$_3$H$_7$-phenyl | |
| 85 | 3-n-C$_3$H$_7$-phenyl | |
| 86 | 4-n-C$_3$H$_7$-phenyl | |
| 87 | 2-i-C$_3$H$_7$-phenyl | |
| 88 | 3-i-C$_3$H$_7$-phenyl | |
| 89 | 4-i-C$_3$H$_7$-phenyl | |
| 90 | 2-s-C$_4$H$_9$-phenyl | |
| 91 | 3-s-C$_4$H$_9$-phenyl | |
| 92 | 4-s-C$_4$H$_9$-phenyl | |
| 93 | 2-t-C$_4$H$_9$-phenyl | |
| 94 | 3-t-C$_4$H$_9$-phenyl | |
| 95 | 4-t-C$_4$H$_9$-phenyl | |
| 96 | 2,3-(CH$_3$)$_2$-phenyl | |
| 97 | 2,4-(CH$_3$)$_2$-phenyl | |
| 98 | 2,5-(CH$_3$)$_2$-phenyl | |
| 99 | 2,6-(CH$_3$)$_2$-phenyl | |
| 100 | 3,4-(CH$_3$)$_2$-phenyl | |
| 101 | 3,5-(CH$_3$)$_2$-phenyl | |
| 102 | 2,3,4-(CH$_3$)$_3$-phenyl | |
| 103 | 2,3,5-(CH$_3$)$_3$-phenyl | |
| 104 | 2,3,6-(CH$_3$)$_3$-phenyl | |
| 105 | 2,4,5-(CH$_3$)$_3$-phenyl | |

TABLE 19-continued

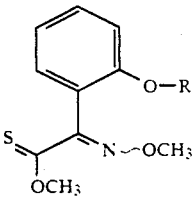

| No. | R | mp (°C.) IR (cm$^{-1}$) |
|---|---|---|
| 106 | 2,4,6-(CH$_3$)$_3$-phenyl | |
| 107 | 3,4,5-(CH$_3$)$_3$-phenyl | |
| 108 | 2,3,4,6-(CH$_3$)$_4$-phenyl | |
| 109 | 2,3,5,6-(CH$_3$)$_4$-phenyl | |
| 110 | (CH$_3$)$_5$-phenyl | |
| 111 | 2,4-(C$_2$H$_5$)$_2$-phenyl | |
| 112 | 2,6-(C$_2$H$_5$)$_2$-phenyl | |
| 113 | 3,5-(C$_2$H$_5$)$_2$-phenyl | |
| 114 | 2,4,6-(C$_2$H$_5$)$_3$-phenyl | |
| 115 | 2,4-(i-C$_3$H$_7$)$_2$-phenyl | |
| 116 | 2,6-(i-C$_3$H$_7$)$_2$-phenyl | |
| 117 | 3,5-(i-C$_3$H$_7$)$_2$-phenyl | |
| 118 | 2,4,6-(i-C$_3$H$_7$)$_3$-phenyl | |
| 119 | 2,3-(t-C$_4$H$_9$)$_2$-phenyl | |
| 120 | 2,4-(t-C$_4$H$_9$)$_2$-phenyl | |
| 121 | 2,5-(t-C$_4$H$_9$)$_2$-phenyl | |
| 122 | 2,6-(t-C$_4$H$_9$)$_2$-phenyl | |
| 123 | 3,5-(t-C$_4$H$_9$)$_2$-phenyl | |
| 124 | 2,4,6-(t-C$_4$H$_9$)$_3$-phenyl | |
| 125 | 2-t-C$_4$H$_9$, 4-CH$_3$-phenyl | |
| 126 | 2-t-C$_4$H$_9$, 5-CH$_3$-phenyl | |
| 127 | 2,6-(t-C$_4$H$_9$)$_2$, 4-CH$_3$-phenyl | |
| 128 | 2-CH$_3$, 4-t-C$_4$H$_9$-phenyl | |
| 129 | 2-CH$_3$, 6-t-C$_4$H$_9$-phenyl | |
| 130 | 2-CH$_3$, 4-i-C$_3$H$_7$-phenyl | |
| 131 | 2-CH$_3$, 5-i-C$_3$H$_7$-phenyl | |
| 132 | 3-CH$_3$, 4-i-C$_3$H$_7$-phenyl | |
| 133 | 2-i-C$_3$H$_7$, 5-CH$_3$-phenyl | |
| 134 | 2,4-(t-C$_4$H$_9$)$_2$-6-i-C$_3$H$_7$-phenyl | |
| 135 | 2-cyclo-C$_6$H$_{11}$-phenyl | |
| 136 | 3-cyclo-C$_6$H$_{11}$-phenyl | |
| 137 | 4-cyclo-C$_6$H$_{11}$-phenyl | |
| 138 | 2,4-(cyclo-C$_6$H$_{11}$)$_2$-6-CH$_3$-phenyl | |
| 139 | 2-CH$_3$, 4-cyclo-C$_6$H$_{11}$-phenyl | |
| 140 | 2-CH$_2$C$_6$H$_5$-phenyl | |
| 141 | 3-CH$_2$C$_6$H$_5$-phenyl | |
| 142 | 4-CH$_2$C$_6$H$_5$-phenyl | |
| 143 | 2-CH$_2$C$_6$H$_5$, 4-CH$_3$-phenyl | |
| 144 | 2-CH$_3$, 4-CH$_2$C$_6$H$_5$-phenyl | |
| 145 | 2-C$_6$H$_5$-phenyl | |
| 146 | 3-C$_6$H$_5$-phenyl | |
| 147 | 4-C$_6$H$_5$-phenyl | |
| 148 | 4-(2-i-C$_3$H$_7$—C$_6$H$_4$)-phenyl | |
| 149 | 4-C$_6$H$_5$, 2,6-(CH$_3$)$_2$-phenyl | |
| 150 | 2-Cl, 4-C$_6$H$_5$-phenyl | |
| 151 | 2-Br, 4-C$_6$H$_5$-phenyl | |
| 152 | 2-C$_6$H$_5$, 4-Cl-phenyl | |
| 153 | 2-C$_6$H$_5$, 4-Br-phenyl | |
| 154 | 2-CH$_2$C$_6$H$_5$, 4-Cl-phenyl | |
| 155 | 2-CH$_2$C$_6$H$_5$, 4-Br-phenyl | |
| 156 | 2-Cl, 4-CH$_2$C$_6$H$_5$-phenyl | |
| 157 | 2-Br, 4-CH$_2$C$_6$H$_5$-phenyl | |
| 158 | 2-cyclo-C$_6$H$_{11}$, 4-Cl-phenyl | |
| 159 | 2-cyclo-C$_6$H$_{11}$, 4-Br-phenyl | |
| 160 | 2-Cl, 4-cyclo-C$_6$H$_{11}$-phenyl | |
| 161 | 2-Br, 4-cyclo-C$_6$H$_{11}$-phenyl | |
| 162 | 2-OCH$_3$-phenyl | |
| 163 | 3-OCH$_3$-phenyl | |
| 164 | 4-OCH$_3$-phenyl | |
| 165 | 2,4-(OCH$_3$)$_2$-phenyl | |
| 166 | 2-CF$_3$-phenyl | |
| 167 | 3-CF$_3$-phenyl | |
| 168 | 4-CF$_3$-phenyl | |
| 169 | 2-NO$_2$-phenyl | |
| 170 | 3-NO$_2$-phenyl | |
| 171 | 4-NO$_2$-phenyl | |
| 172 | 2-CN-phenyl | |
| 173 | 3-CN-phenyl | |
| 174 | 4-CN-phenyl | |

TABLE 19-continued

[Structure: 2-(O-R)-phenyl group with C(=S)(OCH3) and =N-OCH3]

| No. | R | mp (°C.) IR (cm⁻¹) |
|---|---|---|
| 175 | 2-CH₃, 3-Cl-phenyl | |
| 176 | 2-CH₃, 4-Cl-phenyl | |
| 177 | 2-CH₃, 5-Cl-phenyl | |
| 178 | 2-CH₃, 6-Cl-phenyl | |
| 179 | 2-CH₃, 3-F-phenyl | |
| 180 | 2-CH₃, 4-F-phenyl | |
| 181 | 2-CH₃, 5-F-phenyl | |
| 182 | 2-CH₃, 6-F-phenyl | |
| 183 | 2-CH₃, 3-Br-phenyl | |
| 184 | 2-CH₃, 4-Br-phenyl | |
| 185 | 2-CH₃, 5-Br-phenyl | |
| 186 | 2-CH₃, 6-Br-phenyl | |
| 187 | 2-Cl, 3-CH₃-phenyl | |
| 188 | 2-Cl, 4-CH₃-phenyl | |
| 189 | 2-Cl, 5-CH₃-phenyl | |
| 190 | 2-Cl, 3-i-C₃H₇ | |
| 191 | 2-F, 3-CH₃-phenyl | |
| 192 | 2-F, 4-CH₃-phenyl | |
| 193 | 2-F, 5-CH₃-phenyl | |
| 194 | 2-Br, 3-CH₃-phenyl | |
| 195 | 2-Br, 4-CH₃-phenyl | |
| 196 | 3-CH₃, 4-Cl-phenyl | |
| 197 | 3-CH₃, 5-Cl-phenyl | |
| 198 | 2-Br, 5-CH₃-phenyl | |
| 199 | 3-CH₃, 4-F-phenyl | |
| 200 | 3-CH₃, 5-F-phenyl | |
| 201 | 3-CH₃, 4-Br-phenyl | |
| 202 | 3-CH₃, 5-Br-phenyl | |
| 203 | 3-F, 4-CH₃-phenyl | |
| 204 | 3-Cl, 4-CH₃-phenyl | |
| 205 | 3-Br, 4-CH₃-phenyl | |
| 206 | 2-Cl, 4,5-(CH₃)₂-phenyl | |
| 207 | 2-Br, 4,5-(CH₃)₂-phenyl | |
| 208 | 2-Cl, 3,5-(CH₃)₂-phenyl | |
| 209 | 2-Br, 3,5-(CH₃)₂-phenyl | |
| 210 | 2,6-Cl₂, 4-CH₃-phenyl | |
| 211 | 2,6-F₂, 4-CH₃-phenyl | |
| 212 | 2,6-Br₂, 4-CH₃-phenyl | |
| 213 | 2,4-Cl₂, 6-CH₃-phenyl | |
| 214 | 2,4-F₂, 6-CH₃-phenyl | |
| 215 | 2,4-Br₂, 6-CH₃-phenyl | |
| 216 | 2,6-(CH₃)₂, 4-F-phenyl | |
| 217 | 2,6-(CH₃)₂, 4-Cl-phenyl | |
| 218 | 2,6-(CH₃)₂, 4-Br-phenyl | |
| 219 | 3,5-(CH₃)₂, 4-F-phenyl | |
| 220 | 3,5-(CH₃)₂, 4-Cl-phenyl | |
| 221 | 3,5-(CH₃)₂, 4-Br-phenyl | |
| 222 | 2,3,6-(CH₃)₃, 4-F-phenyl | |
| 223 | 2,3,6-(CH₃)₃, 4-Cl-phenyl | |
| 224 | 2,3,6-(CH₃)₃, 4-Br-phenyl | |
| 225 | 2,4-(CH₃)₂, 6-F-phenyl | |
| 226 | 2,4-(CH₃)₂, 6-Cl-phenyl | |
| 227 | 2,4-(CH₃)₂, 6-Br-phenyl | |
| 228 | 2-i-C₃H₇, 4-Cl, 5-CH₃-phenyl | |
| 229 | 2-Cl, 4-NO₂-phenyl | |
| 230 | 2-NO₂, 4-Cl-phenyl | |
| 231 | 2-OCH₃, 5-NO₂-phenyl | |
| 232 | 2,4-Cl₂, 5-NO₂-phenyl | |
| 233 | 2,4-Cl₂, 6-NO₂-phenyl | |
| 234 | 2,6-Cl₂, 4-NO₂-phenyl | |
| 235 | 2,6-Br₂, 4-NO₂-phenyl | |
| 236 | 2,6-J₂, 4-NO₂-phenyl | |
| 237 | 2-C₆H₅O-phenyl | |
| 238 | 3-C₆H₅O-phenyl | |
| 239 | 4-C₆H₅O-phenyl | |
| 240 | 3-t-C₄H₉O-phenyl | |
| 241 | 4-t-C₄H₉O-phenyl | |
| 242 | 1-naphthyl | |
| 243 | 2-naphthyl | |
| 244 | 2-pyridyl | |
| 245 | 6-methyl-2-pyridyl | |
| 246 | 6-ethyl-2-pyridyl | |
| 247 | 6-n-propyl-2-pyridyl | |
| 248 | 6-iso-propyl-2-pyridyl | |
| 249 | 6-n-butyl-2-pyridyl | |
| 250 | 6-tert.-butyl-2-pyridyl | |
| 251 | 6-n-pentyl-2-pyridyl | |
| 252 | 6-n-hexyl-2-pyridyl | |
| 253 | 6-phenyl-2-pyridyl | |
| 254 | 6-benzyl-2-pyridyl | |
| 255 | 6-trifluoromethyl-2-pyridyl | |
| 256 | 6-methoxy-2-pyridyl | |
| 257 | 6-chloro-2-pyridyl | |
| 258 | 3,6-dimethyl-2-pyridyl | |
| 259 | 3,6-diethyl-2-pyridyl | |
| 260 | 4,6-dimethyl-2-pyridyl | |
| 261 | 5,6-dimethyl-2-pyridyl | |
| 262 | 4-phenyl-6-methyl-2-pyridyl | |
| 263 | 4,6-diphenyl-2-pyridyl | |
| 264 | 3,4-dichloro-6-methyl-2-pyridyl | |
| 265 | 3,4,5-trichloro-6-phenyl-2-pyridyl | |
| 266 | 4-trifluoromethyl-6-methyl-2-pyridyl | |
| 267 | 3-cyano-6-methyl-2-pyridyl | |
| 268 | 3-cyano-6-ethyl-2-pyridyl | |
| 269 | 3-cyano-6-n-propyl-2-pyridyl | |
| 270 | 3-cyano-6-iso-propyl-2-pyridyl | |
| 271 | 3-cyano-6-cyclo-propyl-2-pyridyl | |
| 272 | 3-cyano-6-n-butyl-2-pyridyl | |
| 273 | 3-cyano-6-tert.-butyl-2-pyridyl | |
| 274 | 3-cyano-6-cyclo-hexyl-2-pyridyl | |
| 275 | 3-cyano-6-phenyl-2-pyridyl | |
| 276 | 3-cyano-4,6-dimethyl-2-pyridyl | |
| 277 | 3,5,6-trichloro-2-pyridyl | |
| 278 | 5-trifluoromethyl-2-pyridyl | |
| 279 | 3-chloro-5-trifluoromethyl-2-pyridyl | |
| 280 | 2-quinolyl | |
| 281 | 3-methyl-2-quinolyl | |
| 282 | 4-methyl-2-quinolyl | |
| 283 | 4-ethyl-2-quinolyl | |
| 284 | 4-phenyl-2-quinolyl | |
| 285 | 6-methyl-2-quinolyl | |
| 286 | 6-chloro-2-quinolyl | |
| 287 | 8-methyl-2-quinolyl | |
| 288 | 8-chloro-2-quinolyl | |
| 289 | 3,4-dimethyl-2-quinolyl | |
| 290 | 4-methyl-8-methoxy-2-quinolyl | |
| 291 | 4-phenyl-8-ethoxy-2-quinolyl | |
| 292 | 4-methyl-8-chloro-2-quinolyl | |
| 293 | 4-methyl-8-fluoro-2-quinolyl | |
| 294 | 4-quinolyl | |
| 295 | 2-methyl-4-quinolyl | |
| 296 | 2-trifluoromethyl-4-quinolyl | |
| 297 | 2-iso-propyl-4-quinolyl | |
| 298 | 2-n-pentyl-4-quinolyl | |
| 299 | 2-phenyl-4-quinolyl | |
| 300 | 2,6-dimethyl-4-quinolyl | |
| 301 | 2-methyl-6-chloro-4-quinolyl | |
| 302 | 2-methyl-6-fluoro-4-quinolyl | |
| 303 | 8-quinolyl | |
| 304 | 2-methyl-8-quinolyl | |
| 305 | 5,7-dichloro-8-quinolyl | |
| 306 | 4,6-dimethyl-2-pyrimidinyl | |
| 307 | 4-trifluoromethyl-2-pyrimidinyl | |
| 308 | 4,5,6-trimethyl-2-pyrimidinyl | |
| 309 | 4-benzyl-6-methyl-2-pyrimidinyl | |
| 310 | 4-methyl-6-phenyl-2-pyrimidinyl | |
| 311 | 4,6-dimethyl-5-chloro-2-pyrimidinyl | |
| 312 | 2,6-dimethyl-4-pyrimidinyl | |

TABLE 19-continued

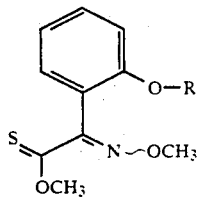

| No. | R | mp (°C.)/ IR (cm$^{-1}$) |
|---|---|---|
| 313 | 2,6-bis-(trifluoromethyl)-4-pyrimidinyl | |
| 314 | 2-iso-propyl-6-methyl-4-pyrimidinyl | |
| 315 | 2-cyclo-propyl-6-methyl-4-pyrimdinyl | |
| 316 | 2-methyl-6-methoxymethyl-4-pyrimidinyl | |
| 317 | 2-iso-propyl-6-methoxymethyl-4-pyrimidinyl | |
| 318 | 2-phenyl-4-pyrimidinyl | |
| 319 | 3,5-dimethyl-4-pyrimidinyl | |
| 320 | 2-methyl-6-trifluoromethyl-4-pyrimidinyl | |
| 321 | 2-n-propyl-6-trifluoromethyl-4-pyrimidinyl | |
| 322 | 2-iso-propyl-6-trifluoromethyl-4-pyrimdinyl | |
| 323 | 2-methyl-5-chloro-6-trifluoromethyl-4-pyrimidinyl | |
| 324 | 2-n-propyl-5-chloro-6-trifluoromethyl-4-pyrimidinyl | |
| 325 | 2-iso-propyl-5-chloro-6-trifluoromethyl-4-pyrimidinyl | |
| 326 | 2-tert.-butyl-5-chloro-6-trifluoromethyl-4-pyrimidinyl | |

TABLE 20

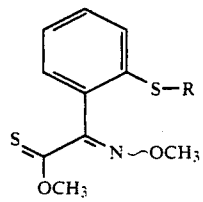

| No. | R | mp (°C.)/ IR(cm$^{-1}$) |
|---|---|---|
| 1 | methyl | |
| 2 | ethyl | |
| 3 | n-propyl | |
| 4 | iso-propyl | |
| 5 | n-butyl | |
| 6 | s-butyl | |
| 7 | iso-butyl | |
| 8 | tert.-butyl | |
| 9 | pentyl | |
| 10 | hexyl | |
| 11 | phenyl | |
| 12 | 2-F-phenyl | |
| 13 | 3-F-phenyl | |
| 14 | 4-F-phenyl | |
| 15 | 2-Cl-phenyl | |
| 16 | 3-Cl-phenyl | |
| 17 | 4-Cl-phenyl | |
| 18 | 2-Br-phenyl | |
| 19 | 3-Br-phenyl | |
| 20 | 4-Br-phenyl | |
| 21 | 2-I-phenyl | |
| 22 | 3-I-phenyl | |
| 23 | 4-I-phenyl | |
| 24 | 2-CN-phenyl | |
| 25 | 3-CN-phenyl | |
| 26 | 4-CN-phenyl | |
| 27 | 2,3-F$_2$-phenyl | |
| 28 | 2,4-F$_2$-phenyl | |
| 29 | 2,3-Cl$_2$-phenyl | |
| 30 | 2,4-Cl$_2$-phenyl | |
| 31 | 2,5-Cl$_2$-phenyl | |
| 32 | 2,6-Cl$_2$-phenyl | |
| 33 | 3,4-Cl$_2$-phenyl | |

TABLE 20-continued

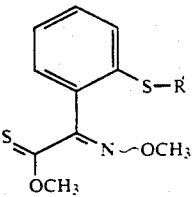

| No. | R | mp (°C.)/ IR(cm$^{-1}$) |
|---|---|---|
| 34 | 3,5-Cl$_2$-phenyl | |
| 35 | 2,4-Br$_2$-phenyl | |
| 36 | 2,5-Br$_2$-phenyl | |
| 37 | 2,6-Br$_2$-phenyl | |
| 38 | 2,4-I$_2$-phenyl | |
| 39 | 2-Cl, 3-F-phenyl | |
| 40 | 2-Cl, 4-F-phenyl | |
| 41 | 2-Cl, 5-F-phenyl | |
| 42 | 2-Cl, 6-F-phenyl | |
| 43 | 2-Cl, 3-Br-phenyl | |
| 44 | 2-Cl, 4-Br-phenyl | |
| 45 | 2-Cl, 5-Br-phenyl | |
| 46 | 2-Cl, 6-Br-phenyl | |
| 47 | 2-Br, 3-Cl-phenyl | |
| 48 | 2-Br, 4-Cl-phenyl | |
| 49 | 2-Br, 3-F-phenyl | |
| 50 | 2-Br, 4-F-phenyl | |
| 51 | 2-Br, 5-F-phenyl | |
| 52 | 2-Br, 6-F-phenyl | |
| 53 | 2-F, 3-Cl-phenyl | |
| 54 | 2-F, 4-Cl-phenyl | |
| 55 | 2-F, 5-Cl-phenyl | |
| 56 | 3-Cl, 4-F-phenyl | |
| 57 | 3-Cl, 5-F-phenyl | |
| 58 | 3-Cl, 4-Br-phenyl | |
| 59 | 3-Cl, 5-Br-phenyl | |
| 60 | 3-F, 4-Cl-phenyl | |
| 61 | 3-F, 4-Br-phenyl | |
| 62 | 3-Br, 4-Cl-phenyl | |
| 63 | 3-Br, 4-F-phenyl | |
| 64 | 2,4,6-F$_3$-phenyl | |
| 65 | 2,3,4,-Cl$_3$-phenyl | |
| 66 | 2,3,5-Cl$_3$-phenyl | |
| 67 | 2,3,6-Cl$_3$-phenyl | |
| 68 | 2,4,5-Cl$_3$-phenyl | |
| 69 | 2,4,6-Cl$_3$-phenyl | |
| 70 | 3,4,5-Cl$_3$-phenyl | |
| 71 | 2,4,6-Br$_3$-phenyl | |
| 72 | 2,6-Cl$_2$-4-Br-phenyl | |
| 73 | 2,3,4,6-Cl$_4$-phenyl | |
| 74 | 2,3,5,6-Cl$_4$-phenyl | |
| 75 | F$_5$-phenyl | |
| 76 | Cl$_5$-phenyl | |
| 77 | Br$_5$-phenyl | |
| 78 | 2-CH$_3$-phenyl | |
| 79 | 3-CH$_3$-phenyl | |
| 80 | 4-CH$_3$-phenyl | |
| 81 | 2-C$_2$H$_5$-phenyl | |
| 82 | 3-C$_2$H$_5$-phenyl | |
| 83 | 4-C$_2$H$_5$-phenyl | |
| 84 | 2-n-C$_3$H$_7$-phenyl | |
| 85 | 3-n-C$_3$H$_7$-phenyl | |
| 86 | 4-n-C$_3$H$_7$-phenyl | |
| 87 | 2-i-C$_3$H$_7$-phenyl | |
| 88 | 3-i-C$_3$H$_7$-phenyl | |
| 89 | 4-i-C$_3$H$_7$-phenyl | |
| 90 | 2-s-C$_4$H$_9$-phenyl | |
| 91 | 3-s-C$_4$H$_9$-phenyl | |
| 92 | 4-s-C$_4$H$_9$-phenyl | |
| 93 | 2-t-C$_4$H$_9$-phenyl | |
| 94 | 3-t-C$_4$H$_9$-phenyl | |
| 95 | 4-t-C$_4$H$_9$-phenyl | |
| 96 | 2,3-(CH$_3$)$_2$-phenyl | |
| 97 | 2,4-(CH$_3$)$_2$-phenyl | |
| 98 | 2,5-(CH$_3$)$_2$-phenyl | |
| 99 | 2,6-(CH$_3$)$_2$-phenyl | |
| 100 | 3,4-(CH$_3$)$_2$-phenyl | |
| 101 | 3,5-(CH$_3$)$_2$-phenyl | |
| 102 | 2,3,4-(CH$_3$)$_3$-phenyl | |

TABLE 20-continued

Structure: 2-(S-R)-phenyl group with C(=S)OCH₃ and =N-OCH₃ substituents

| No. | R | mp (°C.)/IR(cm⁻¹) |
|---|---|---|
| 103 | 2,3,5-(CH$_3$)$_3$-phenyl | |
| 104 | 2,3,6-(CH$_3$)$_3$-phenyl | |
| 105 | 2,4,5-(CH$_3$)$_3$-phenyl | |
| 106 | 2,4,6-(CH$_3$)$_3$-phenyl | |
| 107 | 3,4,5-(CH$_3$)$_3$-phenyl | |
| 108 | 2,3,4,6-(CH$_3$)$_4$-phenyl | |
| 109 | 2,3,5,6-(CH$_3$)$_4$-phenyl | |
| 110 | (CH$_3$)$_5$-phenyl | |
| 111 | 2,4-(C$_2$H$_5$)$_2$-phenyl | |
| 112 | 2,6-(C$_2$H$_5$)$_2$-phenyl | |
| 113 | 3,5-(C$_2$H$_5$)$_2$-phenyl | |
| 114 | 2,4,6-(C$_2$H$_5$)$_3$-phenyl | |
| 115 | 2,4-(i-C$_3$H$_7$)$_2$-phenyl | |
| 116 | 2,6-(i-C$_3$H$_7$)$_2$-phenyl | |
| 117 | 3,5-(i-C$_3$H$_7$)$_2$-phenyl | |
| 118 | 2,4,6-(i-C$_3$H$_7$)$_3$-phenyl | |
| 119 | 2,3-(t-C$_4$H$_9$)$_2$-phenyl | |
| 120 | 2,4-(t-C$_4$H$_9$)$_2$-phenyl | |
| 121 | 2,5-(t-C$_4$H$_9$)$_2$-phenyl | |
| 122 | 2,6-(t-C$_4$H$_9$)$_2$-phenyl | |
| 123 | 3,5-(t-C$_4$H$_9$)$_2$-phenyl | |
| 124 | 2,4,6-(t-C$_4$H$_9$)$_3$-phenyl | |
| 125 | 2-t-C$_4$H$_9$, 4-CH$_3$-phenyl | |
| 126 | 2-t-C$_4$H$_9$, 5-CH$_3$-phenyl | |
| 127 | 2,6-(t-C$_4$H$_9$)$_2$, 4-CH$_3$-phenyl | |
| 128 | 2-CH$_3$, 4-t-C$_4$H$_9$-phenyl | |
| 129 | 2-CH$_3$, 6-t-C$_4$H$_9$-phenyl | |
| 130 | 2-CH$_3$, 4-i-C$_3$H$_7$-phenyl | |
| 131 | 2-CH$_3$, 5-i-C$_3$H$_7$-phenyl | |
| 132 | 3-CH$_3$, 4-i-C$_3$H$_7$-phenyl | |
| 133 | 2-i-C$_3$H$_7$, 5-CH$_3$-phenyl | |
| 134 | 2,4-(t-C$_4$H$_9$)$_2$-6-i-C$_3$H$_7$-phenyl | |
| 135 | 2-cyclo-C$_6$H$_{11}$-phenyl | |
| 136 | 3-cyclo-C$_6$H$_{11}$-phenyl | |
| 137 | 4-cyclo-C$_6$H$_{11}$-phenyl | |
| 138 | 2,4-(cyclo-C$_6$H$_{11}$)$_2$-6-CH$_3$-phenyl | |
| 139 | 2-CH$_3$, 4-cyclo-C$_6$H$_{11}$-phenyl | |
| 140 | 2-CH$_2$C$_6$H$_5$-phenyl | |
| 141 | 3-CH$_2$C$_6$H$_5$-phenyl | |
| 142 | 4-CH$_2$C$_6$H$_5$-phenyl | |
| 143 | 2-CH$_2$C$_6$H$_5$, 4-CH$_3$-phenyl | |
| 144 | 2-CH$_3$, 4-CH$_2$C$_6$H$_5$-phenyl | |
| 145 | 2-C$_6$H$_5$-phenyl | |
| 146 | 3-C$_6$H$_5$-phenyl | |
| 147 | 4-C$_6$H$_5$-phenyl | |
| 148 | 4-(2-i-C$_3$H$_7$—C$_6$H$_4$)-phenyl | |
| 149 | 4-C$_6$H$_5$, 2,6-(CH$_3$)$_2$-phenyl | |
| 150 | 2-Cl, 4-C$_6$H$_5$-phenyl | |
| 151 | 2-Br, 4-C$_6$H$_5$-phenyl | |
| 152 | 2-C$_6$H$_5$, 4-Cl-phenyl | |
| 153 | 2-C$_6$H$_5$, 4-Br-phenyl | |
| 154 | 2-CH$_2$C$_6$H$_5$, 4-Cl-phenyl | |
| 155 | 2-CH$_2$C$_6$H$_5$, 4-Br-phenyl | |
| 156 | 2-Cl, 4-CH$_2$C$_6$H$_5$-phenyl | |
| 157 | 2-Br, 4-CH$_2$C$_6$H$_5$-phenyl | |
| 158 | 2-cyclo-C$_6$H$_{11}$, 4-Cl-phenyl | |
| 159 | 2-cyclo-C$_6$H$_{11}$, 4-Br-phenyl | |
| 160 | 2-Cl, 4-cyclo-C$_6$H$_{11}$-phenyl | |
| 161 | 2-Br, 4-cyclo-C$_6$H$_{11}$-phenyl | |
| 162 | 3-OCH$_3$-phenyl | |
| 163 | 2,4-(OCH$_3$)$_2$-phenyl | |
| 164 | 2-CF$_3$-phenyl | |
| 165 | 3-CF$_3$-phenyl | |
| 166 | 4-CF$_3$-phenyl | |
| 167 | 2-NO$_2$-phenyl | |
| 168 | 3-NO$_2$-phenyl | |
| 169 | 4-NO$_2$-phenyl | |
| 170 | 2-CN-phenyl | |
| 171 | 3-CN-phenyl | |
| 172 | 4-CN-phenyl | |
| 173 | 2-CH$_3$, 3-Cl-phenyl | |
| 174 | 2-CH$_3$, 4-Cl-phenyl | |
| 175 | 2-CH$_3$, 5-Cl-phenyl | |
| 176 | 2-CH$_3$, 6-Cl-phenyl | |
| 177 | 2-CH$_3$, 3-F-phenyl | |
| 178 | 2-CH$_3$, 4-F-phenyl | |
| 179 | 2-CH$_3$, 5-F-phenyl | |
| 180 | 2-CH$_3$, 6-F-phenyl | |
| 181 | 2-CH$_3$, 3-Br-phenyl | |
| 182 | 2-CH$_3$, 4-Br-phenyl | |
| 183 | 2-CH$_3$, 5-Br-phenyl | |
| 184 | 2-CH$_3$, 6-Br-phenyl | |
| 185 | 2-Cl, 3-CH$_3$-phenyl | |
| 186 | 2-Cl, 4-CH$_3$-phenyl | |
| 187 | 2-Cl, 5-CH$_3$-phenyl | |
| 188 | 2-Cl, 3-i-C$_3$H$_7$ | |
| 189 | 2-F, 3-CH$_3$-phenyl | |
| 190 | 2-F, 4-CH$_3$-phenyl | |
| 191 | 2-F, 5-CH$_3$-phenyl | |
| 192 | 2-Br, 3-CH$_3$-phenyl | |
| 193 | 2-Br, 4-CH$_3$-phenyl | |
| 194 | 3-CH$_3$, 4-Cl-phenyl | |
| 195 | 3-CH$_3$, 5-Cl-phenyl | |
| 196 | 2-Br, 5-CH$_3$-phenyl | |
| 197 | 3-CH$_3$, 4-F-phenyl | |
| 198 | 3-CH$_3$, 5-F-phenyl | |
| 199 | 3-CH$_3$, 4-Br-phenyl | |
| 200 | 3-CH$_3$, 5-Br-phenyl | |
| 201 | 3-F, 4-CH$_3$-phenyl | |
| 202 | 3-Cl, 4-CH$_3$-phenyl | |
| 203 | 3-Br, 4-CH$_3$-phenyl | |
| 204 | 2-Cl, 4,5-(CH$_3$)$_2$-phenyl | |
| 205 | 2-Br, 4,5-(CH$_3$)$_2$-phenyl | |
| 206 | 2-Cl, 3,5-(CH$_3$)$_2$-phenyl | |
| 207 | 2-Br, 3,5-(CH$_3$)$_2$-phenyl | |
| 208 | 2,6-Cl$_2$, 4-CH$_3$-phenyl | |
| 209 | 2,6-F$_2$, 4-CH$_3$-phenyl | |
| 210 | 2,6-Br$_2$, 4-CH$_3$-phenyl | |
| 211 | 2,4-Cl$_2$, 6-CH$_3$-phenyl | |
| 212 | 2,4-F$_2$, 6-CH$_3$-phenyl | |
| 213 | 2,4-Br$_2$, 6-CH$_3$-phenyl | |
| 214 | 2,6-(CH$_3$)$_2$, 4-F-phenyl | |
| 215 | 2,6-(CH$_3$)$_2$, 4-Cl-phenyl | |
| 216 | 2,6-(CH$_3$)$_2$, 4-Br-phenyl | |
| 217 | 3,5-(CH$_3$)$_2$, 4-F-phenyl | |
| 218 | 3,5-(CH$_3$)$_2$, 4-Cl-phenyl | |
| 219 | 3,5-(CH$_3$)$_2$, 4-Br-phenyl | |
| 220 | 2,3,6-(CH$_3$)$_3$, 4-F-phenyl | |
| 221 | 2,3,6-(CH$_3$)$_3$, 4-Cl-phenyl | |
| 222 | 2,3,6-(CH$_3$)$_3$, 4-Br-phenyl | |
| 223 | 2,4-(CH$_3$)$_2$, 6-F-phenyl | |
| 224 | 2,4-(CH$_3$)$_2$, 6-Cl-phenyl | |
| 225 | 2,4-(CH$_3$)$_2$, 6-Br-phenyl | |
| 226 | 2-i-C$_3$H$_7$, 4-Cl, 5-CH$_3$-phenyl | |
| 227 | 2-Cl, 4-NO$_2$-phenyl | |
| 228 | 2-NO$_2$, 4-Cl-phenyl | |
| 229 | 2-OCH$_3$, 5-NO$_2$-phenyl | |
| 230 | 2,4-Cl$_2$, 5-NO$_2$-phenyl | |
| 231 | 2,4-Cl$_2$, 6-NO$_2$-phenyl | |
| 232 | 2,6-Cl$_2$, 4-NO$_2$-phenyl | |
| 233 | 2,6-Br$_2$, 4-NO$_2$-phenyl | |
| 234 | 2,6-I$_2$, 4-NO$_2$-phenyl | |
| 235 | 2-C$_6$H$_5$O-phenyl | |
| 236 | 3-C$_6$H$_5$O-phenyl | |
| 237 | 4-C$_6$H$_5$O-phenyl | |
| 238 | 3-t-C$_4$H$_9$O-phenyl | |
| 239 | 4-t-C$_4$H$_9$O-phenyl | |
| 240 | 1-naphthyl | |

TABLE 20-continued

Structure: 2-(S-R)-phenyl group with C(=S)OCH₃ and N–OCH₃ substituents

| No. | R | mp (°C.)/IR(cm⁻¹) |
|---|---|---|
| 241 | 2-naphthyl | |
| 242 | 2-pyridyl | |
| 243 | 6-methyl-2-pyridyl | |
| 244 | 6-ethyl-2-pyridyl | |
| 245 | 6-n-propyl-2-pyridyl | |
| 246 | 6-iso-propyl-2-pyridyl | |
| 247 | 6-n-butyl-2-pyridyl | |
| 248 | 6-tert.-butyl-2-pyridyl | |
| 249 | 6-n-pentyl-2-pyridyl | |
| 250 | 6-n-hexyl-2-pyridyl | |
| 251 | 6-phenyl-2-pyridyl | |
| 252 | 6-benzyl-2-pyridyl | |
| 253 | 6-trifluoromethyl-2-pyridyl | |
| 254 | 6-methoxy-2-pyridyl | |
| 255 | 6-chloro-2-pyridyl | |
| 256 | 3,6-dimethyl-2-pyridyl | |
| 257 | 3,6-diethyl-2-pyridyl | |
| 258 | 4,6-dimethyl-2-pyridyl | |
| 259 | 5,6-dimethyl-2-pyridyl | |
| 260 | 4-phenyl-6-methyl-2-pyridyl | |
| 261 | 4,6-diphenyl-2-pyridyl | |
| 262 | 3,4-dichloro-6-methyl-2-pyridyl | |
| 263 | 3,4,5-trichloro-6-phenyl-2-pyridyl | |
| 264 | 4-trifluoromethyl-6-methyl-2-pyridyl | |
| 265 | 3-cyano-6-methyl-2-pyridyl | |
| 266 | 3-cyano-6-ethyl-2-pyridyl | |
| 267 | 3-cyano-6-n-propyl-2-pyridyl | |
| 268 | 3-cyano-6-iso-propyl-2-pyridyl | |
| 269 | 3-cyano-6-cyclo-propyl-2-pyridyl | |
| 270 | 3-cyano-6-n-butyl-2-pyridyl | |
| 271 | 3-cyano-6-tert.-butyl-2-pyridyl | |
| 272 | 3-cyano-6-cyclo-hexyl-2-pyridyl | |
| 273 | 3-cyano-6-phenyl-2-pyridyl | |
| 274 | 3-cyano-4,6-dimethyl-2-pyridyl | |
| 275 | 3,5,6-trichloro-2-pyridyl | |
| 276 | 5-trifluoromethyl-2-pyridyl | |
| 277 | 3-chloro-5-trifluoromethyl-2-pyridyl | |
| 278 | 2-quinolyl | |
| 279 | 3-methyl-2-quinolyl | |
| 280 | 4-methyl-2-quinolyl | |
| 281 | 4-ethyl-2-quinolyl | |
| 282 | 4-phenyl-2-quinolyl | |
| 283 | 6-methyl-2-quinolyl | |
| 284 | 6-chloro-2-quinolyl | |
| 285 | 8-methyl-2-quinolyl | |
| 286 | 8-chloro-2-quinolyl | |
| 287 | 3,4-dimethyl-2-quinolyl | |
| 288 | 4-methyl-8-methoxy-2-quinolyl | |
| 289 | 4-phenyl-8-ethoxy-2-quinolyl | |
| 290 | 4-methyl-8-chloro-2-quinolyl | |
| 291 | 4-methyl-8-fluoro-2-quinolyl | |
| 292 | 4-quinolyl | |
| 293 | 2-methyl-4-quinolyl | |
| 294 | 2-trifluoromethyl-4-quinolyl | |
| 295 | 2-iso-propyl-4-quinolyl | |
| 296 | 2-n-pentyl-4-quinolyl | |
| 297 | 2-phenyl-4-quinolyl | |
| 298 | 2,6-dimethyl-4-quinolyl | |
| 299 | 2-methyl-6-chloro-4-quinolyl | |
| 300 | 2-methyl-6-fluoro-4-quinolyl | |
| 301 | 8-quinolyl | |
| 302 | 2-methyl-8-quinolyl | |
| 303 | 5,7-dichloro-8-quinolyl | |
| 304 | 4,6-dimethyl-2-pyrimidinyl | |
| 305 | 4-trifluoromethyl-2-pyrimidinyl | |
| 306 | 4,5,6-trimethyl-2-pyrimidinyl | |
| 307 | 4-benzyl-6-methyl-2-pyrimidinyl | |
| 308 | 4-methyl-6-phenyl-2-pyrimidinyl | |
| 309 | 4,6-dimethyl-5-chloro-2-pyrimidinyl | |
| 310 | 2,6-dimethyl-4-pyrimidinyl | |
| 311 | 2,6-bis-(trifluoromethyl)-4-pyrimidinyl | |
| 312 | 2-iso-propyl-6-methyl-4-pyrimidinyl | |
| 313 | 2-cyclo-propyl-6-methyl-4-pyrimidinyl | |
| 314 | 2-methyl-6-methoxymethyl-4-pyrimidinyl | |
| 315 | 2-iso-propyl-6-methoxymethyl-4-pyrimidinyl | |
| 316 | 2-phenyl-4-pyrimidinyl | |
| 317 | 3,5-dimethyl-4-pyrimidinyl | |
| 318 | 2-methyl-6-trifluoromethyl-4-pyrimidinyl | |
| 319 | 2-n-propyl-6-trifluoromethyl-4-pyrimidinyl | |
| 320 | 2-iso-propyl-6-trifluoromethyl-4-pyrimidinyl | |
| 321 | 2-methyl-5-chloro-6-trifluoromethyl-4-pyrimidinyl | |
| 322 | 2-n-propyl-5-chloro-6-trifluoromethyl-4-pyrimidinyl | |
| 323 | 2-iso-propyl-5-chloro-6-trifluoromethyl-4-pyrimidinyl | |
| 324 | 2-tert.-butyl-5-chloro-6-trifluoromethyl-4-pyrimidinyl | |
| 325 | 6-EtO-benzothiazol-2-yl | |
| 326 | benzoxazol-2-yl | |
| 327 | 1-Me-imidazol-2-yl | |
| 328 | 4-but-1H-imidazol-2-yl | |
| 329 | 2-thiazolin-2-yl | |
| 330 | 5-CF₃-benzimidazol-2-yl | |
| 331 | 1-Ph-tetrazol-5-yl | |
| 332 | 5-CF₃-benzothiazol-2-yl | |
| 333 | 4,4-Me₂-5-methylene-2-thiazolin-2-yl | |
| 334 | 6-Cl-4-Me-benzothiazol-2-yl | |
| 335 | 5-Me-benzothiazol-2-yl | |
| 336 | 4-Cl-benzothiazol-2-yl | |
| 337 | 1-(3-NO₂—Ph)tetrazol-5-yl | |
| 338 | 2-thienyl | |
| 339 | 5-Me-benzoxazol-2-yl | |
| 340 | 7-Cl-benzothiazol-2-yl | |
| 341 | 5,6-Cl₃-1H-benzimidazol-2-yl | |
| 342 | 5-Cl-benzoxazol-2-yl | |
| 343 | 6-Cl-benzothiazol-2-yl | |
| 344 | 2-Ph-thiazol-2-yl | |
| 345 | 3-CN-4,6-Me₂-2-pyridyl | |
| 346 | 1-Ph-1,2,4-triazol-3-yl | |
| 347 | 1-Pri-benzimidazol-2-yl | |
| 348 | 5-Br-benzothiazol-2-yl | |
| 349 | 5-Br-1H-benzimidazol-2-yl | |
| 350 | 7-Cl-4-MeO-benzothiazol-2-yl | |
| 351 | 1H-benzimidazol-2-yl | |
| 352 | 5-Cl-benzothiazol-2-yl | |
| 353 | 5-NO₂-benzoxazol-2-yl | |
| 354 | 5-t-Bu-benzoxazol-2-yl | |
| 355 | 4,6,7-Cl₃-benzothiozol-2-yl | |
| 356 | 5-Ph-thiazol-2-yl | |
| 357 | 5,7-Me₂-benzoxazol-2-yl | |
| 358 | 6-Me-benzoxazol-2-yl | |
| 359 | 1,2,4-triazin-3-yl | |
| 360 | 6-Pr-benzothiazol-2-yl | |
| 361 | 6-PhO-benzothiazol-2-yl | |
| 362 | 4-(4-Cl—Ph)-thiazol-2-yl | |
| 363 | 4-(4-Me—Ph)-thiazol-2-yl | |
| 364 | 5-Me-4-Ph-thiazol-2-yl | |
| 365 | 5-Cl-1-H-benzimidazol-2-yl | |
| 366 | 5-Ph-1,2,4-triazol-3-yl | |
| 367 | 3-Ph-1,2,4-thiadiazol-5-yl | |

TABLE 21

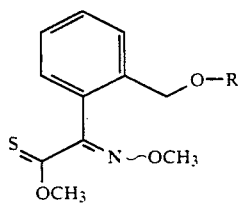

| No. | R | mp(°C.)/IR(cm$^{-1}$) |
|---|---|---|
| 1 | methyl | |
| 2 | ethyl | |
| 3 | n-propyl | |
| 4 | iso-propyl | |
| 5 | n-butyl | |
| 6 | s-butyl | |
| 7 | iso-butyl | |
| 8 | tert.-butyl | |
| 9 | pentyl | |
| 10 | hexyl | |
| 11 | phenyl | |
| 12 | 2-F-phenyl | |
| 13 | 3-F-phenyl | |
| 14 | 4-F-phenyl | |
| 15 | 2-Cl-phenyl | 58–60° C. |
| 16 | 3-Cl-phenyl | |
| 17 | 4-Cl-phenyl | |
| 18 | 2-Br-phenyl | |
| 19 | 3-Br-phenyl | |
| 20 | 4-Br-phenyl | |
| 21 | 2-I-phenyl | |
| 22 | 3-I-phenyl | |
| 23 | 4-I-phenyl | |
| 24 | 2-CH$_3$-phenyl | 1662, 1494, 1461, 1240, 1190, 1122, 1051, 1025, 845, 753 (cm$^{-1}$) |
| 25 | 2-CN-phenyl | |
| 26 | 3-CN-phenyl | |
| 27 | 4-CN-phenyl | |
| 28 | 2,3-F$_2$-phenyl | |
| 29 | 2,4-F$_2$-phenyl | |
| 30 | 2,3-Cl$_2$-phenyl | |
| 31 | 2,4-Cl$_2$-phenyl | |
| 32 | 2,5-Cl$_2$-phenyl | |
| 33 | 2,6-Cl$_2$-phenyl | |
| 34 | 3,4-Cl$_2$-phenyl | |
| 35 | 3,5-Cl$_2$-phenyl | |
| 36 | 2,4-Br$_2$-phenyl | |
| 37 | 2,5-Br$_2$-phenyl | |
| 38 | 2,6-Br$_2$-phenyl | |
| 39 | 2,4-I$_2$-phenyl | |
| 40 | 2-Cl, 3-F-phenyl | |
| 41 | 2-Cl, 4-F-phenyl | |
| 42 | 2-Cl, 5-F-phenyl | |
| 43 | 2-Cl, 6-F-phenyl | |
| 44 | 2-Cl, 3-Br-phenyl | |
| 45 | 2-Cl, 4-Br-phenyl | |
| 46 | 2-Cl, 5-Br-phenyl | |
| 47 | 2-Cl, 6-Br-phenyl | |
| 48 | 2-Br, 3-Cl-phenyl | |
| 49 | 2-Br, 4-Cl-phenyl | |
| 50 | 2-Br, 3-F-phenyl | |
| 51 | 2-Br, 4-F-phenyl | |
| 52 | 2-Br, 5-F-phenyl | |
| 53 | 2-Br, 6-F-phenyl | |
| 54 | 2-F, 3-Cl-phenyl | |
| 55 | 2-F, 4-Cl-phenyl | |
| 56 | 2-F, 5-Cl-phenyl | |
| 57 | 3-Cl, 4-F-phenyl | |
| 58 | 3-Cl, 5-F-phenyl | |
| 59 | 3-Cl, 4-Br-phenyl | |
| 60 | 3-Cl, 5-Br-phenyl | |
| 61 | 3-F, 4-Cl-phenyl | |
| 62 | 3-F, 4-Br-phenyl | |
| 63 | 3-Br, 4-Cl-phenyl | |
| 64 | 3-Br, 4-F-phenyl | |
| 65 | 2,4,6-F$_3$-phenyl | |
| 66 | 2,3,4-Cl$_3$-phenyl | |
| 67 | 2,3,5-Cl$_3$-phenyl | |
| 68 | 2,3,6-Cl$_3$-phenyl | |
| 69 | 2,4,5-Cl$_3$-phenyl | |

TABLE 21-continued

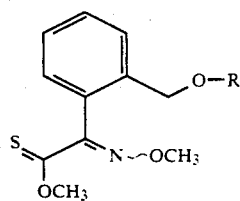

| No. | R | mp(°C.)/IR(cm$^{-1}$) |
|---|---|---|
| 70 | 2,4,6-Cl$_3$-phenyl | |
| 71 | 3,4,5-Cl$_3$-phenyl | |
| 72 | 2,4,6-BrS-phenyl | |
| 73 | 2,6-Cl$_2$-4-Br-phenyl | |
| 74 | 2,3,4,6-Cl$_4$-phenyl | |
| 75 | 2,3,5,6-Cl$_4$-phenyl | |
| 76 | F$_5$-phenyl | |
| 77 | Cl$_5$-phenyl | |
| 78 | Br$_5$-phenyl | |
| 79 | 2-CH$_3$-phenyl | |
| 80 | 3-CH$_3$-phenyl | |
| 81 | 4-CH$_3$-phenyl | |
| 82 | 2-C$_2$H$_5$-phenyl | |
| 83 | 3-C$_2$H$_5$-phenyl | |
| 84 | 4-C$_2$H$_5$-phenyl | |
| 85 | 2-n-C$_3$H$_7$-phenyl | |
| 86 | 3-n-C$_3$H$_7$-phenyl | |
| 87 | 4-n-C$_3$H$_7$-phenyl | |
| 88 | 2-i-C$_3$H$_7$-phenyl | |
| 89 | 3-i-C$_3$H$_7$-phenyl | |
| 90 | 4-i-C$_3$H$_7$-phenyl | |
| 91 | 2-s-C$_4$H$_9$-phenyl | |
| 92 | 3-s-C$_4$H$_9$-phenyl | |
| 93 | 4-s-C$_4$H$_9$-phenyl | |
| 94 | 2-t-C$_4$H$_9$-phenyl | |
| 95 | 3-t-C$_4$H$_9$-phenyl | |
| 96 | 4-t-C$_4$H$_9$-phenyl | |
| 97 | 2,3-(CH$_3$)$_2$-phenyl | |
| 98 | 2,4-(CH$_3$)$_2$-phenyl | |
| 99 | 2,5-(CH$_3$)$_2$-phenyl | |
| 100 | 2,6-(CH$_3$)$_2$-phenyl | |
| 101 | 3,4-(CH$_3$)$_2$-phenyl | |
| 102 | 3,5-(CH$_3$)$_2$-phenyl | |
| 103 | 2,3,4-(CH$_3$)$_3$-phenyl | |
| 104 | 2,3,5-(CH$_3$)$_3$-phenyl | |
| 105 | 2,3,6-(CH$_3$)$_3$-phenyl | |
| 106 | 2,4,5-(CH$_3$)$_3$-phenyl | |
| 107 | 2,4,6-(CH$_3$)$_3$-phenyl | |
| 108 | 3,4,5-(CH$_3$)$_3$-phenyl | |
| 109 | 2,3,4,6-(CH$_3$)$_4$-phenyl | |
| 110 | 2,3,5,6-(CH$_3$)$_4$-phenyl | |
| 111 | (CH$_3$)$_5$-phenyl | |
| 112 | 2,4-(C$_2$H$_5$)$_2$-phenyl | |
| 113 | 2,6-(C$_2$H$_5$)$_2$-phenyl | |
| 114 | 3,5-(C$_2$H$_5$)$_2$-phenyl | |
| 115 | 2,4,6-(C$_2$H$_5$)$_3$-phenyl | |
| 116 | 2,4-(i-C$_3$H$_7$)$_2$-phenyl | |
| 117 | 2,6-(i-C$_3$H$_7$)$_2$-phenyl | |
| 118 | 3,5-(i-C$_3$H$_7$)$_2$-phenyl | |
| 119 | 2,4,6-(i-C$_3$H$_7$)$_3$-phenyl | |
| 120 | 2,3-(t-C$_4$H$_9$)$_2$-phenyl | |
| 121 | 2,4-(t-C$_4$H$_9$)$_2$-phenyl | |
| 122 | 2,5-(t-C$_4$H$_9$)$_2$-phenyl | |
| 123 | 2,6-(t-C$_4$H$_9$)$_2$-phenyl | |
| 124 | 3,5-(t-C$_4$H$_9$)$_2$-phenyl | |
| 125 | 2,4,6-(t-C$_4$H$_9$)$_3$-phenyl | |
| 126 | 2-t-C$_4$H$_9$, 4-CH$_3$-phenyl | |
| 127 | 2-t-C$_4$H$_9$, 5-CH$_3$-phenyl | |
| 128 | 2,6-(t-C$_4$H$_9$)$_2$, 4-CH$_3$-phenyl | |
| 129 | 2-CH$_3$, 4-t-C$_4$H$_9$-phenyl | |
| 130 | 2-CH$_3$, 6-t-C$_4$H$_9$-phenyl | |
| 131 | 1-CH$_3$, 4-i-C$_3$H$_7$-phenyl | |
| 132 | 2-CH$_3$, 5-i-C$_3$H$_7$-phenyl | |
| 133 | 3-CH$_3$, 4-i-C$_3$H$_7$-phenyl | |
| 134 | 2-i-C$_3$H$_7$, 5-CH$_3$-phenyl | |
| 135 | 2,4-(t-C$_4$H$_9$)$_2$-6-i-C$_3$H$_7$-phenyl | |
| 136 | 2-cyclo-C$_6$H$_{11}$-phenyl | |
| 137 | 3-cyclo-C$_6$H$_{11}$-phenyl | |
| 138 | 4-cyclo-C$_6$H$_{11}$-phenyl | |
| 139 | 2,4-(cyclo-C$_6$H$_{11}$)$_2$-6-CH$_3$-phenyl | |

TABLE 21-continued

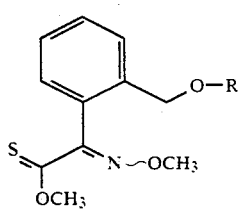

| No. | R | mp(°C.)/IR(cm$^{-1}$) |
|---|---|---|
| 140 | 2-CH$_3$, 4-cyclo-C$_6$H$_{11}$-phenyl | |
| 141 | 2-CH$_2$C$_6$H$_5$-phenyl | |
| 142 | 3-CH$_2$C$_6$H$_5$-phenyl | |
| 143 | 4-CH$_2$C$_6$H$_5$-phenyl | |
| 144 | 2-CH$_2$C$_6$H$_5$, 4-CH$_3$-phenyl | |
| 145 | 2-CH$_3$, 4-CH$_2$C$_6$H$_5$-phenyl | |
| 146 | 2-C$_6$H$_5$-phenyl | |
| 147 | 3-C$_6$H$_5$-phenyl | |
| 148 | 4-C$_6$H$_5$-phenyl | |
| 149 | 4-(2-i-C$_3$H$_7$—C$_6$H$_4$)-phenyl | |
| 150 | 4-C$_6$H$_5$, 2,6-(CH$_3$)$_2$-phenyl | |
| 151 | 2-Cl, 4-C$_6$H$_5$-phenyl | |
| 152 | 2-Br, 4-C$_6$H$_5$-phenyl | |
| 153 | 2-C$_6$H$_5$, 4-Cl-phenyl | |
| 154 | 2-C$_6$H$_5$, 4-Br-phenyl | |
| 155 | 2-CH$_2$C$_6$H$_5$, 4-Cl-phenyl | |
| 156 | 2-CH$_2$C$_6$H$_5$, 4-Br-phenyl | |
| 157 | 2-Cl, 4-CH$_2$C$_6$H$_5$-phenyl | |
| 158 | 2-Br, 4-CH$_2$C$_6$H$_5$-phenyl | |
| 159 | 2-cyclo-C$_6$H$_{11}$, 4-Cl-phenyl | |
| 160 | 2-cyclo-C$_6$H$_{11}$, 4-Br-phenyl | |
| 161 | 2-Cl, 4-cyclo-C$_6$H$_{11}$-phenyl | |
| 162 | 2-Br, 4-cyclo-C$_6$H$_{11}$-phenyl | |
| 163 | 3-OCH$_3$-phenyl | |
| 164 | 2,4-(OCH$_3$)$_2$-phenyl | |
| 165 | 2-CF$_3$-phenyl | |
| 166 | 3-CF$_3$-phenyl | |
| 167 | 4-CF$_3$-phenyl | |
| 168 | 2-NO$_2$-phenyl | |
| 169 | 3-NO$_2$-phenyl | |
| 170 | 4-NO$_2$-phenyl | |
| 171 | 2-CN-phenyl | |
| 172 | 3-CN-phenyl | |
| 173 | 4-CN-phenyl | |
| 174 | 2-CH$_3$, 3-Cl-phenyl | |
| 175 | 2-CH$_3$, 4-Cl-phenyl | |
| 176 | 2-CH$_3$, 5-Cl-phenyl | |
| 177 | 2-CH$_3$, 6-Cl-phenyl | |
| 178 | 2-CH$_3$, 3-F-phenyl | |
| 179 | 2-CH$_3$, 4-F-phenyl | |
| 180 | 2-CH$_3$, 5-F-phenyl | |
| 181 | 2-CH$_3$, 6-F-phenyl | |
| 182 | 2-CH$_3$, 3-Br-phenyl | |
| 183 | 2-CH$_3$, 4-Br-phenyl | |
| 184 | 2-CH$_3$, 5-Br-phenyl | |
| 185 | 2-CH$_3$, 6-Br-phenyl | |
| 186 | 2-Cl, 3-CH$_3$-phenyl | |
| 187 | 2-Cl, 4-CH$_3$-phenyl | |
| 188 | 2-Cl, 5-CH$_3$-phenyl | |
| 189 | 2-Cl, 3-i-C$_3$H$_7$ | |
| 190 | 2-F, 3-CH$_3$-phenyl | |
| 191 | 2-F, 4-CH$_3$-phenyl | |
| 192 | 2-F, 5-CH$_3$-phenyl | |
| 193 | 2-Br, 3-CH$_3$-phenyl | |
| 194 | 2-Br, 4-CH$_3$-phenyl | |
| 195 | 3-CH$_3$, 4-Cl-phenyl | |
| 196 | 3-CH$_3$, 5-Cl-phenyl | |
| 197 | 2-Br, 5-CH$_3$-phenyl | |
| 198 | 3-CH$_3$, 4-F-phenyl | |
| 199 | 3-CH$_3$, 5-F-phenyl | |
| 200 | 3-CH$_3$, 4-Br-phenyl | |
| 201 | 3-CH$_3$, 5-Br-phenyl | |
| 202 | 3-F, 4-CH$_3$-phenyl | |
| 203 | 3-Cl, 4-CH$_3$-phenyl | |
| 204 | 3-Br, 4-CH$_3$-phenyl | |
| 205 | 2-Cl, 4,5-(CH$_3$)$_2$-phenyl | |
| 206 | 2-Br, 4,5-(CH$_3$)$_2$-phenyl | |
| 207 | 2-Cl, 3,5-(CH$_3$)$_2$-phenyl | |
| 208 | 2-Br, 3,5-(CH$_3$)$_2$-phenyl | |
| 209 | 2,6-Cl$_2$, 4-CH$_3$-phenyl | |

TABLE 21-continued

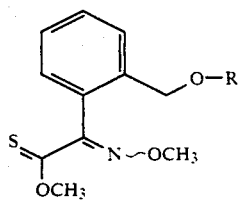

| No. | R | mp(°C.)/IR(cm$^{-1}$) |
|---|---|---|
| 210 | 2,6-F$_2$, 4-CH$_3$-phenyl | |
| 211 | 2,6-Br$_2$, 4-CH$_3$-phenyl | |
| 212 | 2,4-Cl$_2$, 6-CH$_3$-phenyl | |
| 213 | 2,4-F$_2$, 6-CH$_3$-phenyl | |
| 214 | 2,4-Br$_2$, 6-CH$_3$-phenyl | |
| 215 | 2,6-(CH$_3$)$_2$, 4-F-phenyl | |
| 216 | 2,6-(CH$_3$)$_2$, 4-Cl-phenyl | |
| 217 | 2,6-(CH$_3$)$_2$, 4-Br-phenyl | |
| 218 | 3,5-(CH$_3$)$_2$, 4-F-phenyl | |
| 219 | 3,5-(CH$_3$)$_2$, 4-Cl-phenyl | |
| 220 | 3,5-(CH$_3$)$_2$, 4-Br-phenyl | |
| 221 | 2,3,6-(CH$_3$)$_3$, 4-F-phenyl | |
| 222 | 2,3,6-(CH$_3$)$_3$, 4-Cl-phenyl | |
| 223 | 2,3,6-(CH$_3$)$_3$, 4-Br-phenyl | |
| 224 | 2,4-(CH$_3$)$_2$, 6-F-phenyl | |
| 225 | 2,4-(CH$_3$)$_2$, 6-Cl-phenyl | |
| 226 | 2,4-(CH$_3$)$_2$, 6-Br-phenyl | |
| 227 | 2-i-C$_3$H$_7$, 4-Cl, 5-CH$_3$-phenyl | |
| 228 | 2-Cl, 4-NO$_2$-phenyl | |
| 229 | 2-NO$_2$, 4-Cl-phenyl | |
| 230 | 2-OCH$_3$, 5-NO$_2$-phenyl | |
| 231 | 2,4-Cl$_2$, 5-NO$_2$-phenyl | |
| 232 | 2,4-Cl$_2$, 6-NO$_2$-phenyl | |
| 233 | 2,6-Cl$_2$, 4-NO$_2$-phenyl | |
| 234 | 2,6-Br$_2$, 4-NO$_2$-phenyl | |
| 235 | 2,6-I$_2$, 4-NO$_2$-phenyl | |
| 236 | 2-C$_6$H$_5$O-phenyl | |
| 237 | 3-C$_6$H$_5$O-phenyl | |
| 238 | 4-C$_6$H$_5$O-phenyl | |
| 239 | 3-t-C$_4$H$_9$O-phenyl | |
| 240 | 4-t-C$_4$H$_9$O-phenyl | |
| 241 | 1-naphthyl | |
| 242 | 2-naphthyl | |
| 243 | 2-pyridyl | |
| 244 | 6-methyl-2-pyridyl | |
| 245 | 6-ethyl-2-pyridyl | |
| 246 | 6-n-propyl-2-pyridyl | |
| 247 | 6-iso-propyl-2-pyridyl | |
| 248 | 6-n-butyl-2-pyridyl | |
| 249 | 6-tert.-butyl-2-pyridyl | |
| 250 | 6-n-pentyl-2-pyridyl | |
| 251 | 6-n-hexyl-2-pyridyl | |
| 252 | 6-phenyl-2-pyridyl | |
| 253 | 6-benzyl-2-pyridyl | |
| 254 | 6-trifluoromethyl-2-pyridyl | |
| 255 | 6-methoxy-2-pyridyl | |
| 256 | 6-chloro-2-pyridyl | |
| 257 | 3,6-dimethyl-2-pyridyl | |
| 258 | 3,6-diethyl-2-pyridyl | |
| 259 | 4,6-dimethyl-2-pyridyl | |
| 260 | 5,6-dimethyl-2-pyridyl | |
| 261 | 4-phenyl-6-methyl-2-pyridyl | |
| 262 | 4,6-diphenyl-2-pyridyl | |
| 263 | 3,4-dichloro-6-methyl-2-pyridyl | |
| 264 | 3,4,5-trichloro-6-phenyl-2-pyridyl | |
| 265 | 4-trifluoromethyl-6-methyl-2-pyridyl | |
| 266 | 3-cyano-6-methyl-2-pyridyl | |
| 267 | 3-cyano-6-ethyl-2-pyridyl | |
| 268 | 3-cyano-6-n-propyl-2-pyridyl | |
| 269 | 3-cyano-6-iso-propyl-2-pyridyl | |
| 270 | 3-cyano-6-cyclo-propyl-2-pyridyl | |
| 271 | 3-cyano-6-n-butyl-2-pyridyl | |
| 272 | 3-cyano-6-tert.-butyl-2-pyridyl | |
| 273 | 3-cyano-6-cyclo-hexyl-2-pyridyl | |
| 274 | 3-cyano-6-phenyl-2-pyridyl | |
| 275 | 3-cyano-4,6-dimethyl-2-pyridyl | |
| 276 | 3,5,6-trichloro-2-pyridyl | |
| 277 | 5-trifluoromethyl-2-pyridyl | |
| 278 | 3-chloro-5-trifluoromethyl-2-pyridyl | |
| 279 | 2-quinolyl | |

TABLE 21-continued

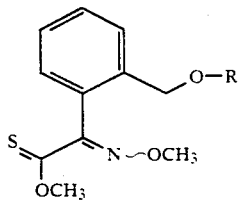

| No. | R | mp(°C.)/IR(cm$^{-1}$) |
|---|---|---|
| 280 | 3-methyl-2-quinolyl | |
| 281 | 4-methyl-2-quinolyl | |
| 282 | 4-ethyl-2-quinolyl | |
| 283 | 4-phenyl-2-quinolyl | |
| 284 | 6-methyl-2-quinolyl | |
| 285 | 6-chloro-2-quinolyl | |
| 286 | 8-methyl-2-quinolyl | |
| 287 | 8-chloro-2-quinolyl | |
| 288 | 3,4-dimethyl-2-quinolyl | |
| 289 | 4-methyl-8-methoxy-2-quinolyl | |
| 290 | 4-phenyl-8-ethoxy-2-quinolyl | |
| 291 | 4-methyl-8-chloro-2-quinolyl | |
| 292 | 4-methyl-8-fluoro-2-quinolyl | |
| 293 | 4-quinolyl | |
| 294 | 2-methyl-4-quinolyl | |
| 295 | 2-trifluoromethyl-4-quinolyl | |
| 296 | 2-iso-propyl-4-quinolyl | |
| 297 | 2-n-pentyl-4-quinolyl | |
| 298 | 2-phenyl-4-quinolyl | |
| 299 | 2,6-dimethyl-4-quinolyl | |
| 300 | 2-methyl-6-chloro-4-quinolyl | |
| 301 | 2-methyl-6-fluoro-4-quinolyl | |
| 302 | 8-quinolyl | |
| 303 | 2-methyl-8-quinolyl | |
| 304 | 5,7-dichloro-8-quinolyl | |
| 305 | 4,6-dimethyl-2-pyrimidinyl | |
| 306 | 4-trifluoromethyl-2-pyrimidinyl | |
| 307 | 4,5,6-trimethyl-2-pyrimidinyl | |
| 308 | 4-benzyl-6-methyl-2-pyrimidinyl | |
| 309 | 4-methyl-6-phenyl-2-pyrimidinyl | |
| 310 | 4,6-dimethyl-5-chloro-2-pyrimidinyl | |
| 311 | 2,6-dimethyl-4-pyrimidinyl | |
| 312 | 2,6-bis-(trifluoromethyl)-4-pyrimidinyl | |
| 313 | 2-iso-propyl-6-methyl-4-pyrimidinyl | |
| 314 | 2-cyclo-propyl-6-methyl-4-pyrimidinyl | |
| 315 | 2-methyl-6-methoxymethyl-4-pyrimidinyl | |
| 316 | 2-iso-propyl-6-methoxymethyl-4-pyrimidinyl | |
| 317 | 2-phenyl-4-pyrimidinyl | |
| 318 | 3,5-dimethyl-4-pyrimidinyl | |
| 319 | 2-methyl-6-trifluoromethyl-4-pyrimidinyl | |
| 320 | 2-n-propyl-6-trifluoromethyl-4-pyrimidinyl | |
| 321 | 2-iso-propyl-6-trifluoromethyl-4-pyrimidinyl | |
| 322 | 2-methyl-5-chloro-6-trifluoromethyl-4-pyrimidinyl | |
| 323 | 2-n-propyl-5-chloro-6-trifluoromethyl-4-pyrimidinyl | |
| 324 | 2-iso-propyl-5-chloro-6-trifluoromethyl-4-pyrimidinyl | |
| 325 | 2-tert.-butyl-5-chloro-6-trifluoromethyl-4-pyrimidinyl | |

TABLE 22

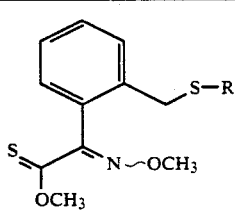

| No. | R | mp(°C.)/IR(cm$^{-1}$) |
|---|---|---|
| 1 | methyl | |
| 2 | ethyl | |
| 3 | n-propyl | |
| 4 | iso-propyl | |
| 5 | n-butyl | |
| 6 | s-butyl | |
| 7 | iso-butyl | |
| 8 | tert.-butyl | |
| 9 | pentyl | |
| 10 | hexyl | |
| 11 | phenyl | |
| 12 | 2-F-phenyl | |
| 13 | 3-F-phenyl | |
| 14 | 4-F-phenyl | |

TABLE 22-continued

Structure: 2-(CH2-S-R)-phenyl group attached to C(=S)(OCH3) and =N-OCH3

| No. | R | mp(°C.)/IR(cm$^{-1}$) |
|---|---|---|
| 15 | 2-Cl-phenyl | 1661, 1451, 1443, 1139, 1115, 1043, 1035, 1024, 846, 749 |
| 16 | 3-Cl-phenyl | |
| 17 | 4-Cl-phenyl | |
| 18 | 2-Br-phenyl | |
| 19 | 3-Br-phenyl | |
| 20 | 4-Br-phenyl | |
| 21 | 2-I-phenyl | |
| 22 | 3-I-phenyl | |
| 23 | 4-I-phenyl | |
| 24 | 2-CN-phenyl | |
| 25 | 3-CN-phenyl | |
| 26 | 4-CN-phenyl | |
| 27 | 2,3-F$_2$-phenyl | |
| 28 | 2,4-F$_2$-phenyl | |
| 29 | 2,3-Cl$_2$-phenyl | |
| 30 | 2,4-Cl$_2$-phenyl | |
| 31 | 2,5-Cl$_2$-phenyl | |
| 32 | 2,6-Cl$_2$-phenyl | |
| 33 | 3,4-Cl$_2$-phenyl | |
| 34 | 3,5-Cl$_2$-phenyl | |
| 35 | 2,4-Br$_2$-phenyl | |
| 36 | 2,5-Br$_2$-phenyl | |
| 37 | 2,6-Br$_2$-phenyl | |
| 38 | 2,4-I$_2$-phenyl | |
| 39 | 2-Cl, 3-F-phenyl | |
| 40 | 2-Cl, 4-F-phenyl | |
| 41 | 2-Cl, 5-F-phenyl | |
| 42 | 2-Cl, 6-F-phenyl | |
| 43 | 2-Cl, 3-Br-phenyl | |
| 44 | 2-Cl, 4-Br-phenyl | |
| 45 | 2-Cl, 5-Br-phenyl | |
| 46 | 2-Cl, 6-Br-phenyl | |
| 47 | 2-Br, 3-Cl-phenyl | |
| 48 | 2-Br, 4-Cl-phenyl | |
| 49 | 2-Br, 3-F-phenyl | |
| 50 | 2-Br, 4-F-phenyl | |
| 51 | 2-Br, 5-F-phenyl | |
| 52 | 2-Br, 6-F-phenyl | |
| 53 | 2-F, 3-Cl-phenyl | |
| 54 | 2-F, 4-Cl-phenyl | |
| 55 | 2-F, 5-Cl-phenyl | |
| 56 | 3-Cl, 4-F-phenyl | |
| 57 | 3-Cl, 5-F-phenyl | |
| 58 | 3-Cl, 4-Br-phenyl | |
| 59 | 3-Cl, 5-Br-phenyl | |
| 60 | 3-F, 4-Cl-phenyl | |
| 61 | 3-F, 4-Br-phenyl | |
| 62 | 3-Br, 4-Cl-phenyl | |
| 63 | 3-Br, 4-F-phenyl | |
| 64 | 2,4,6-F$_3$-phenyl | |
| 65 | 2,3,4,-Cl$_3$-phenyl | |
| 66 | 2,3,5-Cl$_3$-phenyl | |
| 67 | 2,3,6-Cl$_3$-phenyl | |
| 68 | 2,4,5-Cl$_3$-phenyl | |
| 69 | 2,4,6-Cl$_3$-phenyl | |
| 70 | 3,4,5-Cl$_3$-phenyl | |
| 71 | 2,4,6-Br$_3$-phenyl | |
| 72 | 2,6-Cl$_2$-4-Br-phenyl | |
| 73 | 2,3,4,6-Cl$_4$-phenyl | |
| 74 | 2,3,5,6-Cl$_4$-phenyl | |
| 75 | F$_5$-phenyl | |
| 76 | Cl$_5$-phenyl | |
| 77 | Br$_5$-phenyl | |
| 78 | 2-CH$_3$-phenyl | |
| 79 | 3-CH$_3$-phenyl | |
| 80 | 4-CH$_3$-phenyl | |
| 81 | 2-C$_2$H$_5$-phenyl | |
| 82 | 3-C$_2$H$_5$-phenyl | |
| 83 | 4-C$_2$H$_5$-phenyl | |
| 84 | 2-n-C$_3$H$_7$-phenyl | |
| 85 | 3-n-C$_3$H$_7$-phenyl | |
| 86 | 4-n-C$_3$H$_7$-phenyl | |
| 87 | 2-i-C$_3$H$_7$-phenyl | |
| 88 | 3-i-C$_3$H$_7$-phenyl | |
| 89 | 4-i-C$_3$H$_7$-phenyl | |
| 90 | 2-s-C$_4$H$_9$-phenyl | |
| 91 | 3-s-C$_4$H$_9$-phenyl | |
| 92 | 4-s-C$_4$H$_9$-phenyl | |
| 93 | 2-t-C$_4$H$_9$-phenyl | |
| 94 | 3-t-C$_4$H$_9$-phenyl | |
| 95 | 4-t-C$_4$H$_9$-phenyl | |
| 96 | 2,3-(CH$_3$)$_2$-phenyl | |
| 97 | 2,4-(CH$_3$)$_2$-phenyl | |
| 98 | 2,5-(CH$_3$)$_2$-phenyl | |
| 99 | 2,6-(CH$_3$)$_2$-phenyl | |
| 100 | 3,4-(CH$_3$)$_2$-phenyl | |
| 101 | 3,5-(CH$_3$)$_2$-phenyl | |
| 102 | 2,3,4-(CH$_3$)$_3$-phenyl | |
| 103 | 2,3,5-(CH$_3$)$_3$-phenyl | |
| 104 | 2,3,6-(CH$_3$)$_3$-phenyl | |
| 105 | 2,4,5-(CH$_3$)$_3$-phenyl | |
| 106 | 2,4,6-(CH$_3$)$_3$-phenyl | |
| 107 | 3,4,5-(CH$_3$)$_3$-phenyl | |
| 108 | 2,3,4,6-(CH$_3$)$_4$-phenyl | |
| 109 | 2,3,5,6-(CH$_3$)$_4$-phenyl | |
| 110 | (CH$_3$)$_5$-phenyl | |
| 111 | 2,4-(C$_2$H$_5$)$_2$-phenyl | |
| 112 | 2,6-(C$_2$H$_5$)$_2$-phenyl | |
| 113 | 3,5-(C$_2$H$_5$)$_2$-phenyl | |
| 114 | 2,4,6-(C$_2$H$_5$)$_3$-phenyl | |
| 115 | 2,4-(i-C$_3$H$_7$)$_2$-phenyl | |
| 116 | 2,6-(i-C$_3$H$_7$)$_2$-phenyl | |
| 117 | 3,5-(i-C$_3$H$_7$)$_2$-phenyl | |
| 118 | 2,4,6-(i-C$_3$H$_7$)$_3$-phenyl | |
| 119 | 2,3-(t-C$_4$H$_9$)$_2$-phenyl | |
| 120 | 2,4-(t-C$_4$H$_9$)$_2$-phenyl | |
| 121 | 2,5-(t-C$_4$H$_9$)$_2$-phenyl | |
| 122 | 2,6-(t-C$_4$H$_9$)$_2$-phenyl | |
| 123 | 3,5-(t-C$_4$H$_9$)$_2$-phenyl | |
| 124 | 2,4,6-(t-C$_4$H$_9$)$_3$-phenyl | |
| 125 | 2-t-C$_4$H$_9$, 4-CH$_3$-phenyl | |
| 126 | 2-t-C$_4$H$_9$, 5-CH$_3$-phenyl | |
| 127 | 2,6-(t-C$_4$H$_9$)$_2$, 4-CH$_3$-phenyl | |
| 128 | 2-CH$_3$, 4-t-C$_4$H$_9$-phenyl | |
| 129 | 2-CH$_3$, 6-t-C$_4$H$_9$-phenyl | |
| 130 | 2-CH$_3$, 4-i-C$_3$H$_7$-phenyl | |
| 131 | 2-CH$_3$, 5-i-C$_3$H$_7$-phenyl | |
| 132 | 3-CH$_3$, 4-i-C$_3$H$_7$-phenyl | |
| 133 | 2-i-C$_3$H$_7$, 5-CH$_3$-phenyl | |
| 134 | 2,4-(t-C$_4$H$_9$)$_2$-6-i-C$_3$H$_7$-phenyl | |
| 135 | 2-cyclo-C$_6$H$_{11}$-phenyl | |
| 136 | 3-cyclo-C$_6$H$_{11}$-phenyl | |
| 137 | 4-cyclo-C$_6$H$_{11}$-phenyl | |
| 138 | 2,4-(cyclo-C$_6$H$_{11}$)$_2$-6-CH$_3$-phenyl | |
| 139 | 2-CH$_3$, 4-cyclo-C$_6$H$_{11}$-phenyl | |
| 140 | 2-CH$_2$C$_6$H$_5$-phenyl | |
| 141 | 3-CH$_2$C$_6$H$_5$-phenyl | |
| 142 | 4-CH$_2$C$_6$H$_5$-phenyl | |
| 143 | 2-CH$_2$C$_6$H$_5$, 4-CH$_3$-phenyl | |
| 144 | 2-CH$_3$, 4-CH$_2$C$_6$H$_5$-phenyl | |
| 145 | 2-C$_6$H$_5$-phenyl | |
| 146 | 3-C$_6$H$_5$-phenyl | |
| 147 | 4-C$_6$H$_5$-phenyl | |
| 148 | 4-(2-i-C$_3$H$_7$—C$_6$H$_4$)-phenyl | |
| 149 | 4-C$_6$H$_5$, 2,6-(CH$_3$)$_2$-phenyl | |
| 150 | 2-Cl, 4-C$_6$H$_5$-phenyl | |
| 151 | 2-Br, 4-C$_6$H$_5$-phenyl | |
| 152 | 2-C$_6$H$_5$, 4-Cl-phenyl | |
| 153 | 2-C$_6$H$_5$, 4-Br-phenyl | |

TABLE 22-continued

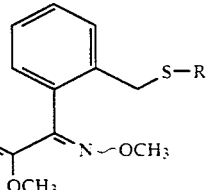

| No. | R | mp(°C.)/IR(cm$^{-1}$) |
|---|---|---|
| 154 | 2-CH$_2$C$_6$H$_5$, 4-Cl-phenyl | |
| 155 | 2-CH$_2$C$_6$H$_5$, 4-Br-phenyl | |
| 156 | 2-Cl, 4-CH$_2$C$_6$H$_5$-phenyl | |
| 157 | 2-Br, 4-CH$_2$C$_6$H$_5$-phenyl | |
| 158 | 2-cyclo-C$_6$H$_{11}$, 4-Cl-phenyl | |
| 159 | 2-cyclo-C$_6$H$_{11}$, 4-Br-phenyl | |
| 160 | 2-Cl, 4-cyclo-C$_6$H$_{11}$-phenyl | |
| 161 | 2-Br, 4-cyclo-C$_6$H$_{11}$-phenyl | |
| 162 | 3-OCH$_3$-phenyl | |
| 163 | 2,4-(OCH$_3$)$_2$-phenyl | |
| 164 | 2-CF$_3$-phenyl | |
| 165 | 3-CF$_3$-phenyl | |
| 166 | 4-CF$_3$-phenyl | |
| 167 | 2-NO$_2$-phenyl | |
| 168 | 3-NO$_2$-phenyl | |
| 169 | 4-NO$_2$-phenyl | |
| 170 | 2-CN-phenyl | |
| 171 | 3-CN-phenyl | |
| 172 | 4-CN-phenyl | |
| 173 | 2-CH$_3$, 3-Cl-phenyl | |
| 174 | 2-CH$_3$, 4-Cl-phenyl | |
| 175 | 2-CH$_3$, 5-Cl-phenyl | |
| 176 | 2-CH$_3$, 6-Cl-phenyl | |
| 177 | 2-CH$_3$, 3-F-phenyl | |
| 178 | 2-CH$_3$, 4-F-phenyl | |
| 179 | 2-CH$_3$, 5-F-phenyl | |
| 180 | 2-CH$_3$, 6-F-phenyl | |
| 181 | 2-CH$_3$, 3-Br-phenyl | |
| 182 | 2-CH$_3$, 4-Br-phenyl | |
| 183 | 2-CH$_3$, 5-Br-phenyl | |
| 184 | 2-CH$_3$, 6-Br-phenyl | |
| 185 | 2-Cl, 3-CH$_3$-phenyl | |
| 186 | 2-Cl, 4-CH$_3$-phenyl | |
| 187 | 2-Cl, 5-CH$_3$-phenyl | |
| 188 | 2-Cl, 3-i-C$_3$H$_7$ | |
| 189 | 2-F, 3-CH$_3$-phenyl | |
| 190 | 2-F, 4-CH$_3$-phenyl | |
| 191 | 2-F, 5-CH$_3$-phenyl | |
| 192 | 2-Br, 3-CH$_3$-phenyl | |
| 193 | 2-Br, 4-CH$_3$-phenyl | |
| 194 | 3-CH$_3$, 4-Cl-phenyl | |
| 195 | 3-CH$_3$, 5-Cl-phenyl | |
| 196 | 2-Br, 5-CH$_3$-phenyl | |
| 197 | 3-CH$_3$, 4-F-phenyl | |
| 198 | 3-CH$_3$, 5-F-phenyl | |
| 199 | 3-CH$_3$, 4-Br-phenyl | |
| 200 | 3-CH$_3$, 5-Br-phenyl | |
| 201 | 3-F, 4-CH$_3$-phenyl | |
| 202 | 3-Cl, 4-CH$_3$-phenyl | |
| 203 | 3-Br, 4-CH$_3$-phenyl | |
| 204 | 2-Cl, 4,5-(CH$_3$)$_2$-phenyl | |
| 205 | 2-Br, 4,5-(CH$_3$)$_2$-phenyl | |
| 206 | 2-Cl, 3,5-(CH$_3$)$_2$-phenyl | |
| 207 | 2-Br, 3,5-(CH$_3$)$_2$-phenyl | |
| 208 | 2,6-Cl$_2$, 4-CH$_3$-phenyl | |
| 209 | 2,6-F$_2$, 4-CH$_3$-phenyl | |
| 210 | 2,6-Br$_2$, 4-CH$_3$-phenyl | |
| 211 | 2,4-Cl$_2$, 6-CH$_3$-phenyl | |
| 212 | 2,4-F$_2$, 6-CH$_3$-phenyl | |
| 213 | 2,4-Br$_2$, 6-CH$_3$-phenyl | |
| 214 | 2,6-(CH$_3$)$_2$, 4-F-phenyl | |
| 215 | 2,6-(CH$_3$)$_2$, 4-Cl-phenyl | |
| 216 | 2,6-(CH$_3$)$_2$, 4-Br-phenyl | |
| 217 | 3,5-(CH$_3$)$_2$, 4-F-phenyl | |
| 218 | 3,5-(CH$_3$)$_2$, 4-Cl-phenyl | |
| 219 | 3,5-(CH$_3$)$_2$, 4-Br-phenyl | |
| 220 | 2,3,6-(CH$_3$)$_3$, 4-F-phenyl | |
| 221 | 2,3,6-(CH$_3$)$_3$, 4-Cl-phenyl | |
| 222 | 2,3,6-(CH$_3$)$_3$, 4-Br-phenyl | |
| 223 | 2,4-(CH$_3$)$_2$, 6-F-phenyl | |

TABLE 22-continued

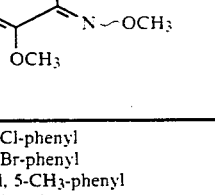

| No. | R | mp(°C.)/IR(cm$^{-1}$) |
|---|---|---|
| 224 | 2,4-(CH$_3$)$_2$, 6-Cl-phenyl | |
| 225 | 2,4-(CH$_3$)$_2$, 6-Br-phenyl | |
| 226 | 2-i-C$_3$H$_7$, 4-Cl, 5-CH$_3$-phenyl | |
| 227 | 2-Cl, 4-NO$_2$-phenyl | |
| 228 | 2-NO$_2$, 4-Cl-phenyl | |
| 229 | 2-OCH$_3$, 5-NO$_2$-phenyl | |
| 230 | 2,4-Cl$_2$, 5-NO$_2$-phenyl | |
| 231 | 2,4-Cl$_2$, 6-NO$_2$-phenyl | |
| 232 | 2,6-Cl$_2$, 4-NO$_2$-phenyl | |
| 233 | 2,6-Br$_2$, 4-NO$_2$-phenyl | |
| 234 | 2,6-I$_2$, 4-NO$_2$-phenyl | |
| 235 | 2-C$_6$H$_5$O-phenyl | |
| 236 | 3-C$_6$H$_5$O-phenyl | |
| 237 | 4-C$_6$H$_5$O-phenyl | |
| 238 | 3-t-C$_4$H$_9$O-phenyl | |
| 239 | 4-t-C$_4$H$_9$O-phenyl | |
| 240 | 1-naphthyl | |
| 241 | 2-naphthyl | |
| 242 | 2-pyridyl | |
| 243 | 6-methyl-2-pyridyl | 89-94° C. |
| 244 | 6-ethyl-2-pyridyl | |
| 245 | 6-n-propyl-2-pyridyl | |
| 246 | 6-iso-propyl-2-pyridyl | |
| 247 | 6-n-butyl-2-pyridyl | |
| 248 | 6-tert.-butyl-2-pyridyl | |
| 249 | 6-n-pentyl-2-pyridyl | |
| 250 | 6-n-hexyl-2-pyridyl | |
| 251 | 6-phenyl-2-pyridyl | |
| 252 | 6-benzyl-2-pyridyl | |
| 253 | 6-trifluoromethyl-2-pyridyl | |
| 254 | 6-methoxy-2-pyridyl | |
| 255 | 6-chloro-2-pyridyl | |
| 256 | 3,6-dimethyl-2-pyridyl | |
| 257 | 3,6-diethyl-2-pyridyl | |
| 258 | 4,6-dimethyl-2-pyridyl | |
| 259 | 5,6-dimethyl-2-pyridyl | |
| 260 | 4-phenyl-6-methyl-2-pyridyl | |
| 261 | 4,6-diphenyl-2-pyridyl | |
| 262 | 3,4-dichloro-6-methyl-2-pyridyl | |
| 263 | 3,4,5-trichloro-6-phenyl-2-pyridyl | |
| 264 | 4-trifluoromethyl-6-methyl-2-pyridyl | |
| 265 | 3-cyano-6-methyl-2-pyridyl | |
| 266 | 3-cyano-6-ethyl-2-pyridyl | |
| 267 | 3-cyano-6-n-propyl-2-pyridyl | |
| 268 | 3-cyano-6-iso-propyl-2-pyridyl | |
| 269 | 3-cyano-6-cyclo-propyl-2-pyridyl | |
| 270 | 3-cyano-6-n-butyl-2-pyridyl | |
| 271 | 3-cyano-6-tert.-butyl-2-pyridyl | |
| 272 | 3-cyano-6-cyclo-hexyl-2-pyridyl | |
| 273 | 3-cyano-6-phenyl-2-pyridyl | |
| 274 | 3-cyano-4,6-dimethyl-2-pyridyl | |
| 275 | 3,5,6-trichloro-2-pyridyl | |
| 276 | 5-trifluoromethyl-2-pyridyl | |
| 277 | 3-chloro-5-trifluoromethyl-2-pyridyl | |
| 278 | 2-quinolyl | |
| 279 | 3-methyl-2-quinolyl | |
| 280 | 4-methyl-2-quinolyl | |
| 281 | 4-ethyl-2-quinolyl | |
| 282 | 4-phenyl-2-quinolyl | |
| 283 | 6-methyl-2-quinolyl | |
| 284 | 6-chloro-2-quinolyl | |
| 285 | 8-methyl-2-quinolyl | |
| 286 | 8-chloro-2-quinolyl | |
| 287 | 3,4-dimethyl-2-quinolyl | |
| 288 | 4-methyl-8-methoxy-2-quinolyl | |
| 289 | 4-phenyl-8-ethoxy-2-quinolyl | |
| 290 | 4-methyl-8-chloro-2-quinolyl | |
| 291 | 4-methyl-8-fluoro-2-quinolyl | |
| 292 | 4-quinolyl | |
| 293 | 2-methyl-4-quinolyl | |

TABLE 22-continued

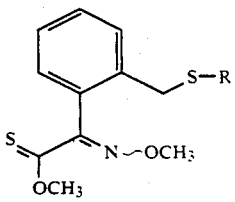

| No. | R | mp(°C.)/IR(cm⁻¹) |
|---|---|---|
| 294 | 2-trifluoromethyl-4-quinolyl | |
| 295 | 2-iso-propyl-4-quinolyl | |
| 296 | 2-n-pentyl-4-quinolyl | |
| 297 | 2-phenyl-4-quinolyl | |
| 298 | 2,6-dimethyl-4-quinolyl | |
| 299 | 2-methyl-6-chloro-4-quinolyl | |
| 300 | 2-methyl-6-fluoro-4-quinolyl | |
| 301 | 8-quinolyl | |
| 302 | 2-methyl-8-quinolyl | |
| 303 | 5,7-dichloro-8-quinolyl | |
| 304 | 4,6-dimethyl-2-pyrimidinyl | |
| 305 | 4-trifluoromethyl-2-pyrimidinyl | |
| 306 | 4,5,6-trimethyl-2-pyrimidinyl | |
| 307 | 4-benzyl-6-methyl-2-pyrimidinyl | |
| 308 | 4-methyl-6-phenyl-2-pyrimidinyl | |
| 309 | 4,6-dimethyl-5-chloro-2-pyrimidinyl | |
| 310 | 2,6-dimethyl-4-pyrimidinyl | |
| 311 | 2,6-bis-(trifluoromethyl)-4-pyrimidinyl | |
| 312 | 2-iso-propyl-6-methyl-4-pyrimidinyl | |
| 313 | 2-cyclo-propyl-6-methyl-4-pyrimidinyl | |
| 314 | 2-methyl-6-methoxymethyl-4-pyrimidinyl | |
| 315 | 2-iso-propyl-6-methoxymethyl-4-pyrimidinyl | |
| 316 | 2-phenyl-4-pyrimidinyl | |
| 317 | 3,5-dimethyl-4-pyrimidinyl | |
| 318 | 2-methyl-6-trifluoromethyl-4-pyrimidinyl | |
| 319 | 2-n-propyl-6-trifluoromethyl-4-pyrimidinyl | |
| 320 | 2-iso-propyl-6-trifluoromethyl-4-pyrimidinyl | |
| 321 | 2-methyl-5-chloro-6-trifluoromethyl-4-pyrimidinyl | |
| 322 | 2-n-propyl-5-chloro-6-trifluoromethyl-4-pyrimidinyl | |
| 323 | 2-iso-propyl-5-chloro-6-trifluoromethyl-4-pyrimidinyl | |
| 324 | 2-tert.-butyl-5-chloro-6-trifluoromethyl-4-pyrimidinyl | |
| 325 | 6-EtO-benzothiazol-2-yl | |
| 326 | benzoxazol-2-yl | |
| 327 | 1-Me-imidazol-2-yl | |
| 328 | 4-but-1H-imidazol-2-yl | |
| 329 | 2-thiazolin-2-yl | |
| 330 | 5-CF₃-benzimidazol-2-yl | |
| 331 | 1-Ph-tetrazol-5-yl | |
| 332 | 5-CF₃-benzothiazol-2-yl | |
| 333 | 4,4-Me₂-5-methylene-2-thiazolin-2-yl | |
| 334 | 6-Cl-4-Me-benzothiazol-2-yl | |
| 335 | 5-Me-benzothiazol-2-yl | |
| 336 | 4-Cl-benzothiazol-2-yl | |
| 337 | 1-(3-NO₂—Ph)tetrazol-5-yl | |
| 338 | 2-thienyl | |
| 339 | 5-Me-benzoxazol-2-yl | |
| 340 | 7-Cl-benzothiazol-2-yl | |
| 341 | 5,6-Cl₃-1H-benzimidazol-2-yl | |
| 342 | 5-Cl-benzoxazol-2-yl | |
| 343 | 6-Cl-benzothiazol-2-yl | |
| 344 | 2-Ph-thiazol-2-yl | |
| 345 | 3-CN-4,6-Me₂-2-pyridyl | |
| 346 | 1-Ph-1,2,4-triazol-3-yl | |
| 347 | 1-Pri-benzimidazol-2-yl | |
| 348 | 5-Br-benzothiazol-2-yl | |
| 349 | 5-Br-1H-benzimidazol-2-yl | |
| 350 | 7-Cl-4-MeO-benzothiazol-2-yl | |
| 351 | 1H-benzimidazol-2-yl | |
| 352 | 5-Cl-benzothiazol-2-yl | |
| 353 | 5-NO₂-benzoxazol-2-yl | |
| 354 | 5-t-Bu-benzoxazol-2-yl | |
| 355 | 4,6,7-Cl₃-benzothiozol-2-yl | |
| 356 | 5-Ph-thiazol-2-yl | |
| 357 | 5,7-Me₂-benzoxazol-2-yl | |
| 358 | 6-Me-benzoxazol-2-yl | |
| 359 | 1,2,4-triazin-3-yl | |
| 360 | 6-Pr-benzothiazol-2-yl | |
| 361 | 6-PhO-benzothiazol-2-yl | |
| 362 | 4-(4-Cl—Ph)-thiazol-2-yl | |
| 363 | 4-(4-Me—Ph)-thiazol-2-yl | |

TABLE 22-continued

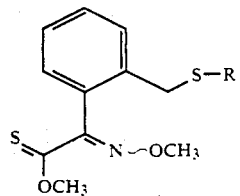

| No. | R | mp(°C.)/IR(cm⁻¹) |
|---|---|---|
| 364 | 5-Me-4-Ph-thiazol-2-yl | |
| 365 | 5-Cl-1-H-benzimidazol-2-yl | |
| 366 | 5-Ph-1,2,4-triazol-3-yl | |
| 367 | 3-Ph-1,2,4-thiadiazol-5-yl | |

TABLE 23

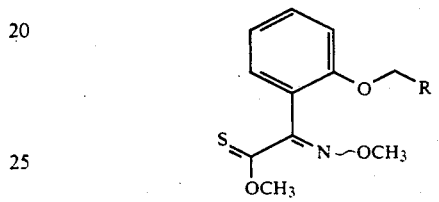

| No. | R | mp (°C.)/IR (cm⁻¹) |
|---|---|---|
| 1 | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-NO₂-phenyl | |
| 29 | 3-NO₃-phenyl | |
| 30 | 4-NO₂-phenyl | |
| 31 | 2-CH₃-phenyl | |
| 32 | 3-CH₃-phenyl | |
| 33 | 4-CH₃-phenyl | |
| 34 | 2-OMe-phenyl | |
| 35 | 3-OMe-phenyl | |
| 36 | 4-OMe-phenyl | |
| 37 | 2-CF₃-phenyl | |
| 38 | 3-CF₃-phenyl | |
| 39 | 4-CF₃-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |

TABLE 23-continued

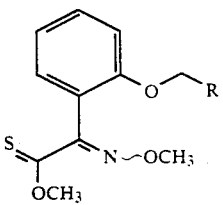

| No. | R | mp (°C.)/IR (cm$^{-1}$) |
|---|---|---|
| 50 | 2-thienyl | |
| 51 | 2-furyl | |
| 52 | 2-imidazolyl | |

TABLE 24

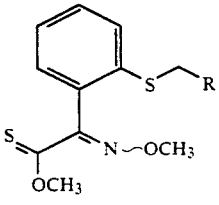

| No. | R | mp (°C.)/IR (cm$^{-1}$) |
|---|---|---|
| 1 | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-NO$_2$-phenyl | |
| 29 | 3-NO$_3$-phenyl | |
| 30 | 4-NO$_2$-phenyl | |
| 31 | 2-CH$_3$-phenyl | |
| 32 | 3-CH$_3$-phenyl | |
| 33 | 4-CH$_3$-phenyl | |
| 34 | 2-OMe-phenyl | |
| 35 | 3-OMe-phenyl | |
| 36 | 4-OMe-phenyl | |
| 37 | 2-CF$_3$-phenyl | |
| 38 | 3-CF$_3$-phenyl | |
| 39 | 4-CF$_3$-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |
| 50 | 2-thienyl | |

TABLE 24-continued

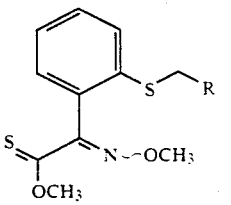

| No. | R | mp (°C.)/IR (cm$^{-1}$) |
|---|---|---|
| 51 | 2-furyl | |
| 52 | 2-imidazolyl | |

TABLE 25

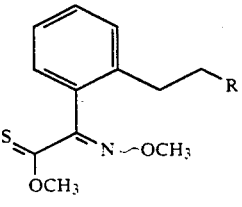

| No. | R | mp (°C.)/IR (cm$^{-1}$) |
|---|---|---|
| 1 | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-NO$_2$-phenyl | |
| 29 | 3-NO$_3$-phenyl | |
| 30 | 4-NO$_2$-phenyl | |
| 31 | 2-CH$_3$-phenyl | |
| 32 | 3-CH$_3$-phenyl | |
| 33 | 4-CH$_3$-phenyl | |
| 34 | 2-OMe-phenyl | |
| 35 | 3-OMe-phenyl | |
| 36 | 4-OMe-phenyl | |
| 37 | 2-CF$_3$-phenyl | |
| 38 | 3-CF$_3$-phenyl | |
| 39 | 4-CF$_3$-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |
| 50 | 2-thienyl | |
| 51 | 2-furyl | |

TABLE 25-continued

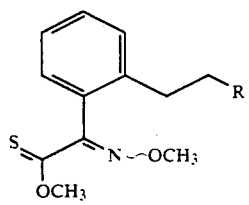

| No. | R | mp (°C.)/IR (cm$^{-1}$) |
|---|---|---|
| 52 | 2-imidazolyl | |

TABLE 26

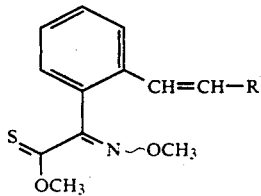

| No. | R | mp (°C.)/IR (cm$^{-1}$) |
|---|---|---|
| 1 | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-NO$_2$-phenyl | |
| 29 | 3-NO$_3$-phenyl | |
| 30 | 4-NO$_2$-phenyl | |
| 31 | 2-CH$_3$-phenyl | |
| 32 | 3-CH$_3$-phenyl | |
| 33 | 4-CH$_3$-phenyl | |
| 34 | 2-OMe-phenyl | |
| 35 | 3-OMe-phenyl | |
| 36 | 4-OMe-phenyl | |
| 37 | 2-CF$_3$-phenyl | |
| 38 | 3-CF$_3$-phenyl | |
| 39 | 4-CF$_3$-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |
| 50 | 2-thienyl | |
| 51 | 2-furyl | |

TABLE 26-continued

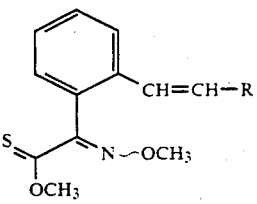

| No. | R | mp (°C.)/IR (cm$^{-1}$) |
|---|---|---|
| 52 | 2-imidazolyl | |

TABLE 27

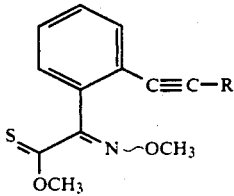

| No. | R | mp (°C.)/IR (cm$^{-1}$) |
|---|---|---|
| 1 | H | |
| 2 | methyl | |
| 3 | ethyl | |
| 4 | n-propyl | |
| 5 | i-propyl | |
| 6 | n-butyl | |
| 7 | i-butyl | |
| 8 | s-butyl | |
| 9 | t-butyl | |
| 10 | pentyl | |
| 11 | hexyl | |
| 12 | phenyl | |
| 13 | 1-naphthyl | |
| 14 | 2-naphthyl | |
| 15 | 3-phenanthrenyl | |
| 16 | 2-fluorophenyl | |
| 17 | 3-fluorophenyl | |
| 18 | 4-fluorophenyl | |
| 19 | 2-chlorophenyl | |
| 20 | 3-chlorophenyl | |
| 21 | 4-chlorophenyl | |
| 22 | 2-bromophenyl | |
| 23 | 3-bromophenyl | |
| 24 | 4-bromophenyl | |
| 25 | 2-iodophenyl | |
| 26 | 3-iodophenyl | |
| 27 | 4-iodophenyl | |
| 28 | 2-NO$_2$-phenyl | |
| 29 | 3-NO$_2$-phenyl | |
| 30 | 4-NO$_2$-phenyl | |
| 31 | 2-CH$_3$-phenyl | |
| 32 | 3-CH$_3$-phenyl | |
| 33 | 4-CH$_3$-phenyl | |
| 34 | 2-OMe-phenyl | |
| 35 | 3-OMe-phenyl | |
| 36 | 4-OMe-phenyl | |
| 37 | 2-CF$_3$-phenyl | |
| 38 | 3-CF$_3$-phenyl | |
| 39 | 4-CF$_3$-phenyl | |
| 40 | 2-Ph-phenyl | |
| 41 | 3-Ph-phenyl | |
| 42 | 4-Ph-phenyl | |
| 43 | 2-PhO-phenyl | |
| 44 | 3-PhO-phenyl | |
| 45 | 4-PhO-phenyl | |
| 46 | 2-pyridyl | |
| 47 | 2-pyrimidyl | |
| 48 | 2-quinalinyl | |
| 49 | 2-pyrryl | |
| 50 | 2-thienyl | |
| 51 | 2-furyl | |

TABLE 27-continued

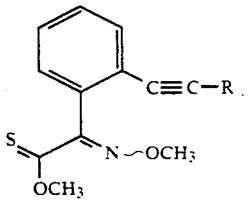

| No. | R | mp (°C.)/IR (cm$^{-1}$) |
|---|---|---|
| 52 | 2-imidazolyl | |

The novel thiocarboxylic esters I are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel thiocarboxylic esters are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples,
*Uncinula necator* in vines,
*Puccinia* species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables,
*Paecilomyces variotii* in timber.

The compounds are applied by spraying or dusting the plants with the active ingredients, or treating the seeds of the plants with the active ingredients. They may be applied before or after infection of the plants or seeds by the fungi. The compounds are used in fungicidally effective amounts.

The thiocarboxylic esters can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as ligninsulfite waste liquors and methylcellulose.

The agents may also be used for protecting wood.

The fungicides generally contain from 0.1 to 95, and preferably from 0.5 to 90, wt % of active ingredient. The application rates are from 0.02 to 3 kg or more of active ingredient per hectare, depending on the type of effect desired. When used for treating seed, amounts of from 0.01 to 50, and preferably from 0.01 to 10, g per kg of seed are required.

The agents, if desired after further dilution, are applied in conventional manner, for example by spraying, atomizing, dusting, scattering, dressing or watering.

Examples of formulations are given below.

I. A solution of 90 parts by weight of compound no. 15 (Table 3) and 10 parts by weight of N-methyl-α-pyrrolidone, which is suitable for application in the form of very fine drops.

II. A mixture of 20 parts by weight of compound no. 14 (Table 4), 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 243 (Table 4), 40 parts by weight of cyclohexanone, 30 parts by weight of isobutanol, 20 parts by weight of the adduct of 40 moles of ethylene oxide and 1 mole of castor oil. By pouring the mixture into water and finely dispersing it therein, an aqueous dispersion is obtained.

IV. An aqueous dispersion of 20 parts by weight of compound no. 15 (Table 3), 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the mixture into water and finely dispersing it therein, an aqueous dispersion is obtained.

V. A hammer-milled mixture of 80 parts by weight of compound no. 14 (Table 4), 3 parts by weight of the sodium salt of diisobutylnaphthalene-α-sulfonic acid, 10 parts by weight of the sodium salt of a ligninsulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 243 (Table 4) and 97 parts by weight of particulate kaolin. The dust contains 3 wt % of the active ingredient.

VII. An intimate mixture of 30 parts by weight of compound no. 15 (Table 3), 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 14 (Table 4), 10 parts of the sodium salt of a phenosulfonic acid-urea-formaldehyde condensate, 2 parts of silica gel and 48 parts of water, which dispersion can be further diluted.

IX. A stable oily dispersion of 20 parts by weight of compound no. 243 (Table 4), 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

USE EXAMPLES

The fungicidal action of the thiocarboxylic esters I was compared in the greenhouse with that of 2-(phenyloxymethyl)-phenylglyoxylic acid methyl ester-O-methyloxime (A) disclosed in EP 253,213.

EXAMPLE 1

Action on *Botrytis cinerea* in peppers

Pepper seedlings of the "Neusiedler Ideal Elite" variety were sprayed, after 4 to 5 leaves were well developed, to runoff with aqueous suspensions containing (dry basis) 80% of active ingredient and 20% of emulsifier. After 24 hours the treated plants were sprayed with a spore suspension of the fungus *Botrytis cinerea*. After having been cultivated for 8 days in the greenhouse, the treated plants were inoculated with a spore suspension of *Botrytis cinerea* containing $1.7 \times 10^6$ spores/ml in a 2% strength biomalt solution. They were then placed at 22° to 24° C. in a chamber of high humidity. After 5 days, the extent of the fungus spread was assessed.

Leaf surface area affected in %

| Active ingredient no. | Leaf attack after application of a 0.05% aqueous active ingredient formulation | |
|---|---|---|
| | Mark | % attack |
| Table 3, No. 24 | 1 | 5 |
| Table 4, No. 14 | 2 | 15 |
| Table 4, No. 243 | 2 | 15 |
| Comparative product A | 4-5 | 50 |
| Untreated | 5 | 65 |

EXAMPLE 2

Action on wheat brown rust

Leaves of pot-grown wheat seedlings of the "Kanzler" variety were dusted with spores of brown rust (*Puccinia recondita*). The pots were then placed for 24 hours at 20° to 22° C. in a high-humidity (90-95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

Assessment scale: 0 = no fungus attack, graded down to 5 = total fungus attack

| Active ingredient no. | Leaf attack after application of 0.025% aqueous active ingredient formulations | |
|---|---|---|
| | Mark | % attack |
| Table 4, No. 14 | 2 | 15 |
| Comparative product A | 4-5 | 50 |
| Untreated | 5 | 70 |

We claim:

1. Thiocarboxylic esters of the formula I

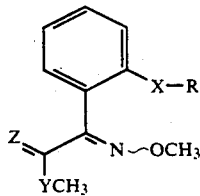

where the substituents have the following meanings:
X is oxygen, sulfur, oxymethylene, methyleneoxy, thiomethylene, methylenethio, ethylene, ethenylene or ethynylene,
Y, Z are each sulfur or oxygen, but Y and Z are not simultaneously oxygen,
R is $C_1$–$C_6$-alkyl, mononuclear, dinuclear or trinuclear carbocylic aryl, where aryl may carry the following radicals $R^1$:
  $R^1$ halogen, cyano, nitro, $C_1$–$C_6$-alkyl, $C_3$–$C_6$-cycloalkyl, $C_1$–$C_6$-alkoxy, trifluoromethyl, mononuclear or dinuclear aryloxy or mononuclear, dinuclear or trinuclear carbocyclic aryl, and aryloxy and carbocyclic aryl in turn may be substituted by the stated radicals $R^1$.

2. A fungicidal agent containing a fungicidally effective amount of a thiocarboxylic ester of the formula I

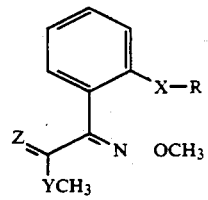

where the substituents have the following meanings:
X is oxygen, sulfur, oxymethylene, methyleneoxy, thiomethylene, methylenethio, ethylene, ethenylene or ethynylene,
Y, Z are each sulfur or oxygen, but Y and Z are not simultaneously oxygen,
R is $C_1$–$C_6$-alkyl, mononuclear, dinuclear or trinuclear carbocyclic aryl which may carry the following radicals $R^1$:
  $R^1$ halogen, cyano, nitro, $C_1$–$C_6$-alkyl, $C_3$–$C_6$-cycloalkyl, $C_1$–$C_6$-alkoxy, trifluoromethyl, mononuclear or dinuclear aryloxy or mononuclear, dinuclear or trinuclear carbocyclic aryl, and aryloxy and carbocyclic aryl in turn may be substituted by the stated radicals $R^1$,
and a conventional carrier.

3. A process for combating injurious fungi, wherein the fungi, or the plants, seed, materials or areas threatened by fungus attack are treated with a fungicidally effective amount of a thiocarboxylic ester of the formula I

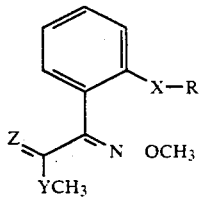

I where the substituents have the following meanings:
X is oxygen, sulfur, oxymethylene, methyleneoxy, thiomethylene, methylenethio, ethylene, ethenylene or ethynylene, Y, Z are each sulfur or oxygen, but Y and Z are not simultaneously oxygen,
R is $C_1$-$C_6$-alkyl, mononuclear, dinuclear or trinuclear carbocyclic aryl which carbocyclic aryl which may carry the following radicals $R^1$:
  $R^1$ halogen, cyano, nitro, $C_1$-$C_6$-alkyl, $C_3$-$C_6$-cycloalkyl, $C_1$-$C_6$-alkoxy, trifluoromethyl, mononuclear or dinuclear aryloxy or mononuclear, dinuclear or trinuclear carbocyclic aryl, and aryloxy and carbocyclic aryl in turn may be substituted by the stated radicals $R^1$.

4. Thiocarboxylic esters of the formula I as set forth in claim 1, where X is methyleneoxy, R is phenyl and $R^1$ is 2-chloro.

5. Thiocarboxylic esters of the formula I as set forth in claim 1, where X is methyleneoxy, R is phenyl and $R^1$ is 2-methyl.

6. Thiocarboxylic esters of the formula I as set forth in claim 1, where X is methylenethio, R is phenyl and $R^1$ is 2-chloro.

* * * * *